(12) United States Patent
Harrison et al.

(10) Patent No.: US 11,345,669 B2
(45) Date of Patent: May 31, 2022

(54) UREA DERIVATIVES AND METHODS OF USE THEREOF

(71) Applicant: NodThera Limited, Essex (GB)

(72) Inventors: David Harrison, Edinburgh (GB); Alan Paul Watt, Essex (GB); Nicolas Boutard, Cracow (PL); Charles-Henry Fabritius, Cracow (PL); Michal Galezowski, Cracow (PL); Piotr Kowalczyk, Cracow (PL); Oleksandr Levenets, Cracow (PL); Jakub Woyciechowski, Cracow (PL)

(73) Assignee: NodThera Limited, Essex (GB)

( * ) Notice: Subject to any disclaimer, the term of this patent is extended or adjusted under 35 U.S.C. 154(b) by 0 days.

(21) Appl. No.: 16/493,816

(22) PCT Filed: Mar. 12, 2018

(86) PCT No.: PCT/GB2018/050623
§ 371 (c)(1),
(2) Date: Sep. 13, 2019

(87) PCT Pub. No.: WO2018/167468
PCT Pub. Date: Sep. 20, 2018

(65) Prior Publication Data
US 2020/0131141 A1    Apr. 30, 2020

(30) Foreign Application Priority Data

Mar. 13, 2017 (GB) .................... 1703979

(51) Int. Cl.
| | |
|---|---|
| C07D 241/12 | (2006.01) |
| C07C 275/28 | (2006.01) |
| C07D 207/12 | (2006.01) |
| C07D 213/56 | (2006.01) |
| C07D 231/12 | (2006.01) |
| C07D 231/38 | (2006.01) |
| C07D 233/64 | (2006.01) |
| C07D 237/24 | (2006.01) |
| C07D 239/26 | (2006.01) |
| C07D 261/08 | (2006.01) |
| C07D 271/06 | (2006.01) |
| C07D 333/24 | (2006.01) |

(52) U.S. Cl.
CPC .......... *C07D 241/12* (2013.01); *C07C 275/28* (2013.01); *C07D 207/12* (2013.01); *C07D 213/56* (2013.01); *C07D 231/12* (2013.01); *C07D 231/38* (2013.01); *C07D 233/64* (2013.01); *C07D 237/24* (2013.01); *C07D 239/26* (2013.01); *C07D 261/08* (2013.01); *C07D 271/06* (2013.01); *C07D 333/24* (2013.01)

(58) Field of Classification Search
CPC .. C07D 207/12; C07D 213/06; C07D 213/56; C07D 231/12; C07D 231/14; C07D 231/38; C07D 233/10; C07D 233/64; C07D 233/96; C07D 237/08; C07D 237/24; C07D 239/26; C07D 241/12; C07D 261/08; C07D 271/06; C07D 271/10; C07D 333/24
See application file for complete search history.

(56) References Cited

U.S. PATENT DOCUMENTS

| | | | |
|---|---|---|---|
| 8,880,266 B2 | 11/2014 | Matsuda | |
| 9,198,845 B2 | 12/2015 | Natsch et al. | |
| 9,453,226 B2 | 9/2016 | Ambati et al. | |
| 2004/0209821 A1 | 10/2004 | Hamann et al. | |

FOREIGN PATENT DOCUMENTS

| | | |
|---|---|---|
| CN | 102977016 B | 1/2015 |
| DE | 2423273 A1 | 12/1974 |
| DE | 3522938 A1 | 1/1987 |
| NL | 7501474 A | 8/1975 |
| WO | WO 98/07718 A1 | 2/1998 |
| WO | WO 2004/056755 A2 | 7/2004 |
| WO | WO 2007/076055 A2 | 7/2007 |
| WO | WO 2011/076784 A2 | 6/2011 |
| WO | WO 2012/056014 A1 | 5/2012 |
| WO | WO 2013/070600 A1 | 5/2013 |
| WO | WO 2016/131098 A1 | 8/2016 |
| WO | WO 2019/025467 A1 | 2/2019 |

OTHER PUBLICATIONS

Stella (J. Pharmaceutical Sciences, 2010, 99(12), pp. 4755-4765).*
STN Datbase search (Registry Nos. 1009508-14-8 and 1008464-19-4, downloaded, Jan. 14, 2021, pp. 1-2).*
STN Datbase search (Registry Nos. 1043453-71-9, 1042988-46-4, 1042699-95-5 and 1042694-80-3, downloaded, Jan. 14, 2021, pp. 1-3).*
Aggarwal, B.B. et al. (2009) "Targeting inflammatory pathways for prevention and therapy of cancer: short-term friend, long-term foe" Clinical Cancer Research, 15(2):425-430.

(Continued)

*Primary Examiner* — Susanna Moore
(74) *Attorney, Agent, or Firm* — Cooley LLP; Heidi A. Erlacher; Christine E. Dunne

(57) ABSTRACT

The present disclosure relates to compounds of Formula (I): and to their pharmaceutically acceptable salts, pharmaceutical compositions, methods of use, and methods for their preparation. The compounds disclosed herein inhibit the maturation of cytokines of the IL-1 family by inhibiting inflammasomes and may be used in the treatment of disorders in которой inflammasome activity is implicated, such as inter alia autoinflammatory and autoimmune diseases and cancers.

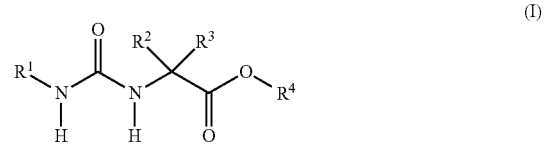

(I)

20 Claims, No Drawings

(56) References Cited

OTHER PUBLICATIONS

Ahmad, I. et al. (Jul. 2013) "Thymoquinone suppresses metastasis of melanoma cells by inhibition of NLRPB inflammasome" Toxicology and Applied Pharmacology, 270(1):70-76.
Amieva, M. and R.M. Peek (Jan. 2016) "Pathobiology of Helicobacter pylori-Induced Gastric Cancer" Gastroenterology, 150(1):64-78.
Apte, R.N. et al. (Sep. 2006) "The involvement of IL-1 in tumorigenesis, tumor invasiveness, metastasis and tumor-host interactions" Cancer and Metastasis Reviews, 25(3):387-408.
Basso, D. et al. (1996) "Helicobacter pylori infection enhances mucosal interleukin-Ibeta, interleukin-6, and the soluble receptor of interleukin-2" Int J Clin Lab Res, 26:207-210.
Bernstein, C.N. et al. (Feb. 2001) "Cancerriskinpatients with inflammatory bowel disease: a population-based study" Cancer, 91(4):854-862.
Bruchard, M. et al. (Jan. 2013) "Chemotherapy-triggered cathepsin B release in myeloid-derived suppressor cells activates the Nlrp3 inflammasome and promotes tumour growth" Nature Medicine, 19(1):57-64; including "Online Methods", 2 pages.
Carrascal, M.T. et al. (2003) "Interleukin-18 binding protein reduces B16 melanoma hepatic metastasis by neutralizing adhesiveness and growth factors of sinusoidal endothelium" Cancer Research, 63(2):491-497.
Coll, R.C. et al. (Mar. 2015) "A small-molecule inhibitor of the NLRP3 inflammasome for the treatment of inflammatory diseases" Nature Medicine, 21(3):248-255; indluding "Online Methods", 2 pages.
Database Caplus Accession No. 1909:2179 (1909) Vallee, C.: Phenyl, Naphthyl and Menthyl Isocyanates.[Online], Chemical Abstracts Service, Columbus, Ohio, US; retrieved from STN on Apr. 23, 2018, 3 pages.
Database Caplus Accession No. 1909:2179 (1909) Vallee, C.: Phenyl, Naphthyl and Menthyl Isocyanates.[Online], Chemical Abstracts Service, Columbus, Ohio, US; retrieved from STN in 2017, 3 pages.
Dinarello, C.A. et al. (Aug. 2010) "Role of IL-1 in type 2 diabetes" Curr Opin Endocrinol Diabetes Obes, 17(4):314-321.
Dinarello, C.A. (Mar. 2004) "Unraveling the NALP-3/IL-lbeta inflammasome: a big lesson from a small mutation" Immunity, 20(3):243-244.
Elaraj, D.M. et al. (Feb. 2006) "The role of interleukin 1 in growth and metastasis of human cancer xenografts" Clinical Cancer Research, 12(4):1088-1096.
Gabay, C. and I.B. McInnes (2009) "The biological and clinical importance of the 'new generation' cytokines in rheumatic diseases" Arthritis Research & Therapy, 11(3):230, 14 pages.
Gasse, P et al. (May 2009) "Uric acid is a danger signal activating NALP3 inflammasome in lung injury inflammation and fibrosis" Am J Respir Crit Care Med, 179(10):903-913.
Grivennikov, S.I. et al. (Mar. 2010) "Immunity, inflammation, and cancer" Cell, 140(6):883-899.
Halle, A. et al. (Aug. 2008) "The NALP3 inflammasome is involved in the innate immune response to amyloid-beta" Nat Immunol, 9(8):857-865.
Heneka, M.T. et al. (Jan. 2013) "NLRP3 is activated in Alzheimer's disease and contributes to pathology in APP/PS1 mice" Nature, 493:674-678; including "Methods", 3 pages.
Hoffman, H.M. et al. (Nov. 2001) "Mutation of a new gene encoding a putative pyrin-like protein causes familial cold autoinflammatory syndrome and Muckle-Wells syndrome" Nat Genet, 29(3):301-305.
Hoffman, H.M. al. (2005) "Periodic Fever Disorders" Reumatologia, 21(3):96-100.
Holen, I. et al. (Nov. 2016) "IL-1 drives breast cancer growth and bone metastasis in vivo" Oncotarget, 7(46):75571-75584.
Kagan, J. and Horng, T. (Aug. 2013) "NLRP3 inflammasome activation: CD36 serves double duty" Nature Immunology, 14(8):772-774.
Kim, J.M. (Dec. 2011) "Inflammatory Bowel Diseases and Inflammasome" Korean J Gastroenterol, vol. 58 No. 6, pp. 300-310 (Korean, English Abstract on p. 300).
Latz, E. et al. (Jun. 2013) "Activation and regulation of the inflammasomes" Nat Rev Immunol, 13(6):397-411.
Lázár-Molnár, E. et al. (2000) "Autocrine and paracrine regulation by cytokines and growth factors in melanoma" Cytokine, 12(6):547-554.
Lewis, A.M. et al. (Nov. 2006) "Interleukin-1 and cancer progression: the emerging role of interleukin-1 receptor antagonist as a novel therapeutic agent in cancer treatment" Journal of Translational Medicine, 4:48; 12 pages.
Li, L. and Liu, Y. (Dec. 2014) "Aging-related gene signature regulated by NlrpB predicts glioma progression" American Journal of Cancer Research, 5(1):442-449.
Ma et al. (2016) "Novel leucine ureido derivatives as aminopeptidase N inhibitors. Design, synthesis and activity evaluation" European Journal of Medicinal Chemistry, vol. 108, pp. 21-27, with Database CAPLUS [Online] Accession No. 2015:1924661 (2017), 2 pages.
Martinon, F. et al. (2009) "The inflammasomes: guardians of the body" Annu Rev Immunol, 27:229-265.
Masters, S.L. et al. (2009) "Horror Autoinflammaticus: The Molecular Pathophysiology of Autoinflammatory Disease" Annu Rev Immunol, 27:621-668.
Mortaz, E. et al. (2011) "Identification of Novel Therapeutic Targets in COPD" Tanaffos, 10(2):9-14.
Nath, A. et al. (Oct. 2015) "Elevated free fatty acid uptake via CD36 promotes epithelial-mesenchymal transition in hepatocellular carcinoma" Scientific Reports, 5:14752; 19 pages.
Pascual, G. et al. (Jan. 2017) "Targeting metastasis-initiating cells through the fatty acid receptor CD36" Nature, 541(7635):41-45; including Supplementary Information, 20 pages.
Perregaux, D.G. et al. (Oct. 2001) "Identification and characterization of a novel class of interleukin-1 post-translational processing inhibitors" J Pharmacol Exp Ther, 299(1):187-197.
Saresella, M. et al. (Mar. 2016) "The NLRP3 and NLRP1 inflammasomes are activated in Alzheimer's disease" Mol Neurodegener, 11:23; 14 pages.
Schett, G. et al. (Jan. 2016) "Interleukin-1 function and role in rheumatic disease" Nat Rev Rheumatol, 12(1):14-24.
Sims, J. and Smith, D.E. (Feb. 2010) "The IL-1 family: regulators of immunity" Nature Reviews Immunology, 10:89-102.
Voronov, E. et al. (Mar. 2003) "IL-1 is required for tumor invasiveness and angiogenesis" Proceedings of the National Academy of Sciences USA, 100(5):2645-2650.
Wang, P. et al. (2006) "Association of interleukin-1 gene polymorphisms with gastric cancer: a metaanalysis" Int J Cancer, 120:552-562.
Jee, C.D. et al. (2005) "Loss of *caspase*-1 gene expression in human gastric carcinomas and cell lines" Int J Oncol, 26:1265-1271.
Xu, Y. et al. (2013) "*Mycoplasma hyorhinis* Activates the NLRP3 Inflammasome and Promotes Migration and Invasion of Gastric Cancer Cells" PLoS ONE 8(11):e77955, 14 pages.
Zhang, B. et al. (2004) "IL-18 increases invasiveness of HL-60 myeloid leukemia cells: up-regulation of matrix metalloproteinases-9 (MMP-9) expression" Leukemia Research, 28(1):91-95.

\* cited by examiner

UREA DERIVATIVES AND METHODS OF USE THEREOF

RELATED APPLICATIONS

This application is a U.S. National Phase application, filed under U.S.C. § 371(c), of International Application No. PCT/GB2018/050623, filed Mar. 12, 2018, which claims priority to, and the benefit of, U.K. Application No. 1703979.3, filed Mar. 13, 2017, the contents of each of which is incorporated by reference herein in their entireties.

The present disclosure concerns particular novel compounds and directly related prodrugs, or pharmaceutically acceptable salt(s) thereof, which possess inflammasome inhibitory activity and are accordingly useful in methods of treatment of the human or animal body. The present disclosure also relates to processes for the preparation of these compounds, to pharmaceutical compositions comprising them, and to their use in the treatment of disorders in which inflammasome activity is implicated, such as autoinflammatory and autoimmune diseases.

BACKGROUND

Autoimmune diseases are associated with the overproduction of proinflammatory factors. One of them is interleukin-1 (IL-1), produced by activated macrophages, monocytes, fibroblasts and other components of the innate immune system like dendritic cells. It is involved in a variety of cellular activities, including cell proliferation, differentiation and apoptosis (Seth L. al. Rev. Immunol. 2009. 27:621-68).

Cytokines from the IL-1 family are highly active and, as important mediators of inflammation, are primarily associated with acute and chronic inflammation (Sims J. et al. Nature Reviews Immunology 10, 89-102 (February 2010)). The overproduction of IL-1 is considered to be a mediator of some autoimmune and autoinflammatory diseases. Autoinflammatory diseases are characterised by recurrent and unprovoked inflammation in the absence of autoantibodies, infection, or antigen-specific T lymphocytes.

Proinflammatory cytokines of the IL-1 superfamily include IL-1α, IL-1 β, IL-18, and IL-36α, β, A and are produced in response to pathogens and other cellular stressors as part of a host innate immune response. Unlike many other secreted cytokines which are processed and released via the standard cellular secretory apparatus consisting of the endoplasmic reticulum and Golgi apparatus, IL-1 family members lack leader sequences required for endoplasmic reticulum entry and thus are retained intracellularly following translation. In addition, IL-1 β, IL-18, and IL-36α, β, A are synthesised as procytokines that require proteolytic activation to become optimal ligands for binding to their cognate receptors on target cells.

In the case of IL-1α, IL-1 β and IL-18, it is now appreciated that a multimeric protein complex known as an inflammasome is responsible for activating the proforms of IL-1β and IL-18 and for release of these cytokines extracellularly. An inflammasome complex typically consists of a sensor molecule, such as an NLR (Nucleotide-Oligerimisation Domain (NOD)-like receptor), an adaptor molecule ASC (Apoptosis-associated speck-like protein containing a CARD (Capsase Recruitment Domain)) and procaspase-1. In response to a variety of "danger signals", including pathogen-associated molecule patterns (PAMPs) and danger associated molecular patterns (DAMPs), subunits of an inflammasome oligomerise to form a supermolecular structure within the cell. PAMPs include molecules such as peptidoglycan, viral DNA or RNA and bacterial DNA or RNA. DAMPs, on the other hand, consist of a wide range of endogenous sterile triggers including monosodium urate crystals, silica, alum, asbestos, fatty acids, ceramides, cholesterol crystals and aggregates of beta-amyloid peptide. Assembly of an inflammasome platform facilitates autocatalysis of procaspase-1 yielding a highly active cysteine protease responsible for activation and release of proIL-13 and pro-IL-18. Thus, release of these highly inflammatory cytokines is achieved only in response to inflammasome sensors detecting and responding to specific molecular danger signals.

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation including NLRP1, NLRP3, NLRP6, NLRP7, NLRP12 and NLRC4 (IPAF).

Two other structurally distinct inflammasome structures containing a PYHIN domain (pyrin and HIN domain containing protein) namely Absent in Melanoma 2 (AIM2) and IFNλ-inducible protein 16 (IFI16) (Latz et al., Nat Rev Immunol 2013 13(6) 397-311) serve as intracellular DNA sensors.

Requiring assembly of an inflammasome platform to achieve activation and release of IL-1 and IL-18 from monocytes and macrophages ensures their production is carefully orchestrated via a 2-step process. First, the cell must encounter a priming ligand (such as the TLR4 receptor ligand LPS, or an inflammatory cytokine such as TNFα) which leads NFκB dependent transcription of NLRP3, pro-IL-1β and pro-IL-18. The newly translated procytokines remain intracellular and inactive unless producing cells encounter a second signal leading to activation of an inflammasome scaffold and maturation of procaspase-1.

In addition to proteolytic activation of pro-IL-1β and pro-IL-18, active caspase-1 also triggers a form of inflammatory cell death known as pyroptosis through cleavage of gasdermin-D. Pyroptosis allows the mature forms of IL-1β and IL-18 to be externalised along with release of alarmin molecules (compounds that promote inflammation and activate innate and adaptive immunity) such as high mobility group box 1 protein (HMGB1), IL-33, and IL-1α.

Although inflammasome activation appears to have evolved as an important component of host immunity to pathogens, the NLRP3 inflammasome is unique in its ability to become activated in response to endogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1 and IL-18 being implicated in a diverse range of pathophysiological indications including metabolic, physiologic, inflammatory, hematologic and immunologic disorders.

A link to human disease is best exemplified by the discovery that mutations in the NLRP3 gene which lead to gain-of-function confer a range of autoinflammatory conditions collectively known as cryopyrin-associated periodic syndromes (CAPS) including familial cold autoinflammatory syndrome (FCAS), Muckle-Wells syndrome (MWS) and Neonatal onset multisystem inflammatory disease (NOMID) (Hoffman et al., Nat Genet. 29(3) (2001) 301-305). Likewise, sterile mediator-induced activation of NLRP3 has been implicated in a wide range of disorders including joint degeneration (gout, rheumatoid arthritis, osteoarthritis), cardiometabolic (type 2 diabetes, atherosclerosis, hypertension), Central Nervous System (Alzheimer's Disease, Parkinson's disease, multiple sclerosis), Gastrointestinal (Crohn's disease) lung (chronic obstructive pulmonary disease) and fibrosis (non-alcoholic fatty liver disease, non-alcoholic hepatosteatosis, idiopathic pulmonary fibrosis).

Current treatment options for diseases where IL-1 is implicated as a contributor to pathogenesis include the IL-1 receptor antagonist anakinra, an Fc-containing soluble fusion construct of the type 1 IL-1 receptor, the IL-1 receptor accessory protein rilonacept and the anti-IL-1β monoclonal antibody canakinumab. For example canakinumab is licenced for CAPS, Tumour Necrosis Factor Receptor Associated Periodic Syndrome (TRAPS), Hyperimmunoglobulin D Syndrome (HIDS)/Mevalonate Kinase Deficiency (MKD), Familial Mediterranean Fever (FMF) and gout.

Some small molecules have been reported to inhibit function of the NLRP3 inflammasome. Glyburide, for example, is a specific inhibitor of NLRP3 activation, albeit at micromolar concentrations which are unlikely attainable in vivo. Non-specific agents such as parthenolide, Bay 11-7082, and 3,4-methylenedioxy-β-nitrostyrene are reported to impair NLRP3 activation but are expected to possess limited therapeutic utility due to their sharing of a common structural feature consisting of an olefin activated by substitution with an electron withdrawing group; this can lead to undesirable formation of covalent adducts with protein-bearing thiol groups. A number of natural products, for example β-hydroxybutyrate, sulforaphane, quercetin, and salvianolic acid, also are reported to suppress NLRP3 activation. Likewise, numerous effectors/modulators of other molecular targets have been reported to impair NLRP3 activation including agonists of the G-protein coupled receptor TGR5, an inhibitor of sodium-glucose cotransport epigliflozin, the dopamine receptor antagonist A-68930, the serotonin reuptake inhibitor fluoxetine, fenamate non-steroidal anti-inflammatory drugs, and the β-adrenergic receptor blocker nebivolol. Utility of these molecules as therapeutics for the chronic treatment of NLRP3-dependent inflammatory disorders remains to be established. A series of sulfonylurea-containing molecules was previously identified as potent and selective inhibitors of post-translational processing of pro-IL-1β (Perregaux et al., J Pharmacol. Exp. Ther. 299, 187-197, 2001). The exemplar molecule CP-456,773 from this work was recently characterised as a specific inhibitor of NLRP3 activation (Coll et al., Nat Med 21.3 (2015): 248-255.).

The disclosure arises from a need to provide further compounds for the specific modulation of NLRP3-dependent cellular processes. In particular, compounds with improved physicochemical, pharmacological and pharmaceutical properties to existing compounds are desirable.

SUMMARY

According to a first aspect, the present disclosure relates to a compound of Formula (I), or a prodrug, or pharmaceutically acceptable salt thereof:

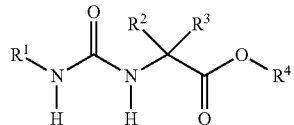

in which:
$R_1$ is a 5 or 6 membered alkyl or aryl monocycle, having at least one group substituent comprising a (2-8C) alkyl or a 9 or 10 membered bicyclic partially unsaturated carbocyclic ring system, wherein said bicyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$ or a 12, 13, 14, 15 or 16 membered tricyclic partially unsaturated carbocyclic ring system, wherein said tricyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$;

$R_2$ is H $R_3$ is Alkyl(C1-4)-$R_7$, wherein $R_7$ is selected from a 5 or 6 membered monocyclic aryl or non-aryl ring system comprising 1, 2 or 3 heteroatoms independently selected from oxygen, nitrogen and sulfur, or 3, 4, 5 or 6 membered monocyclic heterocyclyl ring system comprising 1 or 2 heteroatoms independently selected from oxygen, nitrogen and sulfur, wherein said heterocyclic $R_7$ ring system is optionally substituted with 1 or more substituents independently selected from (1-6C) alkyl, alkylhydroxy, nitro, OH, $COCH_3$, halo, amino, cyano, and $R_8$, or wherein $R_7$ is selected from a 5 or 6 membered monocyclic aryl or non-aryl ring system optionally comprising 1, 2 or 3 heteroatoms independently selected from oxygen, nitrogen and sulfur, or 3, 4, 5 or 6 membered monocyclic heterocyclyl ring system optionally comprising 1 or 2 heteroatoms independently selected from oxygen, nitrogen and sulfur or a 3, 4, 5 or 6 membered saturated or partially unsaturated carbocyclic ring system and wherein said $R_7$ ring system is substituted with 1 or more substituents independently selected from (1-6C) alkyl, alkylhydroxy, nitro, OH, COCH3, halo, amino, cyano, and $R_8$, wherein $R_8$ is, an optionally N-linked, 5 or 6 membered monocyclic heteroaryl ring comprising 1 or 2 heteroatoms independently selected from oxygen, nitrogen and sulfur, or a 3, 4, 5 or 6 membered monocyclic heterocyclyl ring system comprising 1 heteroatom independently selected from oxygen, nitrogen and sulfur, said ring being optionally substituted with an alkyl, oxo, halo or amino group; and $R_4$ is H, alkyl, monocyclic alkyl or monocyclic aryl group.

In some embodiments, $R_1$ is 12, 13, 14, 15 or 16 membered tricyclic partially unsaturated carbocyclic ring system selected from the group consisting of

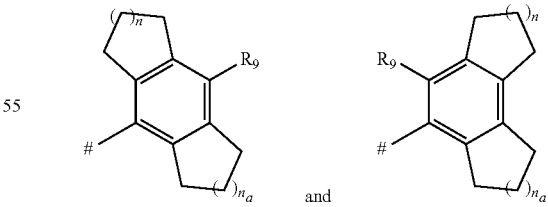

wherein # denotes the bond to the nitrogen atom of Formula (I); wherein n and $n_a$ is an integer independently selected from 0, 1, 2 and 3; and wherein $R_9$ is selected from the group consisting of hydrogen, (1-6C) alkyl, (2-6C)alkenylene, (2-6C)alkynylene, (3-8C)cycloalkyl, halo, oxo, hydroxy, cyano, amino, (1-3C) alkylamino, di-[(1-3C)alkyl]-amino, $CF_3$, $OCF_3$, $S(O)_2$ CH₃, S(O)CH₃, S(O)₂NH₂, S(O)₂NHCH₃, S(O)₂N(CH₃)₂, NHS(O)₂CH₃ and N(CH₃)S(O)₂CH₃;

or a 12, 13, 14, 15 or 16 membered tricyclic partially unsaturated carbocyclic ring system selected from the group consisting of

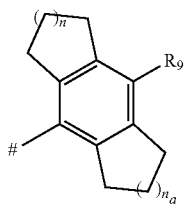 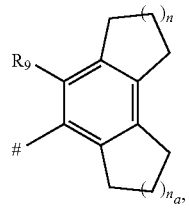

wherein # denotes the bond to the nitrogen atom of Formula (I); wherein n and $n_a$ is an integer independently selected from 0, 1, 2 and 3; and wherein $R_9$ is selected from the group consisting of hydrogen, (1-6C) alkyl, halo, $CF_3$ and $OCF_3$; or

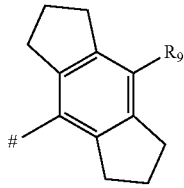 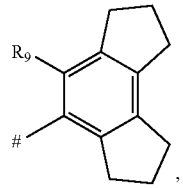

wherein # denotes the bond to the nitrogen atom of Formula (I); and wherein $R_9$ is selected from the group consisting of hydrogen, (1-6C)alkyl, (2-6C)alkenylene, (2-6C)alkynylene, (3-8C)cycloalkyl, halo, oxo, hydroxy, cyano, amino, (1-3C)alkylamino, di-[(1-3C) alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$; or

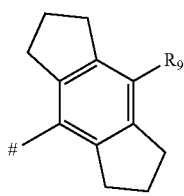

wherein # denotes the bond to the nitrogen atom of Formula (I); and wherein $R_9$ is selected from hydrogen, (1-6C)alkyl, halo, $CF_3$ and $OCF_3$; or an unsubstituted hexahydroindacene ring:

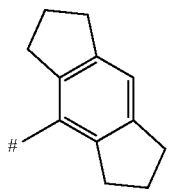

wherein # denotes the bond to the nitrogen atom of Formula (I).

According to a further aspect, the present disclosure relates to a compound of Formula (II), or a prodrug, or pharmaceutically acceptable salt thereof:

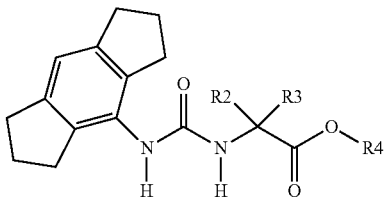

in which:
R₂ is H
R₃ Alkyl(C1-4)-R₇, wherein R₇ is
a 5 or 6 membered monocyclic aryl or non-aryl ring system comprising 1, 2 or 3 heteroatoms independently selected from oxygen, nitrogen and sulfur, or 3, 4, 5 or 6 membered monocyclic heterocyclyl ring system comprising 1 or 2 heteroatoms independently selected from oxygen, nitrogen and sulfur, wherein said heterocyclic R₇ ring system is optionally substituted with 1 or more substituents independently selected from (1-6C) alkyl, alkylhydroxy, nitro, OH, COCH₃, halo, amino, cyano, and R₈,
or
a 5 or 6 membered monocyclic aryl or non-aryl ring system optionally comprising 1, 2 or 3 heteroatoms independently selected from oxygen, nitrogen and sulfur, or 3, 4, 5 or 6 membered monocyclic heterocyclyl ring system optionally comprising 1 or 2 heteroatoms independently selected from oxygen, nitrogen and sulfur or a 3, 4, 5 or 6 membered saturated or partially unsaturated carbocyclic ring system and wherein said R₇ ring system is substituted with 1 or more substituents independently selected from (1-6C) alkyl, alkylhydroxy, nitro, OH, COCH3, halo, amino, cyano, and R₈,
wherein R₈ is, an optionally N-linked, 5 or 6 membered monocyclic heteroaryl ring comprising 1 or 2 heteroatoms independently selected from oxygen, nitrogen and sulfur, or a 3, 4, 5 or 6 membered monocyclic heterocyclyl ring system comprising 1 heteroatom independently selected from oxygen, nitrogen and sulfur, said ring being optionally substituted with an alkyl, oxo, halo or amino group; and
R₄ is H, alkyl, monocyclic alkyl or monocyclic aryl group.

The applicants have found that the compounds of the present disclosure serve as potent inhibitors of NLRP3 inflammasome activation, and as such are expected to be useful in the treatment of diseases in which inflammasome activity is implicated.

In some embodiments R₃ is Methyl or Ethyl-R₇.

Preferably, R₇ is a monocylic aryl optionally with at least one hydroxyl substitution.

Preferably, R₇ is a monocyclic aryl with a cyano substitution.

Preferably, R₇ is a 5 or 6 membered monocyclic aryl ring comprising 1, 2 or 3 heteroatoms independently selected from oxygen, nitrogen and sulfur.

In some embodiments R₄ is methyl or ethyl.

According to a further aspect there is provided a compound of Formula (I), or a prodrug, or pharmaceutically acceptable salt thereof:

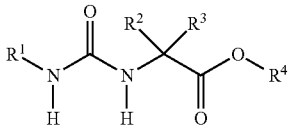

in which:
R₁ is a 5 or 6 membered alkyl or aryl monocycle, having at least one group substituent comprising a (2-8C) alkyl or a 9 or 10 membered bicyclic partially unsaturated carbocyclic ring system, wherein said bicyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$ or a 12, 13, 14, 15 or 16 membered tricyclic partially unsaturated carbocyclic ring system, wherein said tricyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$;

$R_2$ is H $R_3$ is Alkyl(C1-4)-$R_7$, wherein $R_7$ is selected from a 5 or 6 membered monocyclic aryl or non-aryl ring system comprising 1, 2 or 3 heteroatoms independently selected from oxygen, nitrogen and sulfur, or 3, 4, 5 or 6 membered monocyclic heterocyclyl ring system comprising 1 or 2 heteroatoms independently selected from oxygen, nitrogen and sulfur, wherein said ring system is optionally substituted with 1 or more substituents independently selected from (1-6C) alkyl, alkylhydroxy, nitro, OH, $COCH_3$, halo, amino, cyano, an optionally N-linked 5 or 6 membered monocyclic heteroaryl ring comprising 1 or 2 heteroatoms independently selected from oxygen, nitrogen and sulfur, or an optionally N-linked 3, 4, 5 or 6 membered monocyclic heterocyclyl ring system comprising 1 heteroatom independently selected from oxygen, nitrogen and sulfur, said ring being optionally substituted with an alkyl, oxo, halo or amino group; and $R_4$ is H, alkyl, monocyclic alkyl or monocyclic aryl group.

In yet a further aspect, the present disclosure relates to a compound of Formula (I), or a prodrug, or pharmaceutically acceptable salt thereof:

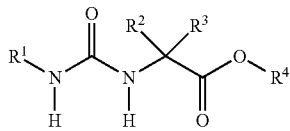

in which:

$R_1$ is a 5 or 6 membered alkyl or aryl monocycle, having at least one group substituent comprising a (2-8C) alkyl or a 9 or 10 membered bicyclic partially unsaturated carbocyclic ring system, wherein said bicyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$ or a 12, 13, 14, 15 or 16 membered tricyclic partially unsaturated carbocyclic ring system, wherein said tricyclic ring system is optionally substituted by 1, 2, 3 or 4 substituents independently selected from (1-6C)alkyl, (2-6C)alkenylene, (2-6C)alkynylene, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$ and $N(CH_3)S(O)_2CH_3$;

$R_2$ is H $R_3$ Alkyl(C1-4)-$R_7$, wherein $R_7$ is selected from a 5 or 6 membered monocyclic aryl or non-aryl ring system optionally comprising 1, 2 or 3 heteroatoms independently selected from oxygen, nitrogen and sulfur, or 3, 4, 5 or 6 membered monocyclic heterocyclyl ring system optionally comprising 1 or 2 heteroatoms independently selected from oxygen, nitrogen and sulfur or a 3, 4, 5 or 6 membered saturated or partially unsaturated carbocyclic ring system and said ring system is substituted with 1 or more substituents independently selected from (1-6C) alkyl, alkylhydroxy, nitro, OH, $COCH_3$, halo, amino, cyano, an optionally N-linked 5 or 6 membered monocyclic heteroaryl ring comprising 1 or 2 heteroatoms independently selected from oxygen, nitrogen and sulfur and an optionally N-linked 3, 4, 5 or 6 membered monocyclic heterocyclyl ring system comprising 1 heteroatom independently selected from oxygen, nitrogen and sulfur, said ring being optionally substituted with an alkyl, oxo, halo or amino group; and $R_4$ is H, alkyl, monocyclic alkyl or monocyclic aryl group.

According to a further aspect of the present disclosure, there is provided a pharmaceutical composition comprising a compound as defined herein, or a pharmaceutically acceptable salt thereof, in admixture with a pharmaceutically acceptable diluent or carrier.

According to a further aspect of the present disclosure, there is provided a method of inhibiting inflammasome (such as the NLRP3 inflammasome) activity in vitro or in vivo, said method comprising contacting a cell with an effective amount of a compound of Formula (I) or (II) or a pharmaceutically acceptable salt thereof as defined herein.

According to a further aspect of the present disclosure, there is provided a method of treating a disease or disorder in which inflammasome activity is implicated in a patient in need of such treatment, said method comprising administering to said patient a therapeutically effective amount of a compound of Formula (I) or (II) a pharmaceutically acceptable salt thereof as defined herein, or a pharmaceutical composition as defined herein.

According to a further aspect of the present disclosure, there is provided a method of treating an autoinflammatory disorder, an autoimmune disorder, a neurodegenerative disease or cancer in a patient in need of such treatment, said method comprising administering to said patient a therapeutically effective amount of a compound of Formula (I) or (II) a pharmaceutically acceptable salt thereof as defined herein, or a pharmaceutical composition as defined herein.

According to a further aspect of the present disclosure, there is provided a method of treating an autoinflammatory disorder and/or an autoimmune disorder selected from cryopyrin-associated autoinflammatory syndromes (CAPS) including familial cold autoinflammatory syndrome (FCAS), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), Non-alcoholic steatohepatitis (NASH), gout, rheumatoid arthritis, osteoarthritis, Crohn's disease, COPD, fibrosis, obesity, type 2 diabetes, multiple sclerosis and neuroinflammation occurring in protein misfolding diseases, such as Prion diseases in a patient in need of such treatment, said method comprising administering to said patient a therapeutically effective amount of a compound of Formula (I) or (II) or a pharmaceutically acceptable salt thereof as defined herein, or a pharmaceutical composition as defined herein.

According to a further aspect of the present disclosure, there is provided a method of treating a neurodegenerative disease such as Parkinson's disease or Alzheimer's disease in a patient in need of such treatment, said method comprising administering to said patient a therapeutically effective amount of a compound of Formula (I), (II) or a pharmaceutically acceptable salt thereof as defined herein, or a pharmaceutical composition as defined herein.

According to a further aspect of the present disclosure, there is provided a compound of Formula (I), (II) or a pharmaceutically acceptable salt thereof, or a pharmaceutical composition as defined herein for use in therapy.

According to a further aspect of the present disclosure, there is provided a compound of Formula (I), (II) or a pharmaceutically acceptable salt thereof as defined herein, or a pharmaceutical composition as defined herein, for use in the treatment of a disorder in which inflammasome activity is implicated.

In one embodiment the composition is for use in the treatment of a cancer. In particularly preferred embodiments the cancer is selected from a metastasising cancer, gastrointestinal cancer, skin cancer, non-small-cell lung carcinoma and colorectal adenocarcinoma.

According to a further aspect of the present disclosure, there is provided a compound of Formula (I), (II) or a pharmaceutically acceptable salt, hydrate or solvate thereof, or a pharmaceutical composition as defined herein for use in the treatment of an autoinflammatory disorder, an autoimmune disorder, a neurodegenerative disease or cancer. In a particular embodiment, the autoinflammatory or autoimmune disorder is a cryopyrin-associated autoinflammatory syndrome (CAPS) such as for example familial cold autoinflammatory syndrome (FCAS), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), gout, rheumatoid arthritis, Crohn's disease, COPD, fibrosis, obesity, type 2 diabetes, multiple sclerosis or neuro-inflammation occurring in protein misfolding diseases, such as Prion diseases. In a further embodiment, the neurodegenerative disease is Parkinson's disease or Alzheimer's disease, NASH and osteoarthritis.

According to a further aspect of the present disclosure, there is provided the use of a compound of Formula (I), (II) or a pharmaceutically acceptable salt thereof, as defined herein in the manufacture of a medicament for the treatment of an autoinflammatory disorder, an autoimmune disorder, a neurodegenerative disease or cancer. Suitably, the autoinflammatory or autoimmune disorder is cryopyrin-associated autoinflammatory syndrome (CAPS) such as for example familial cold autoinflammatory syndrome (FCAS), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), NASH, osteoarthritis, gout, rheumatoid arthritis, Crohn's disease, COPD, fibrosis, obesity, type 2 diabetes, or neuro-inflammation occurring in protein misfolding diseases, such as Prion diseases.

Suitably, the neurodegenerative disease is Parkinson's disease or Alzheimer's disease or multiple sclerosis According to a further aspect of the present disclosure, there is provided a process for preparing a compound of Formula (I), (II) or a pharmaceutically acceptable salt thereof, as defined herein.

According to a further aspect of the present disclosure, there is provided a compound of Formula (I), (II) or a pharmaceutically acceptable salt thereof, obtainable by, or obtained by, or directly obtained by a process of preparing a compound as defined herein.

According to a further aspect of the present disclosure, there are provided novel intermediates as defined herein which are suitable for use in any one of the synthetic methods set out herein.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

A link to human disease is best exemplified by discovery that mutations in the NLRP3 gene which lead to gain-of-function confer a range of autoinflammatory conditions collectively known as cryopyrin-associated periodic syndromes (CAPS) including familial cold autoinflammatory syndrome (FCAS), Muckle-Wells syndrome (MWS) and Neonatal onset multisystem inflammatory disease (NOMID) (Hoffman et al., Nat Genet. 29(3) (2001) 301-305). Likewise, sterile mediator-induced activation of NLRP3 has been implicated in a wide range of disorders including joint degeneration (gout, rheumatoid arthritis, osteoarthritis), cardiometabolic (type 2 diabetes, atherosclerosis, hypertension), Central Nervous System (Alzheimer's Disease, Parkinson's disease, multiple sclerosis), Gastrointestinal (Crohn's disease) lung (chronic obstructive pulmonary disease) and fibrosis (non-alcoholic fatty liver disease, non-alcoholic hepatosteatosis, idiopathic pulmonary fibrosis).

Definitions

Unless otherwise stated, the following terms used in the specification and claims have the following meanings set out below.

It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups such as propyl, isopropyl and t-butyl. However, references to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo]heptyl.

The term "halo" refers to fluoro, chloro, bromo and iodo.

Suitable values for the term "(1-6C)alkoxy" include methoxy, ethoxy, propoxy, isopropoxy and butoxy.

Suitable values for the term "(1-3C)alkylamino" include methylamino, ethylamino, propylamino and isopropylamino.

Suitable values for the term "di-[(1-3C)alkyl]-amino" include dimethylamino, diethylamino, N-ethyl-N-methylamino and diisopropylamino.

The term "aryl" means a cyclic or polycyclic aromatic ring having from 5 to 12 carbon atoms.

The term aryl includes both monovalent species and divalent species. Examples of aryl groups include, but are not limited to, phenyl, biphenyl, naphthyl and the like. Conveniently, an aryl is phenyl.

The term "5 membered monocyclic heteroaryl ring system" when used to define the ring system wherein the ring system, optionally comprises 1, 2 or 3 heteroatoms independently selected from oxygen, nitrogen and sulfur. Suitable examples include furyl, thiophenyl, pyrrolyl, isoxazolyl, thiazolyl, isothiazolyl, pyrazolyl, imidazolyl, oxadiazolyl, thiadiazolyl, triazolyl and tetrazolyl.

The term "8, 9 or 10 membered bicyclic heteroaryl ring system" when used to define the ring system formed, optionally comprises 1, 2 or 3 heteroatoms independently selected from oxygen, nitrogen and sulfur. Suitable examples include indolyl, isoindolyl, indazolyl, benzimidazolyl, benzoxathiazolyl, benzoxadiazolyl, benzothiadiazolyl, quinolinyl, isoquinolinyl, purinyl, 1,8-naphthyridyl, pteridyl, 1H-pyrrolo[3,2-b]pyridinyl, 1H-pyrrolo[2,3-c]pyridinyl, pyrido[3,2-d]pyrimidyl and pyridoimidazolyl. The term "8, 9 or 10 membered bicyclic heteroaryl ring system" also covers partially aromatic bicyclic ring systems wherein the first ring is aromatic and the other second ring is non-aromatic, saturated or partially saturated. Suitable examples of partially aromatic bicyclic ring systems include for example, 4,5,6,7-tetrahydroindolyl, 4,5,6,7-tetrahydroisoindolyl and 2H,4H,5H,6H-cyclopenta[c]pyrrolyl.

The term "5 or 6 membered monocyclic heteroaryl ring system" refers to a 5 or 6 membered aromatic ring system comprising 1, 2 or 3 heteroatoms independently selected from oxygen, nitrogen and sulfur. Suitable examples include furyl, thiophenyl, pyrrolyl, isoxazolyl, thiazolyl, isothiazolyl, pyrazolyl, imidazolyl, oxadiazolyl, thiadiazolyl, triazolyl, tetrazolyl, pyridyl, pyrimidinyl, pyrazinyl and pyridazinyl.

The term "3, 4, 5, or 6 membered monocyclic heterocyclyl ring system" refers to a 3, 4, 5, or 6 membered non-aromatic saturated or partially saturated heterocyclic ring system, wherein the ring system optionally comprises 1 or 2 heteroatoms independently selected from oxygen, nitrogen and sulfur, wherein a ring sulfur atom is optionally oxidized to form the S-oxide(s). Suitable examples include oxiranyl, aziridinyl, azetidinyl, oxetanyl, pyrrolinyl, pyrrolidinyl, imidazolinyl, imidazolidinyl, pyrazolinyl, pyrazolidinyl, morpholinyl, thiomorpholinyl, piperidinyl, homopiperidinyl, piperazinyl, homopiperazinyl, tetrahydrofuranyl, tetrahydropyran and tetrahydro-1,4-thiazinyl.

The term "12, 13, 14, 15 or 16 membered tricyclic partially unsaturated heterocyclic ring system" when used to define the ring system refers to a 12, 13, 14, 15 or 16 partially unsaturated heterocyclic ring system, which comprises 1 or 2 heteroatoms independently selected from oxygen, nitrogen and sulfur, wherein a ring sulfur atom is optionally oxidized to form the S-oxide(s). Suitable examples include rings such as 2-azatricyclo[7.3.0.0$^{3,7}$]dodeca-1,3(7),8-trienyl, 1,2,3,4,5,6,7,8-octahydroacridinyl, 7-azatricyclo[7.3.0.0$^{2,6}$]dodeca-1,6,8-trienyl, 1,2,3,4,7,8,9,10-octa hydrophenanthridinyl, 1H,2H,3H,6H,7H,8H,9H-cyclopenta[c]isoquinolinyl, 1H,2H,3H,6H,7H,8H,9H-cyclopenta[c]quinolonyl, 1H,2H,3H,5H,6H,7H,8H-cyclopenta[b]quinolonyl, 1H,2H,3H,5H,6H,7H-cyclopenta[b]pyrrolizinyl, 1H,2H,3H,5H,6H,7H,8H-cyclohexa[b]pyrrolizinyl, 1H,2H,3H,5H,6H,7H-cyclopenta[b]pyrrolizinyl and 1H,2H,3H,5H,6H,7H,8H-cyclopenta[b]indolizinyl.

The term "12, 13, 14, 15 or 16 membered tricyclic partially unsaturated carbocyclic ring system" comprising only carbon atoms. Suitable examples include rings such as 1,2,3,5,6,7-hexahydro-s-indacenyl, 1H,2H,3H,6H,7H,8H,9H-cyclopenta[a]naphthalenyl, 1,2,3,6,7,8-hexahydroas-indacenyl, 1,2,3,4,5,6,7,8-octa hydroanthracenyl, 1,2,3,4,5,6,7,8-octahydrophenanthrenyl and 1H,2H,3H,5H,6H,7H,8H-cyclopenta[b]naphthalenyl.

The term "3, 4, 5 or 6 membered saturated or partially unsaturated carbocyclic ring system" refers to a monocyclic ring system comprising only carbon atoms. Suitable examples include cyclopropanyl, cyclopentanyl, cyclohexanyl and cyclohexenyl.

The phrase "compound of the disclosure" means those compounds which are disclosed herein, both generically and specifically.

COMPOUNDS OF THE DISCLOSURE

For the avoidance of doubt it is to be understood that where in this specification a group is qualified by 'hereinbefore defined' or 'defined hereinbefore' the said group encompasses the first occurring and broadest definition as well as each and all of the particular definitions for that group.

Particular compounds of the disclosure include, for example, compounds of the Formula (I) or (II), or pharmaceutically acceptable salt thereof, wherein, unless otherwise stated, each of $R_1$, $R_2$, $R_3$, $R_4$ and any associated substituent groups has any of the meanings defined hereinbefore.

The various functional groups and substituents making up the compounds of the Formula (I) or (II) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

It will be understood that the compounds of Formula (I), (II) and any pharmaceutically acceptable salts thereof, comprise stereoisomers, mixtures of stereoisomers, polymorphs of all isomeric forms of said compounds.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is also to be understood that certain compounds of the Formula (I) or (II) may exist in solvated as well as unsolvated forms such as, for example, hydrated forms. A suitable pharmaceutically-acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of the Formula (I) or (II) may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of the Formula (I) or (II) may exist in a number of different tautomeric forms and references to compounds of the formula I include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

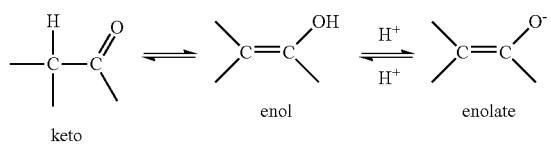

keto / enol / enolate

Compounds of the Formula (I) or (II) containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula (I) or (II) may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include in vivo cleavable ester derivatives that may be formed at a carboxy group or a hydroxy group in a compound of the Formula (I) or (II) and in vivo cleavable amide derivatives that may be formed at a carboxy group or an amino group in a compound of the Formula (I) or (II).

Accordingly, the present disclosure includes those compounds of the Formula (I) or (II) as defined hereinbefore when made available by organic synthesis and when made available within the human or animal body by way of cleavage of a prodrug thereof. Accordingly, the present disclosure includes those compounds of the Formula (I) or (II) that are produced by organic synthetic means and also such compounds that are produced in the human or animal body by way of metabolism of a precursor compound, that is a compound of the Formula (I) or (II) may be a synthetically-produced compound or a metabolically-produced compound.

A suitable pharmaceutically acceptable prodrug of a compound of the Formula (I) or (II) is one that is based on reasonable medical judgment as being suitable for administration to the human or animal body without undesirable pharmacological activities and without undue toxicity. Various forms of prodrug have been described, for example in the following documents:—
a) Methods in Enzymology, Vol. 42, p. 309-396, edited by K. Widder, et al. (Academic Press, 1985);
b) Design of Prodrugs, edited by H. Bundgaard, (Elsevier, 1985);
c) A Textbook of Drug Design and Development, edited by Krogsgaard-Larsen and H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "ProDrugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable prodrug of a compound of the Formula (I) or (II) that possesses a carboxy group is, for example, an in vivo cleavable ester thereof. An in vivo cleavable ester of a compound of the Formula (I) or (II) containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable prodrug of a compound of the Formula (I) or (II) that possesses a hydroxy group is, for example, an in vivo cleavable ester or ether thereof. An in vivo cleavable ester or ether of a compound of the Formula (I) or (II) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include (1-10C) alkanoyl groups such as acetyl, benzoyl, phenylacetyl and substituted benzoyl and phenylacetyl groups, (1-10C) alkoxycarbonyl groups such as ethoxycarbonyl, N,N—(C1-6)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of the Formula (I) or (II) that possesses a carboxy group is, for example, an in vivo cleavable amide thereof, for example an amide formed with an amine such as ammonia, a C1-4alkylamine such as methylamine, a (C1-4alkyl)2amine such as dimethylamine, N-ethyl-N-methylamine or diethylamine, a C1-4alkoxy-C2-4alkylamine such as 2-methoxyethylamine, a phenyl-C1-4alkylamine such as benzylamine and amino acids such as glycine or an ester thereof.

A suitable pharmaceutically acceptable prodrug of a compound of the Formula (I) or (II) that possesses an amino group is, for example, an in vivo cleavable amide derivative thereof. Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the Formula (I) or (II) may be exerted in part by one or more metabolites that are formed within the human or animal body after administration of a compound of the Formula (I) or (II). As stated hereinbefore, the in vivo effects of a compound of the Formula (I) or (II) may also be exerted by way of metabolism of a precursor compound (a prodrug).

Though the present disclosure may relate to any compound or particular group of compounds defined herein by way of optional, preferred or suitable features or otherwise in terms of particular embodiments, the present disclosure may also relate to any compound or particular group of compounds that specifically excludes said optional, preferred or suitable features or particular embodiments. A feature of the disclosure concerns particular structural groups at R1, which is relevant to the scope of the claims, as defined herein. In some cases, specific groups define structures that are not relevant to the present invention and thus may be disclaimed. Such structures may be disclaimed where R1 corresponds to a phenyl directly substituted with at least 2 groups including: 1 halogen group and 1 methyl group; 2 or more halogen groups; or 2 methyl groups.

Suitably, the present disclosure excludes any individual compounds not possessing the biological activity defined herein.

General Methods of Preparation

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) or (II) has been synthesised by any one of the processes defined herein, the processes may then further comprise the additional steps of:
(i) removing any protecting groups present;
(ii) converting the compound Formula (I) or (II) into another compound of Formula (I) or (I);
(iii) forming a pharmaceutically acceptable salt, hydrate or solvate thereof; and/or
(iv) forming a prodrug thereof.

The resultant compounds of Formula (I) or (II) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about $-100°$ C. and $300°$ C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

Pharmaceutical Compositions

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well-known principles of medicine.

In using a compound of the disclosure for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this disclosure.

Therapeutic Uses and Applications

The present disclosure provides compounds that function as inhibitors of inflammasome activity. The present disclosure therefore provides a method of inhibiting inflammasome activity in vitro or in vivo, said method comprising contacting a cell with an effective amount of a compound, or a pharmaceutically acceptable salt thereof, as defined herein.

Effectiveness of compounds of the disclosure can be determined by industry-accepted assays/disease models according to standard practices of elucidating the same as described in the art and are found in the current general knowledge.

The present disclosure also provides a method of treating a disease or disorder in which inflammasome activity is implicated in a patient in need of such treatment, said method comprising administering to said patient a therapeutically effective amount of a compound, or a pharmaceutically acceptable salt thereof, or a pharmaceutical composition as defined herein.

On a general level, the compounds of the present disclosure, which inhibit the maturation of cytokines of the IL-1 family, are effective in all therapeutic indications that are mediated or associated with elevated levels of active forms of cytokines belonging to IL-1 family of cytokines (Sims J. et al. Nature Reviews Immunology 10, 89-102 (February 2010).

Exemplary diseases and the corresponding references will be given in the following: autoinflammatory and autoimmune diseases like CAPS (Dinarello C A. Immunity. 2004 March; 20(3):243-4; Hoffman H M. al. Reumatologia 2005; 21(3)), gout, rheumatoid arthritis (Gabay C et al. Arthritis Research & Therapy 2009, 11:230; Schett G. et al. Nat Rev Rheumatol. 2016 January; 12(1):14-24.), Crohn's disease (Jung Mogg Kim Korean J Gastroenterol Vol. 58 No. 6, 300-310), COPD (Mortaz E. et al. Tanaffos. 2011; 10(2): 9-14.), fibrosis (Gasse P. et al. Am J Respir Crit Care Med. 2009 May 15; 179(10):903-13), obesity, type 2 diabetes ((Dinarello C A. et al. Curr Opin Endocrinol Diabetes Obes. 2010 August; 17(4):314-21)) multiple sclerosis (see EAE-model in Coil R C. et al. Nat Med. 2015 March; 21(3):248-55) and many others (Martinon F. et al. Immunol. 2009. 27:229-65) like Parkinson's disease or Alzheimer's disease (Michael T. et al. Nature 493, 674-678 (31 Jan. 2013); Halle A. et al., Nat Immunol. 2008 August; 9(8):857-65; Saresella M. et al. Mol Neurodegener. 2016 Mar. 3; 11:23) and even some oncological disorders.

Suitably, the compounds according to the present disclosure can be used for the treatment of a disease selected from the group consisting of an autoinflammatory disease, an autoimmune disease, a neurodegenerative disease and cancer. Said autoinflammatory and autoimmune disease is suitably selected from the group consisting of NASH, osteoarthritis cancer, a cryopyrin-associated periodic syndrome (CAPS) (such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever and nonalcoholic fatty liver disease (NAFLD), gout, rheumatoid arthritis, Crohn's disease, COPD, fibrosis, obesity, type 2 diabetes, multiple sclerosis and neuroinflammation occurring in protein misfolding diseases, such as Prion diseases. Said neurodegenerative disease is suitably selected from Parkinson's disease and Alzheimer's disease.

Accordingly, the compounds of the present disclosure can be used for the treatment of a disease selected from the group consisting of cryopyrin-associated periodic syndrome (CAPS) such as for example familial cold autoinflammatory syndrome (FCAS), Muckle-Wells syndrome (MWS), chronic infantile neurological cutaneous and articular (CINCA) syndrome, neonatal-onset multisystem inflammatory disease (NOMID), familial Mediterranean fever and nonalcoholic fatty liver disease (NAFLD), gout, rheumatoid arthritis, Crohn's disease, COPD, fibrosis, obesity, type 2 diabetes, multiple sclerosis, neuroinflammation occurring in protein misfolding diseases, such as Prion diseases, Parkinson's disease and Alzheimer's disease.

Treatment in Cancer; Links with Inflammasome

Chronic inflammation responses have long been observed to be associated with various types of cancer. During malignant transformation or cancer therapy inflammasomes may become activated in response to danger signals and this activation may be both beneficial and detrimental in cancer.

IL-1 expression is elevated in a variety of cancers (including breast, prostate, colon, lung, head and neck cancers and melanomas) and patients with IL-1 producing tumours generally have a worse prognosis (Lewis, Anne M., et al. "Interleukin-1 and cancer progression: the emerging role of interleukin-1 receptor antagonist as a novel therapeutic agent in cancer treatment." Journal of translational medicine 4.1 (2006): 48).

Cancers derived from epithelial cells (carcinoma) or epithelium in glands (adenocarcinoma) are heterogeneous; consisting of many different cell types. This may include fibroblasts, immune cells, adipocytes, endothelial cells and pericytes amongst others, all of which may be cytokine/chemokine secreting (Grivennikov, Sergei I., Florian R. Greten, and Michael Karin. "Immunity, inflammation, and cancer." Cell 140.6 (2010): 883-899). This can lead to cancer-associated inflammation through the immune cell infiltration. The presence of leukocytes in tumours is known but it has only recently become evident that an inflammatory microenvironment is an essential component of all tumours. Most tumours (>90%) are the result of somatic mutations or environmental factors rather than germline mutations and many environmental causes of cancer are associated with chronic inflammation (20% of cancers are related to chronic infection, 30% to smoking/inhaled pollutants and 35% to dietary factors (20% of all cancers are linked to obesity) (Aggarwal, Bharat B., R. V. Vijayalekshmi, and Bokyung Sung. "Targeting inflammatory pathways for prevention and therapy of cancer: short-term friend, long-term foe." Clinical Cancer Research 15.2 (2009): 425-430).

GI Cancer

Cancers of the gastrointestinal (GI) tract are frequently associated with chronic inflammation. For example, *H. pylori* infection is associated with gastric cancer (Amieva, Manuel, and Richard M. Peek. "Pathobiology of *Helicobacter pylori*-Induced Gastric Cancer." Gastroenterology 150.1 (2016): 64-78). Colorectal cancer is associated with inflammatory bowel disease (Bernstein, Charles N., et al. "Cancer risk in patients with inflammatory bowel disease." Cancer 91.4 (2001): 854-862). Chronic inflammation in stomach leads to the upregulation of IL-1 and other cytokines (Basso D, et al., (1996) *Helicobacter pylori* infection enhances mucosal interleukin-1 beta, interleukin-6, and the soluble receptor of interleukin-2. Int J Clin Lab Res 26:207-210) and polymorphisms in IL-1 gene can increase risk of gastric cancer (Wang P, et al., (2007) Association of interleukin-1 gene polymorphisms with gastric cancer: a meta-analysis. Int J Cancer 120:552-562).

In 19% of gastric cancer cases, caspase-1 expression is decreased which correlates with stage, lymph node metastasis and survival (Jee et al., 2005). *Mycoplasma hyorhinis* is associated with the development of gastric cancer its activation of the NLRP3 inflammasome may be associated with its promotion of gastric cancer metastasis (Xu et al., 2013).

Skin Cancers

Ultraviolet radiation is the greatest environmental risk for skin cancer which is promoted by causing DNA damage, immunosuppression and inflammation. The most malignant skin cancer, melanoma, is characterised by the upregulation of inflammatory cytokines, all of which can be regulated by IL-1 (Lázár-Molnar, Eszter, et al. "Autocrine and paracrine regulation by cytokines and growth factors in melanoma." Cytokine 12.6 (2000): 547-554). Systemic inflammation induces an enhancement of melanoma cell metastasis and growth by IL-1-dependent mechanisms in vivo. Using thymoquinone inhibition of metastasis in a B16F10 mouse melanoma model was shown to be dependent on inhibition of the NLRP3 inflammasome (Ahmad, Israr, et al. "Thymoquinone suppresses metastasis of melanoma cells by inhibition of NLRP3 inflammasome." Toxicology and applied pharmacology 270.1 (2013): 70-76).

Glioblastoma

NLRP3 contributes to radiotherapy resistance in glioma. Ionising radiation can induce NLRP3 expression whereas NLRP3 inhibition reduced tumour growth and prolonged mouse survival following radiation therapy. NLRP3 inflammasome inhibition can therefore provide a therapeutic strategy for radiation-resistant glioma (Li, Lianling, and Yuguang Liu. "Aging-related gene signature regulated by Nlrp3 predicts glioma progression." American journal of cancer research 5.1 (2015): 442).

Metastasis

More widely, NLRP3 is considered by the applicants to be involved in the promotion of metastasis and consequently modulation of NLRP3 should plausibly block this. IL-1 is involved in tumour genesis, tumour invasiveness, metastasis, tumour host interactions (Apte, Ron N., et al. "The involvement of IL-1 in tumorigenesis, tumor invasiveness, metastasis and tumor-host interactions." Cancer and Metastasis Reviews 25.3 (2006): 387-408) and angiogenesis (Voronov, Elena, et al. "IL-1 is required for tumor invasiveness and angiogenesis." Proceedings of the National Academy of Sciences 100.5 (2003): 2645-2650).

The IL-1 gene is frequently expressed in metastases from patients with several types of human cancers. For example, IL-1 mRNA was highly expressed in more than half of all tested metastatic human tumour specimens including specifically non-small-cell lung carcinoma, colorectal adenocarcinoma, and melanoma tumour samples (Elaraj, Dina M., et al. "The role of interleukin 1 in growth and metastasis of human cancer xenografts." Clinical Cancer Research 12.4 (2006): 1088-1096) and IL-1RA inhibits xenograft growth in IL-1 producing tumours but without anti-proliferative effects in vitro.

Further, IL-1 signalling is a biomarker for predicting breast cancer patients at increased risk for developing bone metastasis. In mouse models IL-1β and its receptor are upregulated in breast cancer cells that metastasise to bone compared with cells that do not. In a mouse model the IL-1 receptor antagonist anakinra reduced proliferation and angiogenesis in addition to exerting significant effects on the tumour environment reducing bone turnover markers, IL-1β and TNF alpha (Holen, Ingunn, et al. "IL-1 drives breast cancer growth and bone metastasis in vivo." Oncotarget (2016).

IL-18 induced the production of MMP-9 in the human leukaemia cell line HL-60, thus favouring degradation of the extracellular matrix and the migration and invasiveness of cancer cells (Zhang, Bin, et al. "IL-18 increases invasiveness of HL-60 myeloid leukemia cells: up-regulation of matrix metalloproteinases-9 (MMP-9) expression." Leukemia research 28.1 (2004): 91-95). Additionally IL-18 can support the development of tumour metastasis in the liver by inducing expression of VCAM-1 on hepatic sinusoidal endothelium (Carrascal, Maria Teresa, et al. "Interleukin-18 binding protein reduces b16 melanoma hepatic metastasis by neutralizing adhesiveness and growth factors of sinusoidal endothelium." Cancer Research 63.2 (2003): 491-497).

CD36

The fatty acid scavenger receptor CD36 serves a dual role in priming gene transcription of pro-IL-1β and inducing assembly of the NLRP3 inflammasome complex. CD36 and the TLR4-TLR6 heterodimer recognize oxLDL, which initiates a signaling pathway leading to transcriptional upregulation of NLRP3 and pro-IL-1β (signal 1). CD36 also mediates the internalisation of oxLDL into the lysosomal compartment, where crystals are formed that induce lysosomal rupture and activation of the NLRP3 inflammasome (signal 2) (Kagan, J. and Horng T., "NLRP3 inflammasome activation: CD36 serves double duty." Nature immunology 14.8 (2013): 772-774).

A subpopulation of human oral carcinoma cells express high levels of the fatty acid scavenger receptor CD36 and are unique in their ability to initiate metastasis. Palmitic acid or a high fat diet boosted the metastatic potential of the CD36+ cells. Neutralising anti-CD36 antibodies blocked metastasis in orthotopic mouse models of human oral cancer. The presence of CD36+ metastasis-initiating cells correlates with a poor prognosis for numerous types of carcinomas. It is suggested that dietary lipids may promote metastasis (Pasqual, G, Avgustinova, A., Mejetta, S, Martin, M, Castellanos, A, Attolini, C S-O, Berenguer, A., Prats, N, Toll, A, Hueto, J A, Bescos, C, Di Croce, L, and Benitah, S A. 2017 "Targeting metastasis-initiating cells through the fatty acid receptor CD36" Nature 541:41-45).

In hepatocellular carcinoma exogenous palmitic acid activated an epithelial-mesenchymal transition (EMT)-like program and induced migration that was decreased by the CD36 inhibitor, sulfo-N-succinimidyl oleate (Nath, Aritro, et al. "Elevated free fatty acid uptake via CD36 promotes epithelial-mesenchymal transition in hepatocellular carcinoma." Scientific reports 5, 2015). Body mass index was not associated with the degree of EMT, highlighting that it is actually CD36 and free fatty acids that are important.

Cancer stems cells (CSCs) use CD36 to promote their maintenance. Oxidised phospholipids, ligands of CD36, were present in glioblastoma and the proliferation of CSCs but not non-CSCs increased with exposure to oxidised LDL. CD36 also correlated with patient prognosis.

Chemotherapy Resistance

In addition to direct cytotoxic effects, chemotherapeutic agents harness the host immune system which contributes to anti-tumour activity. However, gemcitabine and 5-FU were shown to activate NLRP3 in myeloid-derived suppressor cells leading to production of IL-1 which curtails anti-tumour efficacy. Mechanistically these agents destabilised the lysosome to release cathepsin B to activate NLRP3. IL-1 drove the production of IL-17 from CD4+ T cells which in turn blunted the efficacy of the chemotherapy. Higher anti-tumoural effects for both gemcitabine and 5-FU were observed when tumours were established in NLRP3$^{-/-}$ or Caps1$^{-/-}$ mice, or WT mice treated with IL-1RA. Myeloid-derived suppressor cell NLRP3 activation therefore limits the anti-tumour efficacy of gemcitabine and 5-FU (Bruchard, Melanie, et al. "Chemotherapy-triggered cathepsin B release in myeloid-derived suppressor cells activates the Nlrp3 inflammasome and promotes tumour growth." Nature medicine 19.1 (2013): 57-64.). Compounds of the present disclosure may therefore be useful in chemotherapy to treat a range of cancers.

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e., by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) or (II) with another therapeutic agent (which also includes a therapeutic regimen) that also has therapeutic benefit.

In the instances where the compound of the present disclosure is administered in combination with other therapeutic agents, the compound of the disclosure may need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) or (II) and pharmaceutically acceptable salts thereof are also useful as pharmacological tools in the development and standardisation of in vitro and in vivo test systems for the evaluation of the effects of inhibitors of inflammasome in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

Routes of Administration

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The disclosure having been described, the following examples are offered by way of illustration and not limitation.

SPECIFIC EXAMPLES

The disclosure will now be described with reference to the following illustrative examples.

Some abbreviations that may appear in this section are defined as follows:

ACN—acetonitrile
Boc—tert-butoxy carbonyl
TFA—trifluoroacetic acid
MeOH—methanol
HCl—hydrochloride acid
DCM—dichloromethane
TLC—thin layer chromatography
DMSO—dimethyl sulfoxide
HPLC—high performance liquid chromatography
EtOAc—ethyl acetate
FCC—flash column chromatography
THF—tetrahydrofuran
NaOH—sodium hydroxide
UPLC—ultra performance liquid chromatography
Ar—argon
SM—starting material
LC-MS—liquid chromatography-mass spectrometry
$Et_3N$—triethylamine
RM—reaction mixture
eq.—equivalents
rt—room temperature/ambient temperature
h—hours
$Pd_2(dba)_3$—Tris(dibenzylideneacetone)dipalladium(O)
$Me_4tBuXPhos$—methanesulfonato(2-di-tert-butylphosphino-3,4,5,6 tetra methyl-2',4',6'-triisopropyl-1,1-biphenyl)(2'-amino-1,1'-biphenyl-2-yl) palladium(II)
HPLC—high performance liquid chromatography The compounds of the present disclosure can be prepared according to the procedures of the following Schemes and Examples, using appropriate materials and are further exemplified by the following specific examples. Analytical data of compounds made according to the following examples are shown. Unless otherwise specified, all starting materials are obtained from commercial suppliers and used without further purifications. Unless otherwise specified, all temperatures are expressed in ° C. and all reactions are conducted at rt. Compounds are typically purified by silica chromatography, preparative thin-layer chromatography or preparative HPLC.

$^1$H NMR is recorded on 400 MHz spectrometers. Chemical shifts (δ) are reported in ppm relative to the residual solvent signal (δ=2.5 ppm for $^1$H NMR in DMSO-d6). $^1$H NMR data are reported as follows: chemical shift (multiplicity, coupling constants and number of hydrogens). Multiplicity is abbreviated as follows: s (singlet), d (doublet), t (triplet) and m (multiplet).

LC-MS Analyses

UPLC-MS:

Equipment: Shimadzu LC-MS 2020 column: Waters Acquity UPLC HSS C18, 50 mm×2.1 mm×1.8 μm Eluents:
(A) 0.1% formic acid in ACN
(B) 0.1% formic acid in water Autosampler: injection volume: 1 μl Pump:

| Time [min] | Flow [mL/min] | % B |
| --- | --- | --- |
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

Column compartment: column temperature: 25° C., time of analysis: 6 min

Detector: wavelength: 200-300 nm (254, 230, 270, 280 nm)

HPLC-MS:

Equipment: MS Bruker Amazon SL; LC Dionex Ultimate 3000; HPLC with UV-Vis or DAD detector column: Kinetex XB C18 4.6×50 mm 2.6 am Eluents:
(A) 0.1% formic acid-water solution
(B) 0.1% formic acid—ACN solution Autosampler: injection volume: 1 μl Pump: flow: 0.5 ml/min

| Time [min] | [%] B |
| --- | --- |
| 0.0 | 20 |
| 6.7 | 80 |
| 7.5 | 80 |
| 7.8 | 95 |
| 9.5 | 95 |
| 10.0 | 20 |
| 12.0 | 20 |

Column compartment: column temperature: 25° C., time of analysis: 12 min

Detector: wavelength 200-300 nm (220, 254, 280 nm)

General Procedures:

General Procedure A

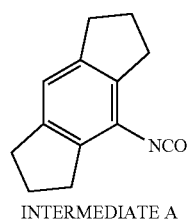

INTERMEDIATE A

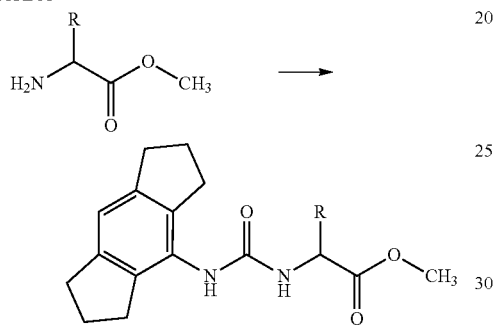

To a stirred solution of amino ester (or amino ester hydrochloride with 1 eq. of Et₃N) in ACN was added dropwise a solution of intermediate A in ACN. The RM was stirred overnight then filtered. The resulting precipitate was washed with ACN and dried under reduced pressure to give the desired product.

General Procedure B

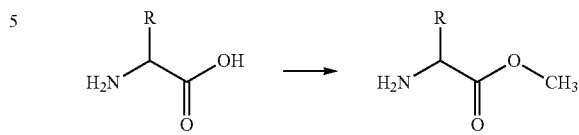

To a 0° C. cooled solution of methanol was added dropwise thionyl chloride (20 eq.) and the RM stirred at 0° C. for 30 min. The amino acid was added and the RM stirred at ambient temperature overnight. The RM was evaporated under reduced pressure to give the desired product.

General Procedure C

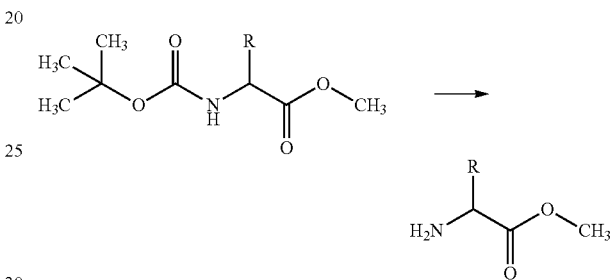

To a solution of the Boc protected starting material in MeOH was added dropwise 4 M HCl in dioxane (20 eq.). The reaction mixture was stirred until the starting material was no longer visible on TLC and then evaporated to give the desired product.

Intermediates:

The following intermediates were prepared as follows:

Intermediate A 4-isocyanato-1,2,3,5,6,7-hexahydro-s-indacene (Intermediate A)

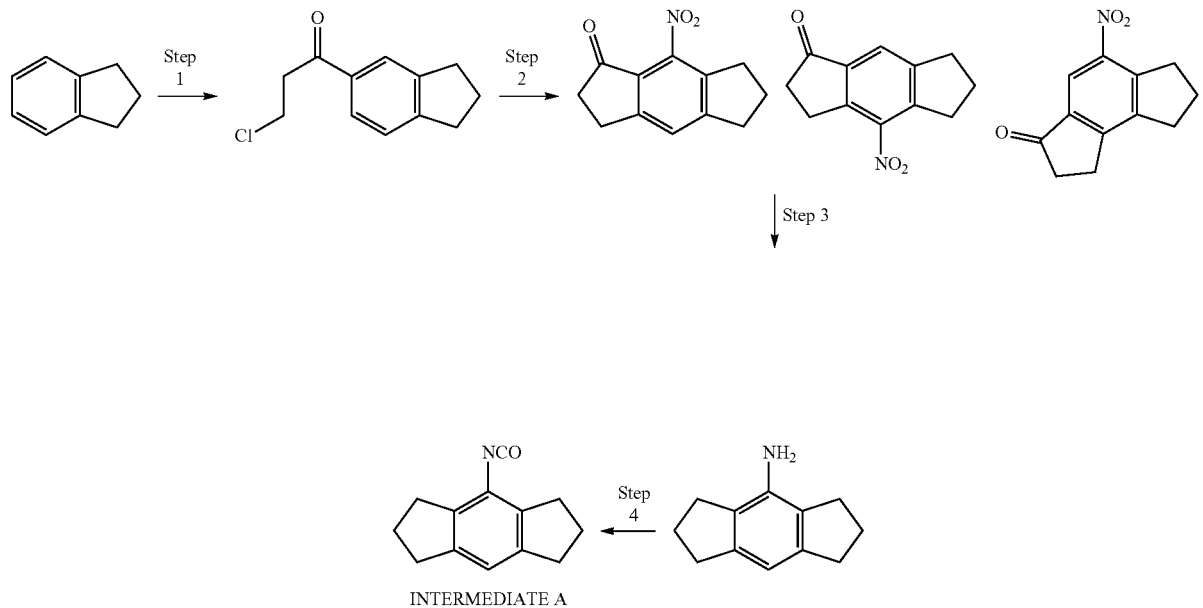

INTERMEDIATE A

Step 1

3-chloro-1-(2,3-dihydro-1H-inden-5-yl)propan-1-one

A suspension of aluminium chloride (12.4 g, 0.093 mol) in DCM (50 ml) under an argon atmosphere was cooled to −10° C. with vigorous stirring. To this was added dropwise a solution of 3-chloropropionyl chloride (11 g, 0.093 mol) and indan (10 g, 0.085 mol) in DCM (15 ml) over 0.5 h, the temperature was kept between −15° C. and −5° C. The reaction was allowed to warm to rt and stirred overnight. The reaction mixture was added dropwise to cold (0° C.) 2 M HCl over 30 min with the temperature kept between 0° C. and 10° C. The layers were separated and the aqueous phase washed with DCM (3×30 ml). The combined organic layers were washed sequentially with water, saturated sodium bicarbonate and brine. The organic phases were dried over $Na_2SO_4$, filtered and evaporated under reduced pressure to around 30 ml. Hexane (50 ml) was added and the evaporation continued, the procedure was repeated twice. After further addition of hexane (50 ml) the slurry was filtered and dried to provide 3-chloro-1-(2,3-dihydro-1H-inden-5-yl)propan-1-one as a tan solid.

Y=81%

MS ES⁺: not ionised

¹H NMR (400 MHz, DMSO-d6) δ 7.84 (d, 1H), 7.78-7.76 (m, 1H), 7.37 (d, J=8 Hz, 1H), 3.92 (t, J=6 Hz, 2H), 3.51 (t, J=6 Hz, 2H), 2.92 (t, J=8 Hz, 4H), 2.09-2.01 (m, 2H).

Step 2

Mixture of 8-nitro-1,2,3,5,6,7-hexahydro-s-indacen-1-one, 4-nitro-1,2,3,5,6,7-hexahydro-s-indacen-1-one and 5-nitro-1,2,3,6,7,8-hexahydroas-indacen-3-one 3-chloro-1-(2,3-dihydro-1H-inden-5-yl)propan-1-one (82 g, 0.39 mol) was added portion wise to concentrated sulfuric acid (71 ml, 1.34 mol). The resulting mixture was heated to 60° C. for 2 days. The RM was cooled to 0° C. and a mixture of nitric acid (26 ml, 0.59 mol) and sulfuric acid (26 ml, 0.49 mol) was added dropwise. The RM was stirred at a temperature between 0° C. and 5° C. for 1 h. The RM was slowly added to a mixture of water and DCM with ice bath cooling. The layers were separated and the aqueous layer was extracted with DCM. The combined organic layers were washed sequentially with brine and saturated sodium bicarbonate. The organic layers were dried over $Na_2SO_4$ and filtered. The crude mixture was purified by FCC (hexane/ethyl acetate). The products were further purified by crystallisation from MeOH to give the desired products.

8-nitro-1,2,3,5,6,7-hexahydro-s-indacen-1-one

Y=36%

MS ES⁺: 218

¹H NMR (400 MHz, DMSO-d6) δ 7.67 (s, 1H), 3.15-3.08 (m, 2H), 3.04 (t, J=8 Hz, 2H), 2.90 (t, J=8 Hz, 2H), 2.77-2.71 (m, 2H), 2.17-2.10 (m, 2H).

4-nitro-1,2,3,5,6,7-hexahydro-s-indacen-1-one

Y=5%

MS ES⁺: 218

¹H NMR (400 MHz, DMSO-d6) δ 7.82 (s, 1H), 3.41-3.36 (m, 2H), 3.34-3.29 (m, 3H), 3.02 (t, J=8 Hz, 2H), 2.77-2.69 (m, 2H), 2.17-2.10 (m, 2H).

5-nitro-1,2,3,6,7,8-hexahydroas-indacen-3-one

Y=4%

MS ES⁺: 218

¹H NMR (400 MHz, DMSO-d6) δ 8.09 (s, 1H), 3.39 (t, J=8 Hz, 2H), 3.14-3.09 (m, 2H), 3.01 (t, J=8 Hz, 2H), 2.81-2.73 (m, 2H), 2.23-2.15 (m, 2H).

Step 3

1,2,3,5,6,7-hexahydro-s-indacen-4-amine

A mixture of 8-nitro-1,2,3,5,6,7-hexahydro-s-indacen-1-one and 4-nitro-1,2,3,5,6,7-hexahydro-s-indacen-1-one (7.00 g, 0.032 mol) was suspended in MeOH (70 ml). This was treated with 20% palladium hydroxide on carbon (50% water wet. 1.72 g, 0.012 mol) then methanesulfonic acid (3.41 g, 0.035 mol). The mixture was hydrogenated at 35 psi for 5 h. The catalyst was removed by filtration and washed with MeOH. The filtrate was diluted with water (350 ml) and then the pH adjusted to 11 with 2 N NaOH. The resulting slurry was filtered and the crude solids were recrystallised from MeOH/water (9:1) to afford of 1,2,3,5,6,7-hexahydro-s-indacen-4-amine as colourless, crystal needles.

Y=73%

MS ES⁺: 174.1

¹H NMR (400 MHz, DMSO-d6) δ 6.35 (s, 1H), 4.52 (s, 2H), 2.72 (t, J=7 Hz, 4H), 2.59 (t, J=7 Hz, 4H), 2.00-1.93 (m, 4H).

Step 4

4-isocyanato-1,2,3,5,6,7-hexahydro-s-indacene (Intermediate A)

To a stirred solution of 1,2,3,5,6,7-hexahydro-s-indacen-4-amine (1.1 g, 6.35 mmol) and Et₃N (0.973 ml, 6.98 mmol) in THF (20 ml) was added triphosgene (0.64 g, 2.16 mmol) in one portion. The mixture was heated to reflux for 4 h then cooled to rt. The THF was evaporated and the residue taken up in pentane and filtered through a plug of silica gel. Evaporation of the solvent in vacuo afforded 4-isocyanato-1,2,3,5,6,7-hexahydro-s-indacene as a white solid.

Y=71%

MS ES⁺: not ionised

¹H NMR (400 MHz, Chloroform-d) δ 6.96 (s, 1H), 2.94-2.89 (m, 8H), 2.22-2.03 (m, 4H).

Intermediate B

Ethyl 1H,2H,3H,6H,7H,8H,9H-cyclopenta[a]naphthalen-5-amine (Intermediate B)

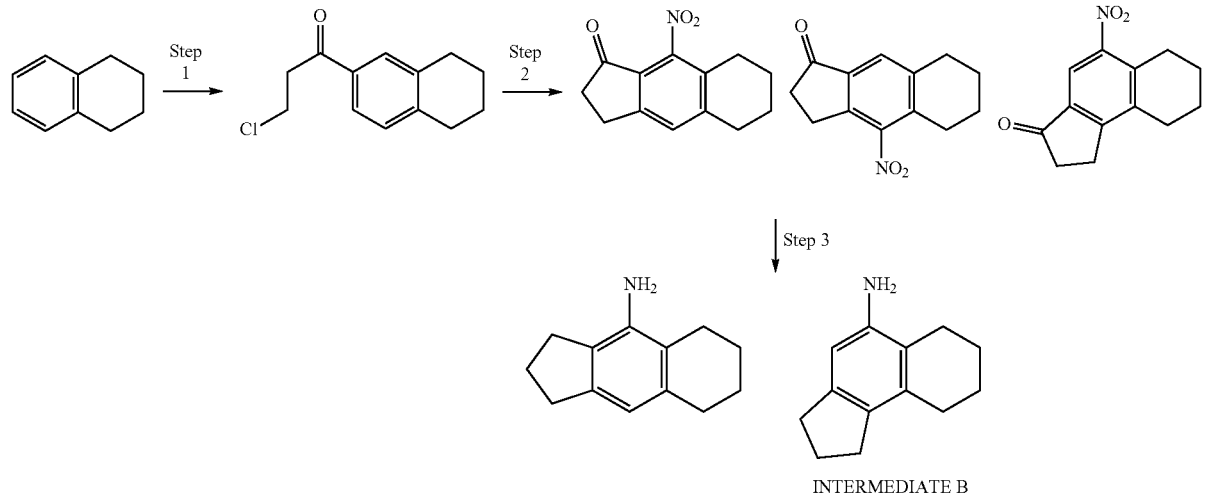

INTERMEDIATE B

Step 1

3-chloro-1-(5,6,7,8-tetrahydronaphthalen-2-yl)propan-1-one

A suspension of aluminium chloride (5.58 g, 0.042 mol) in DCM (30 ml) under an argon atmosphere was cooled to −10° C. with vigorous stirring. To this was added dropwise a solution of 3-chloropropionyl chloride (3.6 ml, 0.038 mol) and tetralin (5 g, 0.038 mol) in DCM (10 ml) over 0.5 h, the temperature was kept between −15° C. and −5° C. The reaction was allowed to warm to rt and stirred overnight. The reaction mixture was added dropwise to cold (0° C.) 2 M HCl over 30 min with the temperature kept between 0° C. and 10° C. The layers were separated and the aqueous phase washed with DCM (3×20 ml). The combined organic layers were washed sequentially with water, saturated sodium bicarbonate and brine. The organic phases were dried over $Na_2SO_4$, filtered and evaporated under reduced pressure to provide 3-chloro-1-(2,3-dihydro-1H-inden-5-yl)propan-1-one as a yellow solid.

Y=91%
MS ES$^+$: not ionised
$^1$H NMR (400 MHz, DMSO-d6) δ 7.84 (d, 1H), 7.69-7.66 (m, 2H), 7.20 (d, J=8 Hz, 1H), 3.91 (t, J=6 Hz, 2H), 3.49 (t, J=6 Hz, 2H), 2.78 (d, J=4 Hz, 4H), 1.77-1.72 (m, 4H).

Step 2

Mixture of 9-nitro-1H,2H,3H,5H,6H,7H,8H-cyclopenta[b]naphthalen-1-one, 4-nitro-1H,2H,3H,5H,6H,7H,8H-cyclopenta[b]naphthalen-1-one and 5-nitro-1H,2H,3H,6H,7H,8H,9H-cyclopenta[a]naphthalen-3-one 3-chloro-1-(5,6,7,8-tetrahydronaphthalen-2-yl)propan-1-one (7.52 g, 34 mmol) was added portion wise to concentrated sulfuric acid (36 ml). The resulting mixture was heated to 60° C. for 2 days. The RM was cooled to 0° C. and a mixture of nitric acid (2.4 ml, 52 mmol) and sulfuric acid (2.4 ml) was added dropwise. The RM was stirred at a temperature between 0° C. and 5° C. for 1 h. The RM was slowly added to a mixture of water and DCM with ice bath cooling. The layers were separated and the aqueous layer was extracted with DCM. The combined organic layers were washed sequentially with brine and saturated sodium bicarbonate. The organic layers were dried over $Na_2SO_4$ and filtered. The crude mixture was purified by FCC (hexane/ethyl acetate) to provide a mixture of 9-nitro-1H,2H,3H,5H,6H,7H,8H-cyclopenta[b]naphthalen-1-one, 4-nitro-1H,2H,3H,5H,6H,7H,8H-cyclopenta[b]naphthalen-1-one and 5-nitro-1H,2H,3H,6H,7H,8H,9H-cyclopenta[a]naphthalen-3-one as a yellow semisolid.

Y=13%
MS ES$^+$: 232

Step 3

1H,2H,3H,6H,7H,8H,9H-cyclopenta[a]naphthalen-5-amine (Intermediate B)

A Mixture of 9-nitro-1H,2H,3H,5H,6H,7H,8H-cyclopenta[b]naphthalen-1-one, 4-nitro-1H,2H,3H,5H,6H,7H,8H-cyclopenta[b]naphthalen-1-one and 5-nitro-1H,2H,3H,6H,7H,8H,9H-cyclopenta[a]naphthalen-3-one (0.992 g, 2.3 mmol) was suspended in MeOH (40 ml). This was treated with 20% palladium hydroxide on carbon (50% water wet. 0.389 g, 0.21 mmol) then methanesulfonic acid (0.32 ml, 4.8 mmol). The mixture was hydrogenated at 35 psi overnight. The catalyst was removed by filtration and washed with MeOH. The filtrate was diluted with water (50 ml) and then the pH adjusted to 11 with 2 M NaOH. The resulting slurry was filtered and the crude solids were purified by FCC (hexane/ethyl acetate) to provide 1H,2H,3H,6H,7H,8H,9H-cyclopenta[a]naphthalen-5-amine as a brown oil.

Y=19%
MS ES$^+$: 188.4
$^1$H NMR (400 MHz, DMSO-d6) δ 6.35 (s, 1H), 4.42 (s, 2H), 2.69 (t, J=8 Hz, 2H), 2.58 (t, J=7 Hz, 2H), 2.48 (t, J=6 Hz, 2H), 2.32 (t, J=6 Hz, 2H), 1.95-1.88 (m, 2H), 1.76-1.60 (m, 4H).

Certain of the intermediates defined herein may be novel and these may be provided as a further feature of the disclosure.

Additional Starting Materials

The starting materials for the preparation of compounds of the present disclosure can be prepared by methods as described in the examples or by methods known per se, as described in the literature of synthetic organic chemistry and known to the skilled person, or can be obtained commercially. The starting materials for the processes may, if desired, also be formed in situ by not isolating them from the reaction mixture, but instead immediately converting them further into the compounds of the disclosure or intermediate compounds. On the other hand, in general it is possible to carry out the reaction stepwise.

The following additional starting materials were used in the production of the compounds of the disclosure and their method of production is included below:

Methyl 2-amino-3-(2-hydroxyphenyl)propanoate Hydrochloride

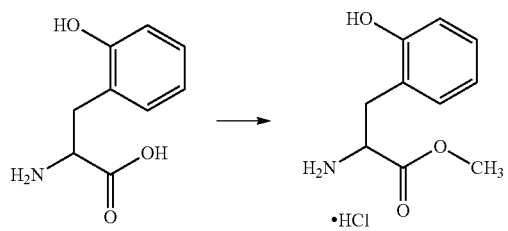

SM: 2-amino-3-(2-hydroxyphenyl)propanoic acid

General Procedure B

The product was taken on to the next step without further purification.

MS ES+: 196

1-[3-(bromomethyl)phenyl]ethan-1-one

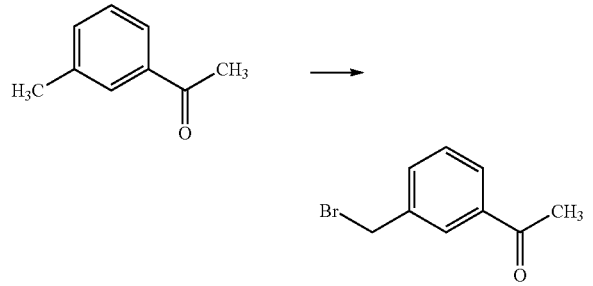

A solution of meta-tolylethanone (5 g, 37 mmol), N-bromosuccinimide (1 eq, 6.6 g, 37 mmol) and benzoic peroxyanhydride (0.2 eq, 1.8 g, 7.5 mmol) in acetonitrile was stirred at 85° C. under argon overnight. The solvent was removed under reduced pressure. The residue was purified by FCC (EtOAc in Hexane 0-5%) to give the desired product as a yellow oil.

Y=58%

MS ES+: not ionised $^1$H NMR (400 MHz, Chloroform-d) δ 8.00 (t, J=2 Hz, 1H), 7.94-7.88 (m, 1H), 7.65-7.59 (m, 1H), 7.48 (t, J=8 Hz, 1H), 4.56 (s, 2H), 2.64 (s, 3H).

1,3-diethyl 2-[(3-acetylphenyl)methyl]-2-acetamidopropanedioate

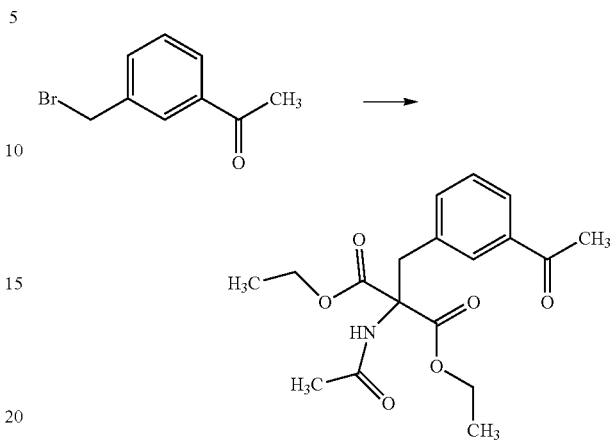

A suspension of 1-[(3-bromomethyl)phenyl]ethan-1-one (2.5 g, 11.7 mmol), diethyl acetamidomalonate (1 eq, 2.55 g, 11.7 mmol), K$_2$CO$_3$ (1.2 eq, 1.95 g, 14.1 mmol), potassium iodide (0.25 eq, 487 mg, 2.9 mmol) and Cs$_2$CO$_3$ (1.2 eq, 4.59 g, 14.1 mmol) in acetonitrile (100 ml) was heated to reflux and stirred overnight. The reaction mixture was cooled to room temperature, filtered through a pad of Celite and concentrated in vacuo. Purification by FCC (EtOAc in Hexane 0-50%) gave the desired product as a white solid.

Y=67%

MS ES+: 350.0

3-(3-Acetylphenyl)-2-aminopropanoic Acid Hydrochloride

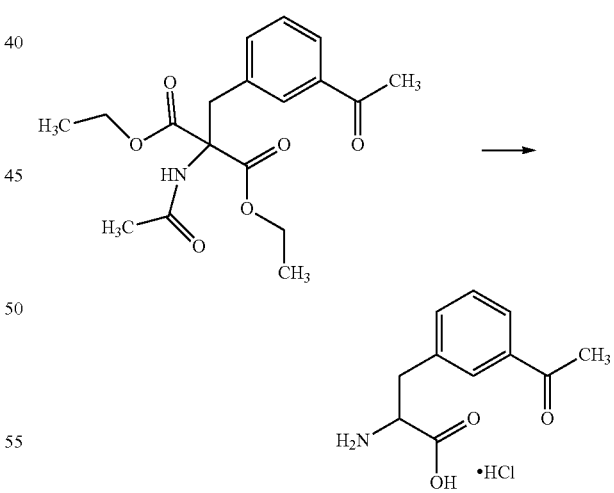

A suspension of 1,3-diethyl 2-[(3-acetylphenyl)methyl]-2-acetamidopropanedioate (2.74 g, 7.84 mmol) in 6 M HCl (80 ml) was heated to reflux for 16 h. The reaction mixture was allowed to cool to room temperature. The solvent was evaporated and the solid filtered, washed thrice with diethyl ether and dried in vacuo to afford the corresponding product as a white solid.

Y=98%

MS ES-: 207.0

Methyl 3-(3-acetylphenyl)-2-aminopropanoate

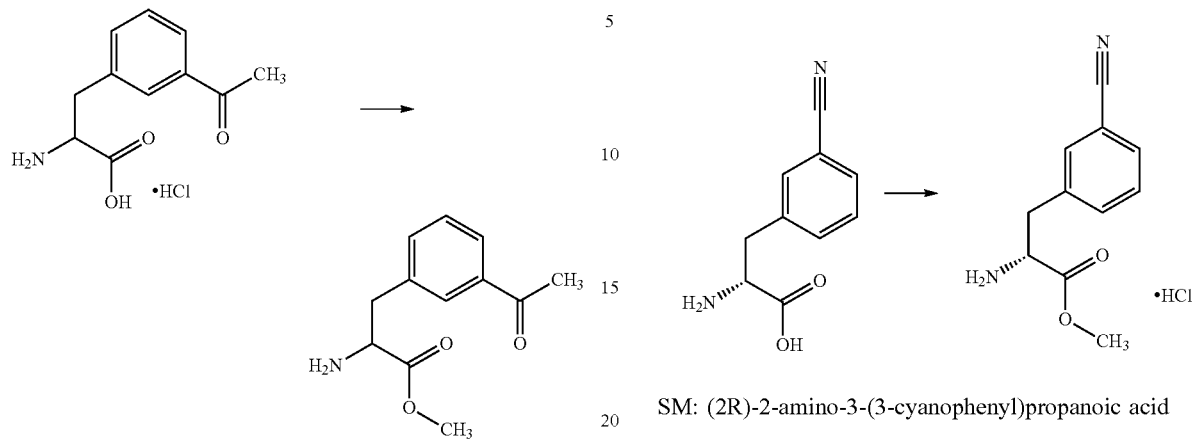

SM: 3-(3-Acetylphenyl)-2-aminopropanoic acid hydrochloride

General Procedure B

The product was further purified by FCC (0-7% MeOH in DCM) to give the desired product as a white solid.
Y=8%
MS ES+: 222.0

Methyl (2R)-2-amino-3-(4-cyanophenyl)propanoate

SM: (2R)-2-amino-3-(4-cyanophenyl)propanoic acid

General Procedure B

The product was additionally partitioned in pH=8-9 water and EtOAc, separated and the organics dried (Na$_2$SO$_4$) and concentrated. Further purification by by FCC (DCM/MeOH) gave the desired product.
Y=63%
MS ES+: 205

Methyl (2R)-2-amino-3-(3-cyanophenyl)propanoate Hydrochloride

SM: (2R)-2-amino-3-(3-cyanophenyl)propanoic acid

General Procedure B

Y=67%
MS ES+: 205

Methyl 2-amino-3-(3-bromophenyl)propanoate

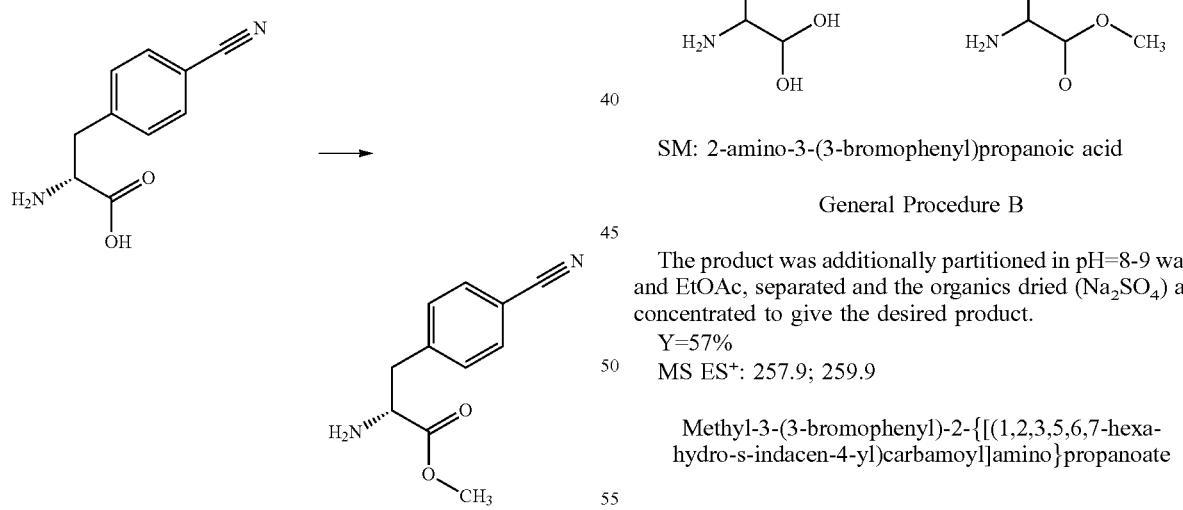

SM: 2-amino-3-(3-bromophenyl)propanoic acid

General Procedure B

The product was additionally partitioned in pH=8-9 water and EtOAc, separated and the organics dried (Na$_2$SO$_4$) and concentrated to give the desired product.
Y=57%
MS ES+: 257.9; 259.9

Methyl-3-(3-bromophenyl)-2-{[(1,2,3,5,6,7-hexahydro-s-indacen-4-yl)carbamoyl]amino}propanoate

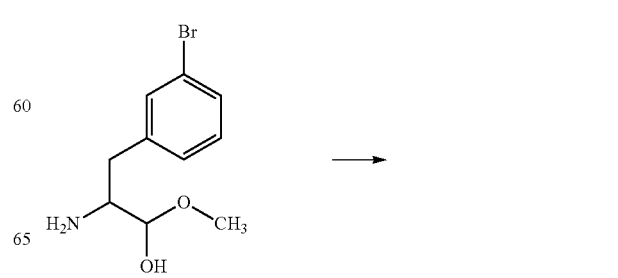

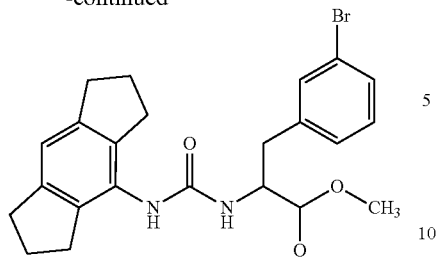

SM: methyl 2-amino-3-(3-bromophenyl)propanoate

General Procedure A

Y=74%

MS ES+: 457; 459

1H NMR (400 MHz, DMSO-d6) δ 7.83 (s, 1H), 7.47-7.42 (m, 1H), 7.42-7.38 (m, 1H), 7.27 (t, J=8 Hz, 1H), 7.23-7.18 (m, 1H), 6.87 (s, 1H), 6.40 (d, J=8 Hz, 1H), 4.53-4.48 (m, 1H), 3.66 (s, 3H), 3.11-3.07 (m, 1H), 2.99-2.93 (m, 1H), 2.79 (t, J=7 Hz, 4H), 2.63 (t, J=7 Hz, 4H), 1.98-1.91 (m, 4H).

Methyl (2R)-2-amino-3-(pyridin-3-yl)propanoate Hydrochloride

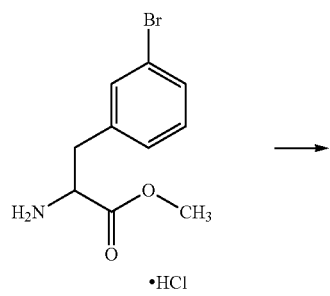

SM: 3-(3-pyridyl)-D-alanine

General Procedure B

Y=63%

MS ES+: 181.0

Methyl 3-(3-bromophenyl)-2-{[(tert-butoxy)carbonyl]amino}propanoate

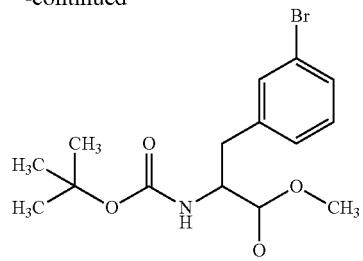

Methyl 2-amino-3-(3-bromophenyl)propanoate hydrochloride (550 mg, 1.867 mmol) and Et₃N (0.520 ml, 1.2 eq., 3.734 mmol) were dissolved in dioxane (25 ml). To this was added dropwise a solution of di-tert-butyl dicarbonate (489 mg, 2 eq., 2.240 mmol) in dioxane (25 ml). The RM was stirred at room temperature until the starting material was no longer observed on TLC. The crude product was purified by FCC (hexane/EtOAc) to give the desired product.

Y=60%

MS ES+: does not ionise

Methyl 2-{[(tert-butoxy)carbonyl]amino}-3-[3-(1H-pyrazol-3-yl)phenyl]propanoate

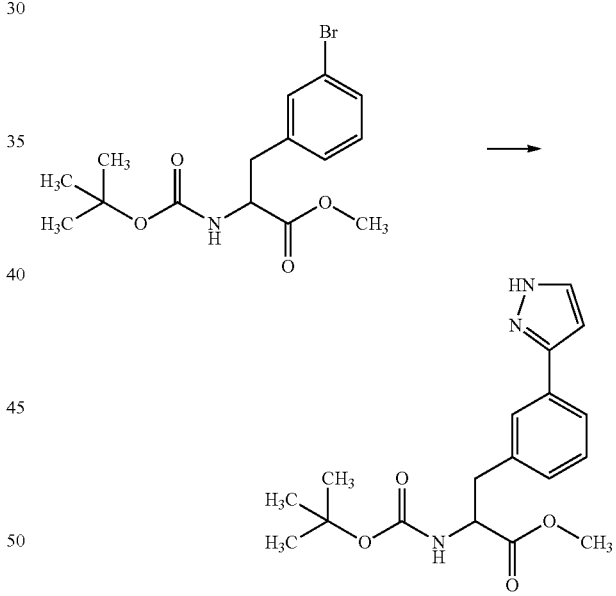

Methyl 3-(3-bromophenyl)-2-{[(tert-butoxy)carbonyl] amino}propanoate (100 mg, 0.28 mmol), (1H-pyrazol-3-yl) boronic acid (47 mg, 1.5 eq., 0.42 mmol), [1,1'-bis(diphenylphosphino)ferrocene]dichloropalladium(II) (12 mg, 0.05 eq., 0.014 mmol) and Na₂CO₃ (89 mg, 3 eq., 0.837 mmol) were dissolved in ACN (2 ml) with one drop of water. The RM was irradiated in a microwave reactor at 90° C. for 1 h. The crude reaction mixture was filtered through Celite, washed with MeOH and concentrated under reduced pressure. The crude product was purified by FCC (DCM/MeOH) to give the desired product.

Y=26%

MS ES+: 346

Methyl 2-amino-3-[3-(1H-pyrazol-5-yl)phenyl]propanoate Hydrochloride

(2R)-3-(3-bromophenyl)-2-{[(tert-butoxy)carbonyl]amino}propanoate

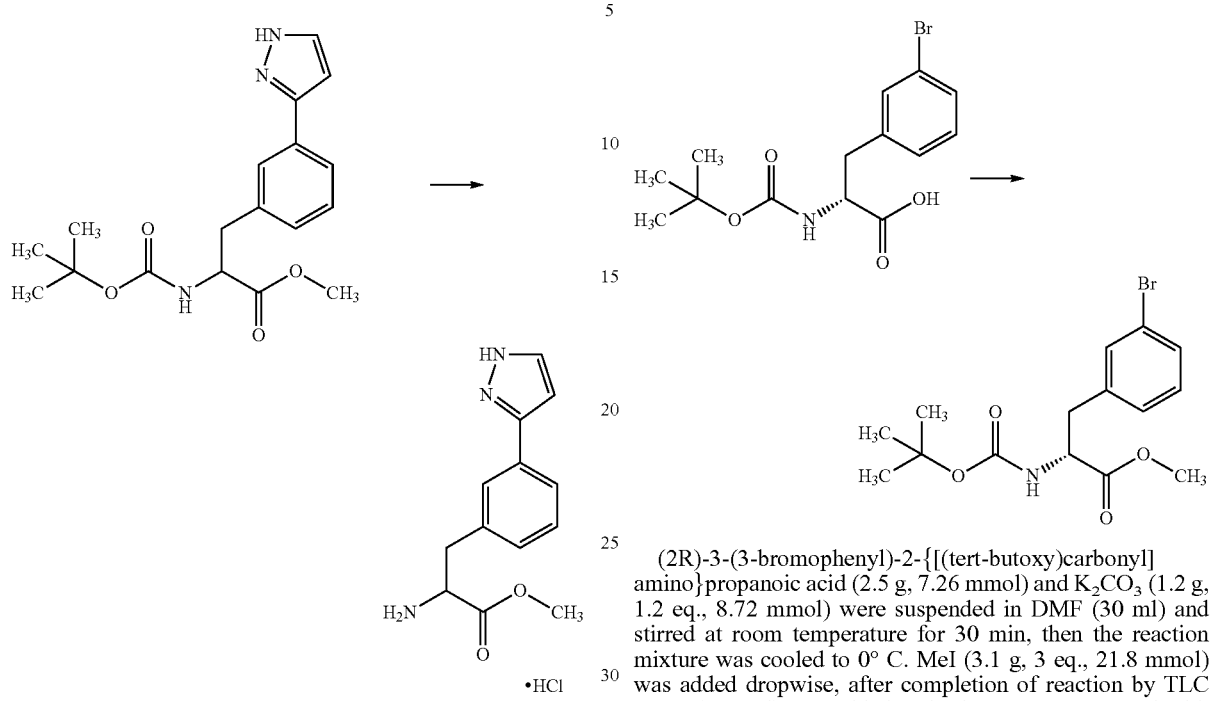

SM: methyl 2-{[(tert-butoxy)carbonyl]amino}-3-[3-(1H-pyrazol-3-yl)phenyl]propanoate General Procedure C The crude product was taken on to the next step without further purification.

(2R)-3-(3-bromophenyl)-2-{[(tert-butoxy)carbonyl]amino}propanoic acid (2.5 g, 7.26 mmol) and $K_2CO_3$ (1.2 g, 1.2 eq., 8.72 mmol) were suspended in DMF (30 ml) and stirred at room temperature for 30 min, then the reaction mixture was cooled to 0° C. MeI (3.1 g, 3 eq., 21.8 mmol) was added dropwise, after completion of reaction by TLC water (150 ml) was added and mixture was extracted with $Et_2O$. The organic phase was evaporated to give the desired product.

Y=88%

MS ES$^+$: not ionised.

$^1$H NMR (400 MHz, DMSO-d6) δ 7.46 (s, 1H), 7.43-7.40 (m, 1H), 7.33 (d, J=8 Hz, 1H), 7.28-7.22 (m, 2H), 4.23-4.17 (m, 1H), 3.63 (s, 3H), 3.05-3.00 (m, 1H), 2.87-2.81 (m, 1H), 1.33 (s, 9H).

Methyl (2R)-2-{[(tert-butoxy)carbonyl]amino}-3-[3-(1H-pyrazol-3-yl)phenyl]propanoate

Methyl (2R)-2-amino-3-(3-hydroxyphenyl)propanoate Hydrochloride

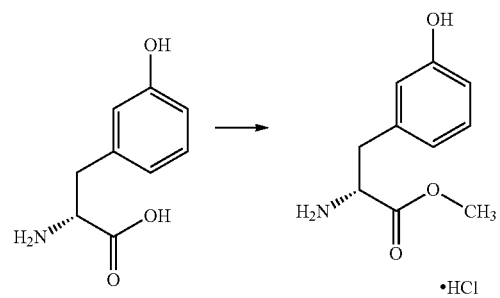

SM: (2R)-2-amino-3-(3-hydroxyphenyl)propanoic acid

General Procedure B

Y=74%

MS ES$^+$:195.9

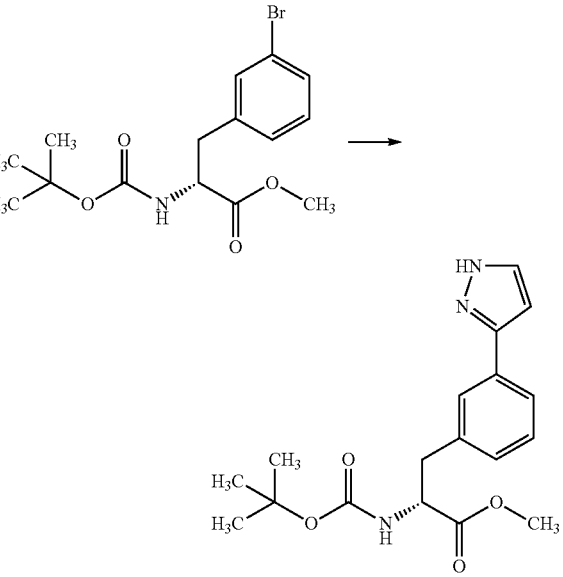

Methyl (2R)-3-(3-bromophenyl)-2-{[(tert-butoxy)carbonyl]amino}propanoate (300 mg, 0.84 mmol), (1H-pyrazol-3-yl)boronic acid (141 mg, 1.5 eq., 1.26 mmol), bis(diphenylphosphino)ferrocene]dichloropalladium(II) (34 mg, 0.05 eq., 0.042 mmol) and Na₂CO₃ (266 mg, 3 eq., 2.51 mmol) were suspended in ACN (10 ml) and water (1 ml). The RM was irradiated in a microwave reactor at 90° C. for 1 h. The RM was filtered through Celite, washed with MeOH and concentrated under reduced pressure to give the desired product, taken on to the next step without purification.

Y=76%

MS ES⁺: 246

Methyl (2R)-2-amino-3-[3-(1H-pyrazol-5-yl)phenyl]propanoate Hydrochloride

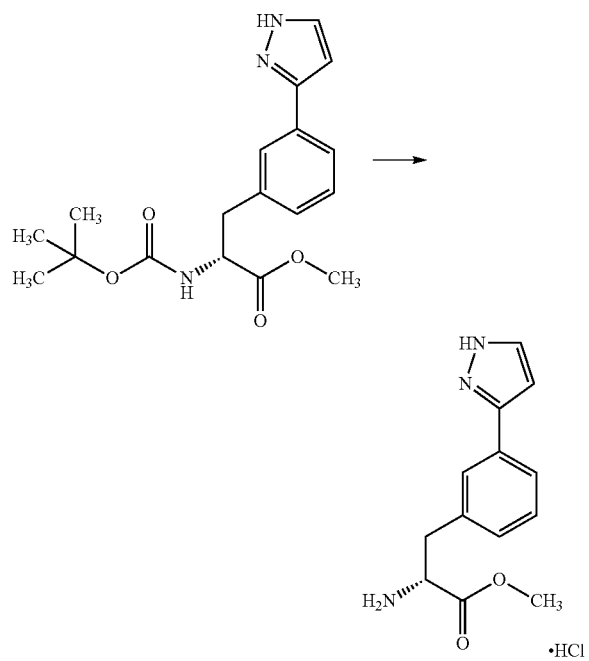

SM: Methyl (2R)-2-{[(tert-butoxy)carbonyl]amino}-3-[3-(1H-pyrazol-3-yl)phenyl]propanoate General Procedure C The crude product was taken on to the next step without purification.

Methyl (2R)-2-amino-3-(3-bromophenyl)propanoate Hydrochloride

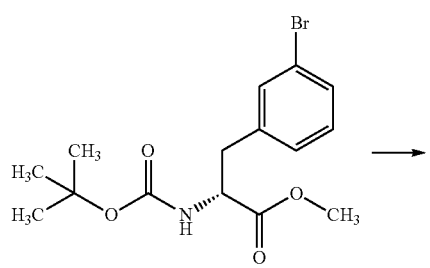

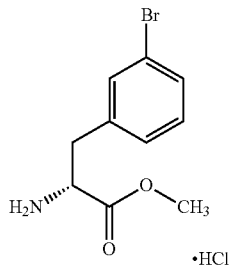

SM: methyl (2R)-3-(3-bromophenyl)-2-{[(tert-butoxy)carbonyl]amino}propanoate

General Procedure C

Crude product was taken to the next step without purification

Y=97%

MS ES⁺: 258; 260

(2R)-3-(3-bromophenyl)-2-{[(1,2,3,5,6,7-hexahydro-s-indacen-4-yl)carbamoyl]amino}propanoate

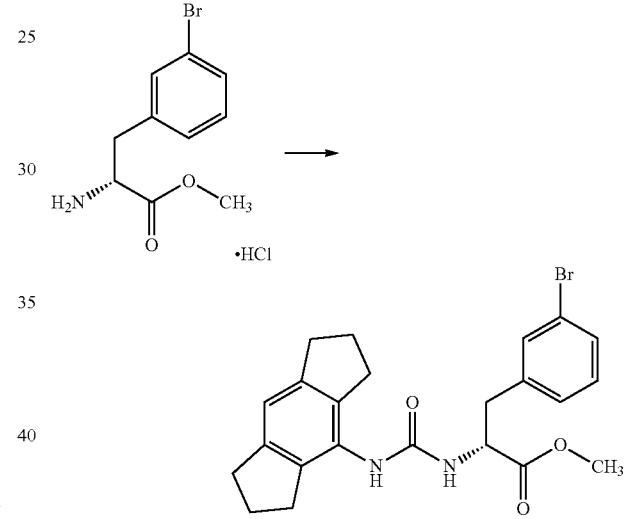

SM: methyl (2R)-2-amino-3-(3-bromophenyl)propanoate hydrochloride

General Procedure A

Y=89%

MS ES⁺: 457; 459

(2R)-3-{[(tert-butoxy)carbonyl]amino}-2-{[(1,2,3,5,6,7-hexahydro-s-indacen-4-yl) carbamoyl]amino}propanoate

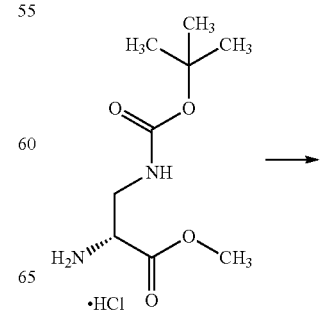

-continued

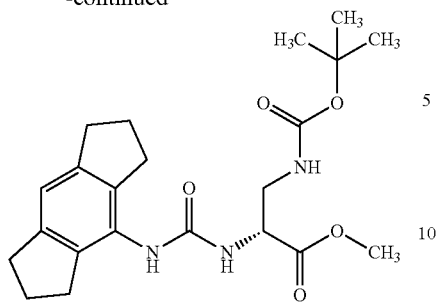

SM: methyl (2R)-2-amino-3-{[(tert-butoxy)carbonyl]amino}propanoate hydrochloride General Procedure A Y=92%
MS ES+: 418
$^1$H NMR (400 MHz, DMSO-d6) δ 7.96 (s, 1H), 6.98 (t, J=6 Hz, 1H), 6.88 (s, 1H), 6.38 (d, J=8 Hz, 1H), 4.30-4.25 (m, 1H), 3.63 (s, 3H), 3.27 (t, J=6 Hz, 2H), 2.79 (t, J=7 Hz, 4H), 2.74-2.64 (m, 4H), 1.99-1.92 (m, 4H), 1.38 (s, 9H).

Methyl (2R)-2-{[(tert-butoxy)carbonyl]amino}-3-(3-acetamidophenyl)propanoate

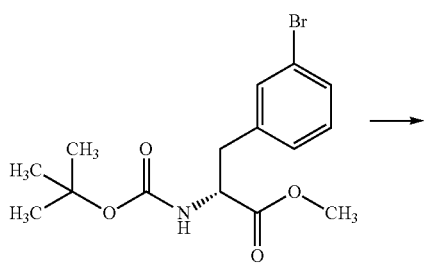

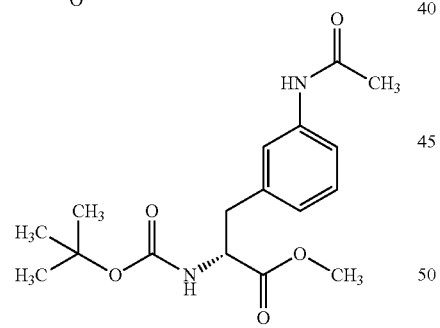

A microwave vial was charged with (2R)-3-(3-bromophenyl)-2-{[(tert-butoxy)carbonyl]amino}propanoate (50 mg, 0.14 mmol), K$_3$PO$_4$ (62 mg, 0.29 mmol, 2.1 eq.), Pd$_2$(dba)$_3$ (6 mg, 0.007 mmol, 0.05 eq.) and Me$_4$tBuXPhos (17 mg, 0.035 mmol, 0.25 eq.).

The tube was sealed, evacuated and backfilled with argon (three times). A solution of acetamide (17 mg, 2 eq., 0.28 mmol) in tert-butanol (5 ml) was added to the tube. The RM was stirred at 110° C. for 24 h. The reaction mixture was filtered through Celite, washed with MeOH and concentrated under reduced pressure. The crude product was purified by FCC to obtain the desired product.
Y=27%
MS ES+: 337

Methyl (2R)-2-amino-3-(3-acetamidophenyl)propanoate Hydrochloride

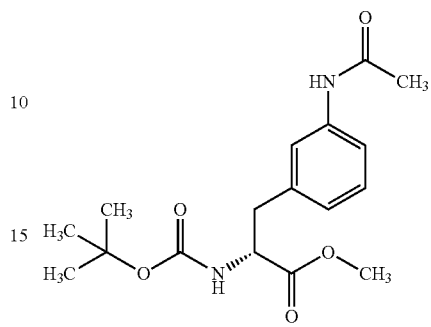

SM: methyl (2R)-2-{[(tert-butoxy)carbonyl]amino}-3-(3-acetamidophenyl)propanoate General Procedure C The crude product was taken on to the next step without purification.

Methyl amino-3-(1-methyl-1H-pyrazol-4-yl)propanoate Dihydrochloride

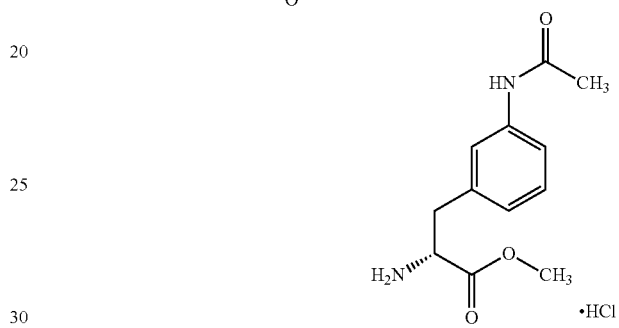

SM: 2-amino-3-(1-methyl-1H-pyrazol-4-yl)propanoic acid

General Procedure B

The product was taken on to the next step without purification.
Y=94%
MS ES+: 184

45

Methyl(2R)-2-{[(tert-butoxy)carbonyl]amino}-3-[3-(2-oxopyrrolidin-1-yl)phenyl]propanoate

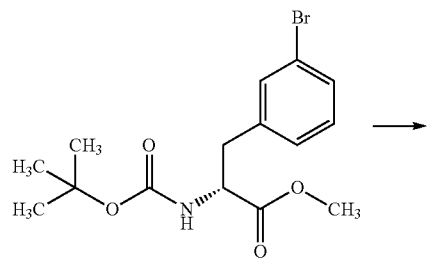

A microwave vial was charged with (2R)-3-(3-bromophenyl)-2-{[(tert-butoxy)carbonyl]amino}propanoate (50 mg, 0.14 mmol), K$_3$PO$_4$ (62 mg, 0.293 mmol, 2.1 eq.), Pd$_2$(dba)$_3$ (6 mg, 0.007 mmol, 0.05 eq.) and Me$_4$tBuXPhos (17 mg, 0.035 mmol, 0.25 eq.). The tube was sealed, evacuated and backfilled with argon (three times). To this was added a solution of pyrrolidone (23 mg, 0.28 mmol, 2 eq.) in tert-butanol (5 ml). The RM was stirred at 110° C. for 24 h. The RM was filtered through Celite, washed with MeOH and concentrated under reduced pressure to give the desired product, taken on to the next step without purification.
Y=59%
MS ES$^+$: 363

Methyl (2R)-2-amino-3-{3-[(2-oxocyclopentyl)amino]phenyl}propanoate

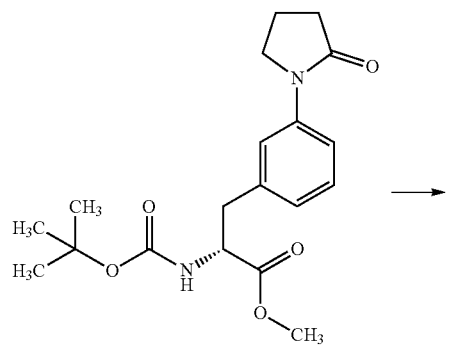

46

SM: methyl(2R)-2-{[(tert-butoxy)carbonyl]amino}-3-[3-(2-oxopyrrolidin-1-yl)phenyl]propanoate General Procedure C The crude product was taken on to the next step without purification.

3-(1,2,3,5,6,7-hexahydro-s-indacen-4-yl)-5-({3-[(1H-pyrazol-3-yl)amino]phenyl}methyl)imidazolidine-2,4-dione

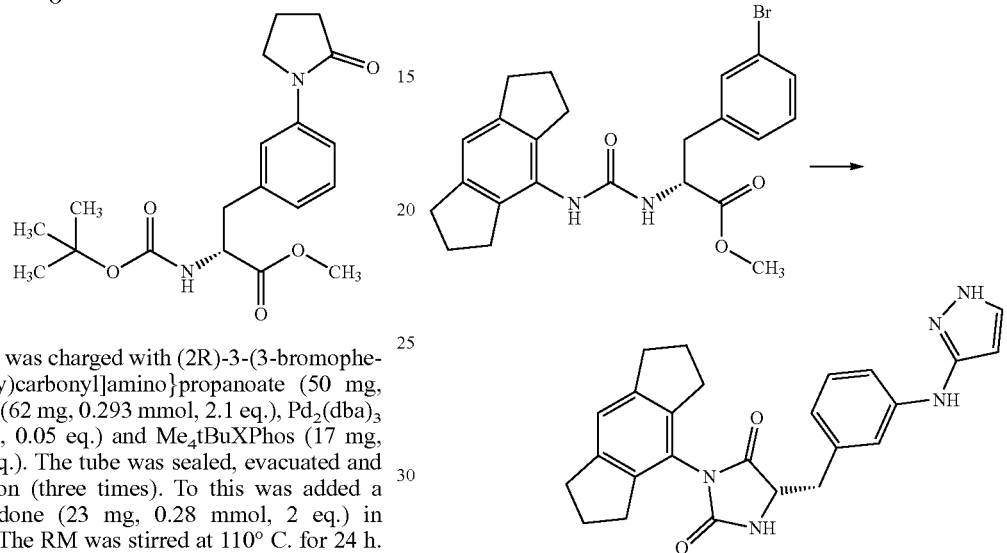

A sealed tube was charged with methyl (2R)-3-(3-bromophenyl)-2-{[(1,2,3,5,6,7-hexahydro-s-indacen-4-yl)carbamoyl]amino}propanoate (75 mg, 0.139 mmol), 3-aminopyrazole (14 mg, 0.164 mmol), $^t$BuONa (33 mg, 0.293 mmol, 2.1 eq.), 2-di-tert-butylphosphino-2',4',6'-triisopropylbiphenyl, tBuXPhos ligand (4 mg, 0.008 mmol, 0.05 eq.) and chloro[2-(di-tert-butylphosphino)-2',4',6'-triisopropyl-1,1'-biphenyl][2-(2-aminoethyl)phenyl]palladium(II) tBuXPhos 1G precatalyst (6 mg, 0.008 mmol, 0.05 eq.) The tube was sealed, evacuated and backfilled with argon (three times) and then tert-butanol (2 ml) was added. The RM was stirred at 110° C. for 24 h. The RM was filtered through Celite, washed with MeOH and concentrated under reduced pressure. The crude product was purified by FCC to give the desired product.
Y=85%
MS ES$^+$: 427

(2R)-2-{[(1,2,3,5,6,7-hexahydro-s-indacen-4-yl)carbamoyl]amino}-3-{3-[(1H-pyrazol-3-yl)amino]phenyl}propanoic acid

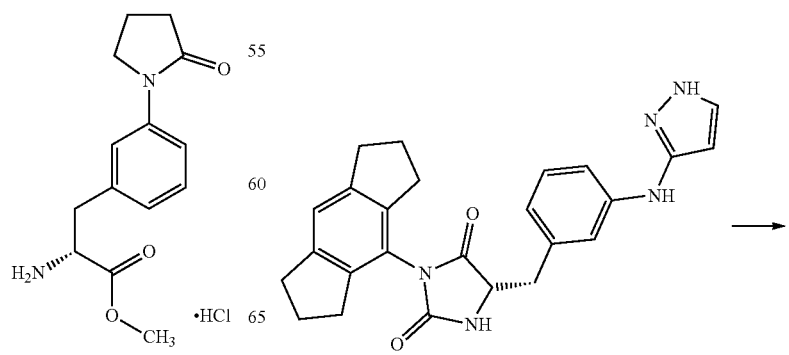

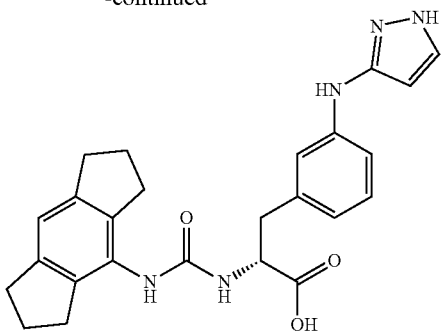

3-(1,2,3,5,6,7-hexahydro-s-indacen-4-yl)-5-({3-[(1H-pyrazol-3-yl)amino]phenyl}methyl)imidazolidine-2,4-dione (60 mg, 0.141 mmol) was suspended in 5 M NaOH (2 ml) and stirred at room temperature overnight. The RM was evaporated to give the desired product, which was taken on to the next step without purification.

Y=80%

MS ES+: 446.4

(2R)-2-amino-3-[3-(1H-pyrazol-3-yl)phenyl]propanoic Acid Dihydrochloride

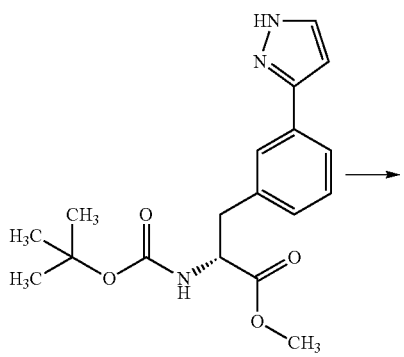

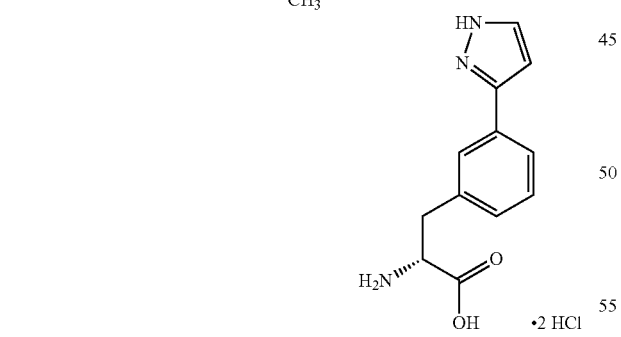

A mixture of methyl (2R)-2-{[(tert-butoxy)carbonyl]amino}-3-[3-(1H-pyrazol-3-yl)phenyl]propanoate (203 mg, 0.60 mmol) and 6 M HCl (10 ml) were heated at reflux overnight. The RM was allowed to cool to rt, diluted with water (50 ml) and washed with diethyl ether (50 ml). The aqueous phase was then evaporated under reduced pressure to give the desired product as a yellow solid.

Y=100%

MS ES+: 232.1

¹H NMR (400 MHz, DMSO-d6) δ 8.59-8.43 (m, 3H), 7.80 (d, J=2 Hz, 1H), 7.79-7.77 (m, 1H), 7.76-7.72 (m, 1H), 7.39 (t, J=8 Hz, 1H), 7.27-7.21 (m, 1H), 6.75 (d, J=2 Hz, 1H), 4.25-4.17 (m, 1H), 3.22-3.17 (m, 2H).

2-{[(1,2,3,5,6,7-hexahydro-s-indacen-4-yl)carbamoyl]amino}acetic Acid

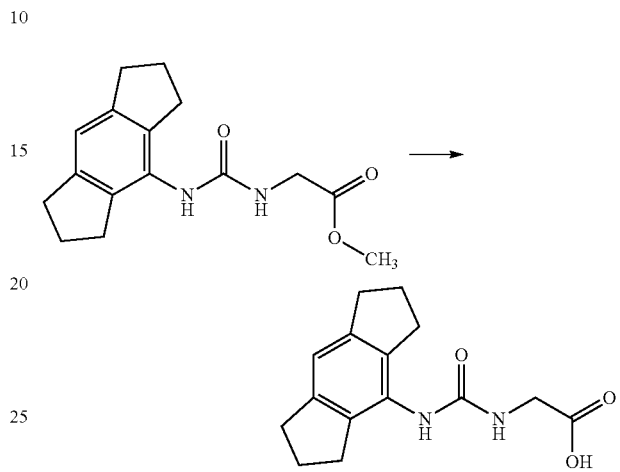

Methyl 2-{[(1,2,3,5,6,7-hexahydro-s-indacen-4-yl)carbamoyl]amino}acetate (140 mg, 0.5 mmol) was suspended in MeOH (1 ml). 1 M NaOH (5 ml) was added and the reaction mixture was stirred at room temperature overnight then concentrated in vacuo. The residue was acidified to pH 2 with 2 M HCl and the resulting precipitate was filtered and washed with water to give the desired product as a white solid.

Y=73%

MS ES+: 275.0

¹H NMR (400 MHz, DMSO) δ 12.47 (s, 1H), 7.90 (s, 1H), 6.88 (s, 1H), 6.26 (t, J=6 Hz, 1H), 3.76 (d, J=6 Hz, 2H), 2.80 (t, J=7 Hz, 4H), 2.70 (t, J=7 Hz, 4H), 2.01-1.91 (m, 4H).

Methyl (2R)-2-amino-3-methoxypropanoate Hydrochloride

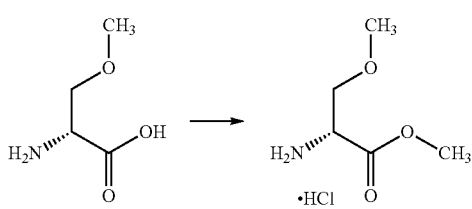

SM: (2R)-2-amino-3-methoxypropanoic acid

General Procedure B

The product was taken on to the next step without further purification.

MS ES+: 175 [M+ACN]

2-{[(Tert-butoxy)carbonyl]amino}-3-[3-(1H-pyrazol-3-yl)phenyl]propanoic Acid

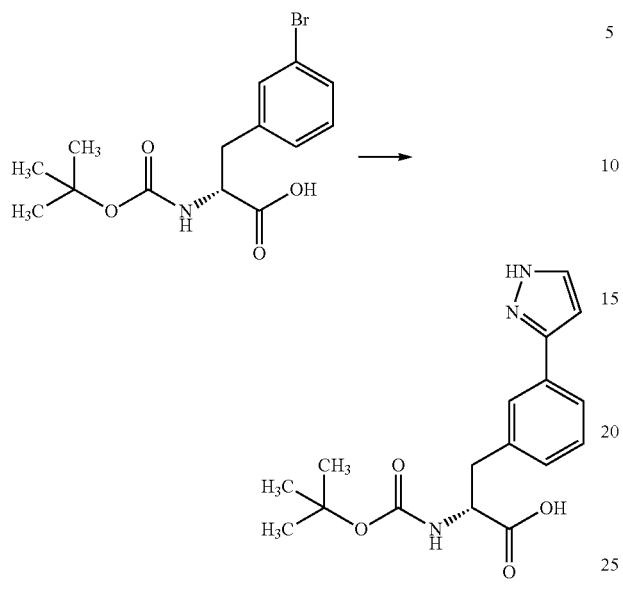

A microwave vial was charged with (2R)-2-[(tert-butoxy)carbonylamino]-3-(3-bromophenyl)propanoic acid (1.6 g, 4.66 mmol, 1 eq.), 1H-pyrazole-3-boronic acid (1.3 g, 3.6 mmol, 2.5 eq.), Na$_2$CO$_3$ (618 mg, 5.83 mmol, 4 eq.), and MeCN:H$_2$O (10:1, 22 mL). The reaction mixture was purged with argon and Pd(dppf)Cl$_2$ (341 mg, 0.46 mmol, 0.1 eq.) was added. The reaction mixture was heated at 90° C. under microwave irradiation for 1 h. It was then filtered through a Celite pad, washed with MeOH and the filtrate concentrated in vacuo to give the title compound as a brown solid.
Y=51%
MS ES$^+$: 332.2

Ethyl (2R)-2-amino-3-[3-(1H-pyrazol-3-yl)phenyl]propanoate Hydrochloride

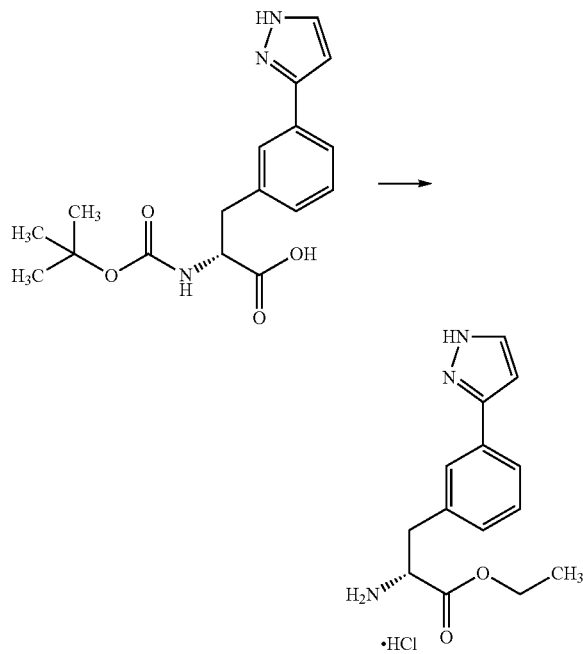

2-{[(tert-butoxy)carbonyl]amino}-3-[3-(1H-pyrazol-3-yl)phenyl]propanoic acid (250 mg, 1 mmol, 1 eq.) was dissolved in EtOH and the reaction mixture cooled to 0° C. Thionyl chloride (0.029 mL, 0.83 mmol, 1.1 eq.) was added and the reaction mixture stirred at 70° C. overnight. After cooling to rt it was concentrated in vacuo. Et$_2$O was added and the resulting brown solid filtered off. The solid was dissolved in MeOH and filtered through a SCX cartridge, washing with MeOH and eluting the product with a 1M NH$_3$ in MeOH solution.
The filtrate was evaporated to give the title compound as a pale brown solid.
Y=37%
MS ES$^+$: 260.2

2-methoxyethyl (2R)-2-amino-3-(pyridine-3-yl)propanoate Hydrochloride

To a solution of (2R)-2-amino-3-(pyridin-3-yl)propanoic acid (150 mg, 0.536 mmol, 1 eq.) in 2-methoxyethanol (2 ml) at 0° C. was added thionyl chloride (21 μl, 1.1 eq.) dropwise. The RM was heated at 60° C. for 2 h under argon. The RM was then allowed to cool to rt, poured into aqueous saturated NaHCO$_3$ and the mixture extracted with DCM twice. The combined organics were dried over Na$_2$SO$_4$, filtered and concentrated in vacuo to give the title compound as a white solid.
Y=71%
MS ES$^+$: 225.3
$^1$H NMR (400 MHz, DMSO-d6) δ 8.42 (d, J=2 Hz, 1H), 8.41 (d, J=2 Hz, 1H), 7.68-7.58 (m, 1H), 7.33-7.27 (m, 1H), 4.15-4.11 (m, 1H), 3.63-3.59 (m, 1H), 3.53-3.44 (m, 3H), 3.40-3.28 (m, 2H), 3.25 (s, 3H), 2.92-2.85 (m, 1H), 2.84-2.76 (m, 1H).

Cyclobutyl (2R)-2-amino-3-(pyridine-3-yl)propanoate

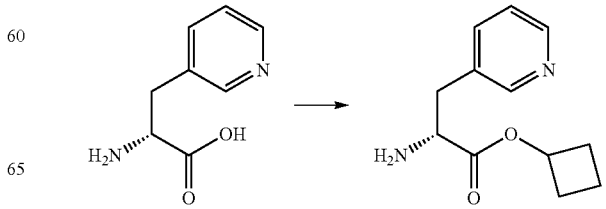

(2R)-2-Amino-3-(pyridin-3-yl)propanoic acid (100 mg, 0.60 mmol, 1 eq.) and cyclobutanol (860 mg, 12.03 mmol, 20 eq.) were suspended in toluene. Para-toluenesulfonic acid monohydrate (343 mg, 1.80 mmol, 3 eq.) was added and the mixture heated to reflux for 2 h. The reaction mixture was concentrated under reduced pressure and the residue dissolved in DCM/water (1:1). The mixture was neutralized with saturated aqueous NaHCO$_3$ and the aqueous layer extracted twice with DCM. The combined organics were washed with brine, dried over anhydrous Na$_2$SO$_4$, filtered and concentrated in vacuo to give the title compound as a brown oil.

Y=46%

MS ES$^+$: 222.3

(2R)-2-{[(Tert-butoxy)carbonyl]amino}-3-(pyridine-3-yl)propanoic Acid

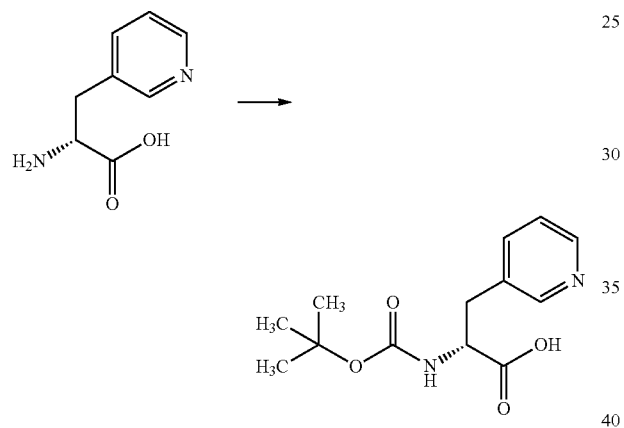

(2R)-2-Amino-3-(pyridin-3-yl)propanoic acid (1.5 g, 9 mmol, 1 eq.) was dissolved in dioxane (30 ml) and water (30 ml), then the resulting solution treated with sodium bicarbonate (3 g, 36.1 mmol, 4 eq.). The resulting mixture was cooled to 0° C. and a solution of Boc anhydride (2.36 g, 11 mmol, 1.2 eq.) in dioxane (10 ml) was added dropwise. The reaction mixture was stirred at 0° C. for 1 h and allowed to warm to room temperature overnight. The dioxane was evaporated under reduced pressure and the resulting aqueous solution washed twice with ethyl acetate. The aqueous layer was neutralised with a 10% aqueous solution of potassium bisulfate and the solution was extracted three times with n-butanol. The combined organic layers were dried over sodium sulfate, filtered and evaporated under vacuum to give the title compound as a pale yellow oil.

Y=51%

MS ES$^+$: 267.2

$^1$H NMR (400 MHz, DMSO-d6) δ 12.74 (s, 1H), 8.46-8.43 (m, 1H), 8.43-8.39 (m, 1H), 7.67 (d, J=8 Hz, 1H), 7.35-7.28 (m, 1H), 7.17 (d, J=8 Hz, 1H), 4.16-4.08 (m, 1H), 3.10-3.02 (m, 1H), 2.87-2.78 (m, 1H), 1.31 (s, 9H).

Cyclopropylmethyl (2R)-2-{[(tert-butoxy)carbonyl]amino}-3-(pyridine-3-yl)propanoate

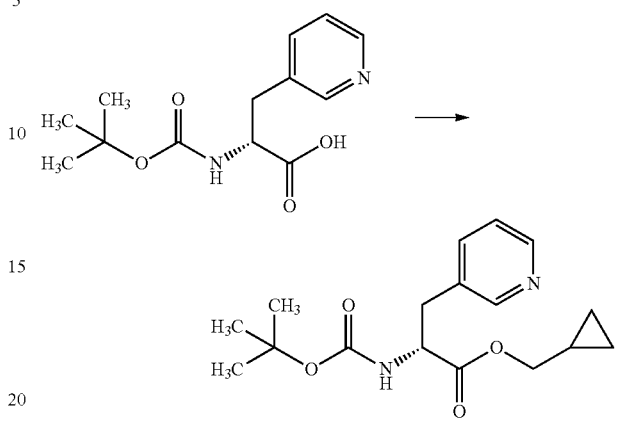

(2R)-2-{[(tert-butoxy)carbonyl]amino}-3-(pyridine-3-yl)propanoic acid (300 mg, 1.12 mmol, 1 eq.) and DMAP (14 mg, 0.113 mmol, 0.1 eq.) were dissolved in dry DCM (12 ml). The reaction mixture was cooled to 0° C. and 1-Ethyl-3-(3-dimethylaminopropyl)carbodiimide hydrochloride (281 mg, 1.46 mmol, 1.3 eq.) was added followed by cyclopropylmethanol (119 μl, 1.46 mmol, 1.3 eq.). The reaction mixture was stirred at rt under argon for 18 h. Ethyl acetate was added and the insoluble material was filtered off. The filtrate was concentrated in vacuo to give the title compound as an oil.

Y=56%

MS ES$^+$: 321.3

Cyclopropylmethyl (2R)-2-amino-3-(pyridine-3-yl)propanoate

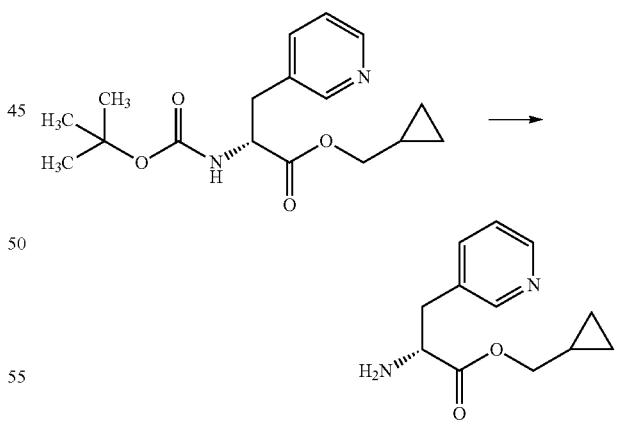

Cyclopropylmethyl (2R)-2-{[(tert-butoxy)carbonyl]amino}-3-(pyridine-3-yl)propanoate (200 mg, 0.52 mmol) was dissolved in DCM (1 ml) and TFA (2 ml). The reaction mixture was stirred at rt overnight. It was then diluted with DCM and neutralized with aq. sat. NaHCO$_3$. The aqueous layer was extracted twice with DCM and the combined organics dried over Na$_2$SO$_4$, filtered and concentrated in vacuo to give the title compound as a yellow oil.

Y=59%

MS ES$^+$: 221.3

Cyclopentyl (2R)-2-{[(tert-butoxy)carbonyl]amino}-3-(pyridine-3-yl)propanoate

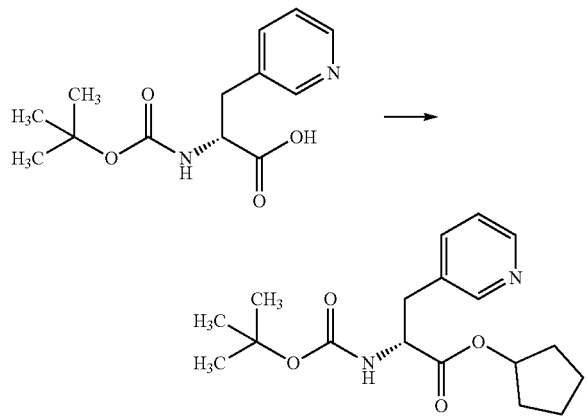

To a solution of (2R)-2-{[(tert-butoxy)carbonyl]amino}-3-(pyridine-3-yl)propanoic acid (150 mg, 0.56 mmol, 1 eq.) in DMF (4 ml) at 0° C. was added cyclopentanol (256 µl, 2.81 mmol, 5 eq.), 1-ethyl-3-(3-dimethylaminopropyl)carbodiimide hydrochloride (140 mg, 0.73 mmol, 1.3 eq.) and DMAP (7 mg, 0.056 mmol, 0.1 eq.). The reaction mixture was stirred at rt overnight then diluted with ethyl acetate. The mixture was filtered and the filtrate concentrated under reduced pressure. The crude product was purified by FCC (NH$_2$ modified silica gel) with hexane:EtOAc (4:1) to give the title product as a colourless oil.

Y=31%

MS ES$^+$: 335.3

$^1$H NMR (400 MHz, DMSO-d6) δ 8.45-8.40 (m, 2H), 7.67 (d, J=8 Hz, 1H), 7.37-7.29 (m, 2H), 5.10-5.02 (m, 1H), 4.17-4.08 (m, 1H), 3.03-2.96 (m, 1H), 2.93-2.86 (m, 1H), 1.85-1.70 (m, 2H), 1.65-1.55 (m, 3H), 1.53-1.40 (m, 3H), 1.33 (s, 9H).

Cyclopentyl (2R)-2-amino-3-(pyridine-3-yl)propanoate di-TFA Salt

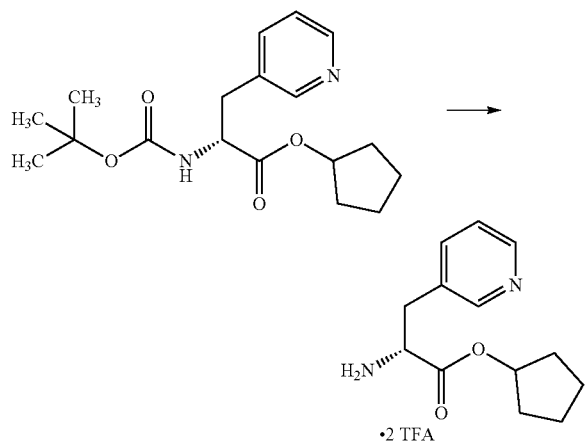

Cyclopentyl (2R)-2-{[(tert-butoxy)carbonyl]amino}-3-(pyridine-3-yl)propanoate (100 mg, 0.26 mmol, 1 eq.) was dissolved in DCM (1 ml) and TFA (2 ml) was added. The reaction mixture was stirred overnight at rt and concentrated under reduced pressure to give the title compound as a brown oil.

Y=78%

MS ES$^+$: 235.3

(2R)-2-Amino-3-(pyridin-3-yl)propanoic Acid Hydrochloride

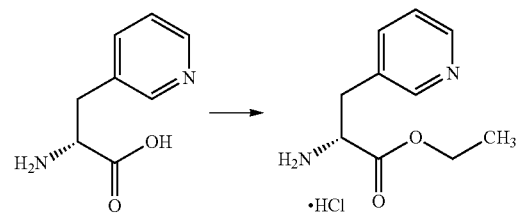

In a pressure vessel, (2R)-2-amino-3-(pyridin-3-yl)propanoic acid (2 g, 12.0 mmol, 1 eq.) was suspended in dry EtOH (30 ml). The mixture was cooled to 0° C. over an ice bath and conc. sulfuric acid (0.5 ml) was added under argon. The vessel was sealed and the mixture was stirred at 85° C. for 18 h. After allowing to cool to rt, the reaction mixture was evaporated to one quarter of its volume and poured into sat. NaHCO$_3$. The mixture was extracted four times with CHCl$_3$ and the combined organic layers dried over sodium sulfate and filtered. To the filtrate was added 4 M HCl in dioxane (12 ml). The resulting solution was evaporated to give a colourless oil which was dissolved in EtOH (10 ml). The solution was added to rapidly stirring Et$_2$O (100 ml) and stirring was continued for 1 h, until the resulting oil solidified into a white solid. The solid was filtered off, washed with Et$_2$O and dried in vacuo to give the title compound as a white powder.

Y=61%

MS ES$^+$: 195.3

$^1$H NMR (400 MHz, DMSO-d6) δ 9.11-8.91 (m, 4H), 8.86 (d, J=6 Hz, 1H), 8.56 (d, J=8 Hz, 1H), 8.08-8.00 (m, 1H), 4.55-4.45 (m, 1H), 4.27-4.10 (m, 2H), 3.47 (d, J=7 Hz, 2H), 1.17 (t, J=7 Hz, 2H).

Methyl 2-amino-3-(4-methyl-1H-pyrazol-1-yl)propanoate Hydrochloride

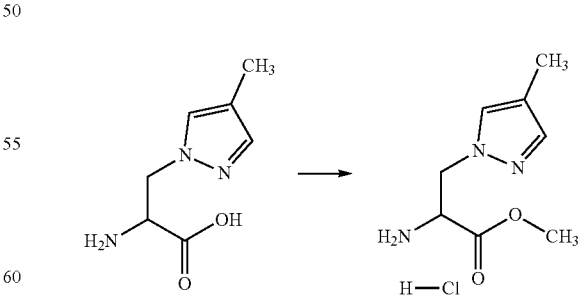

A solution of 2-amino-3-(4-methyl-1H-pyrazol-1-yl)propanoate (70 mg, 0.34 mmol) in 3 M hydrochloric acid in methanol (5 ml) was stirred at rt for 16 h. The solvent was removed in vacuo to give the desired product.

Y=92%

MS ES$^+$: 184

Ethyl 2-amino-3-(pyrimidin-2-yl)propanoate Dihydrochloride

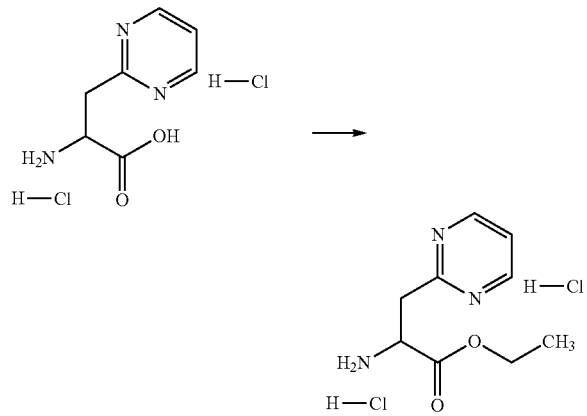

In a vial 2-amino-3-(pyrimidin-2-yl)propanoic acid dihydrochloride (0.10 g, 0.417 mmol) was suspended in EtOH (1 ml) and cooled to 0° C. Conc. $H_2SO_4$ (0.1 ml) was added, the vial sealed and heated at 80° C. for 18 h. The RM was poured into sat. $NaHCO_3$ and extracted four times with $CHCl_3$. The combined organics were dried over $Na_2SO_4$ and filtered. To the filtrate was added 4M HCl in dioxane (2 ml) with stirring. This solution was evaporated to give a colourless oil which was then dissolved in the minimum amount of EtOH (approx. 2 ml). The solution was added to rapidly stirred MeCN (10 ml) to crystallise the product. The solid was filtered and dried in vacuo to give the desired product as an off-white solid.

Y=66%
MS ES+: 196.3

Methyl (2R)-2-amino-3-(5-methoxypyridin-3-yl)propanoate Dihydrochloride

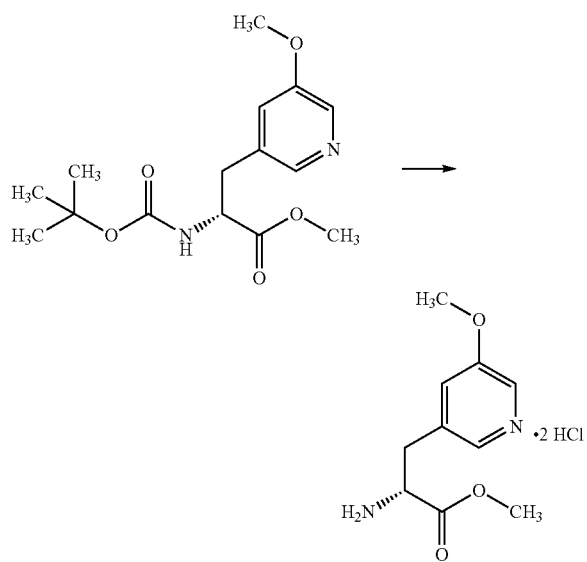

Methyl (2R)-2-{[(tert-butoxy)carbonyl]amino}-3-(5-methoxypyridin-3-yl)propanoate (0.26 g, 0.8 mmol) was dissolved in 4M HCl in dioxane (5 ml) and stirred at rt for 4 h. The solvent was evaporated and the solid dissolved in water and washed with EtOAc. The aqueous phase was freeze-dried to give the desired product as a brown solid.

Y=37%
MS ES+: 211.2

Ethyl 2-[(diphenylmethylidene)amino]acetate

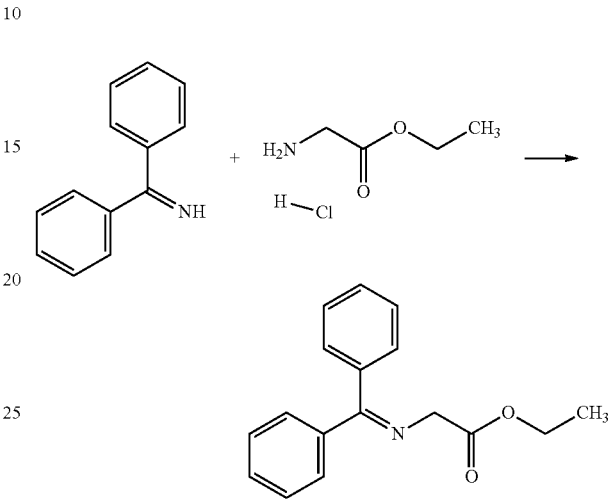

Glycine ethyl ester hydrochloride (1.00 g, 7.16 mmol) was dissolved in dry DCM (40 ml). Benzophenone imine (1.20 ml, 7.16 mmol) was added dropwise. The RM was stirred at rt for 18 h. The RM was filtered through Celite, washed with DCM and the filtrate concentrated in vacuo. The resulting oil was triturated with hexane to give the desired product as a white solid.

Y=97%
MS ES+: 268

Ethyl 2-[(diphenylmethylidene)amino]-3-(3-methyl-1,2,4-oxadiazol-5-yl)propanoate

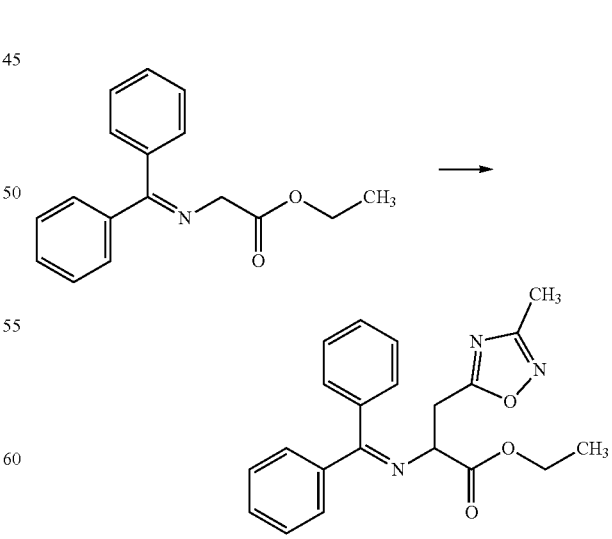

In a dry flask 2M LDA in THF (0.59 ml, 1.18 mmol) was cooled to −78° C. under nitrogen. A solution of ethyl 2-[(diphenylmethylidene)amino]acetate in THF (12 ml) was added and the RM stirred at −78° C. for 30 min. 5-(chloromethyl)-3-methyl-1,2,4-oxadiazole (0.12 ml, 1.18 mmol) was added dropwise and the RM stirred at −78° C. for 1 h, then at rt for 18 h. The RM was quenched with sat. NH$_4$Cl, diluted with water and extracted with EtOAc. The organics were dried over Na$_2$SO$_4$, filtered and evaporated. The crude was purified by FCC (silica, 20% EtOAc in hexane) to give the desired product.

Y=20%

MS ES$^+$: 364

Ethyl 2-amino-3-(3-methyl-1,2,4-oxadiazol-5-yl)propanoate Hydrochloride

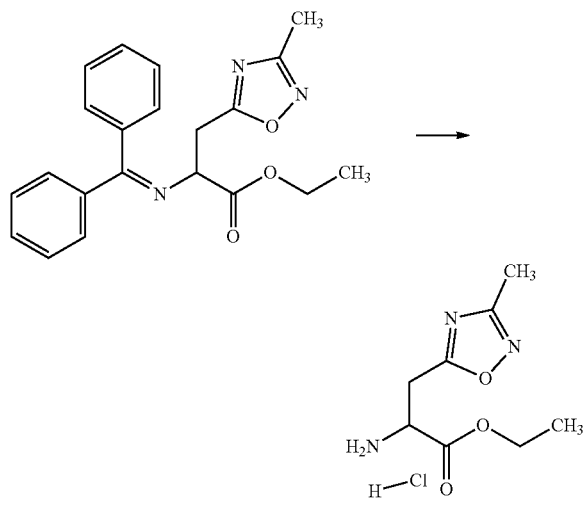

Ethyl 2-[(diphenylmethylidene)amino]-3-(3-methyl-1,2,4-oxadiazol-5-yl)propanoate (80 mg, 0.23 mmol) was dissolved in diethyl ether (2 ml) and cooled to 0° C. 1M aqueous HCl (1.1 ml, 1.1 mmol) was added dropwise and the reaction allowed to warm to rt. The RM was stirred for 72 h and then concentrated to remove the organic solvent. The aqueous was diluted with 1M HCl and washed with Et$_2$O. The aqueous was concentrated in vacuo and freeze-dried to give the desired product as a yellow solid.

Y=80%

MS ES$^+$: 200

Methyl (2R)-2-{[(tert-butoxy)carbonyl]amino}-3-(pyridazin-3-yl)propanoate

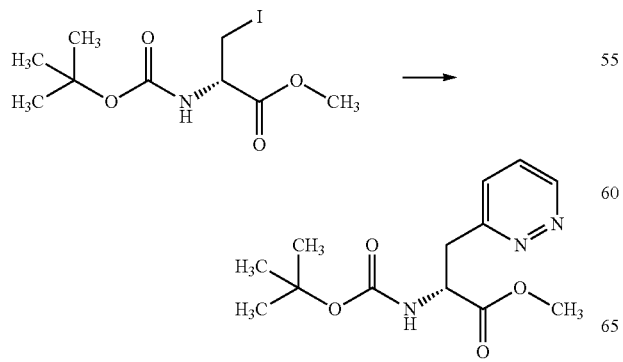

Zinc powder (0.12 g, 1.8 mmol) was added to a dry flask purged with nitrogen. Dry DMF (1.0 ml) was added followed by iodine (43 mg, 0.2 mmol). The solution changed from colourless to yellow and then back to colourless. Methyl (2S)-2-{[(tert-butoxy)carbonyl]amino}-3-iodopropanoate (0.20 g, 0.60 mmol) was added, followed by iodine (43 mg, 0.2 mmol). The solution was stirred at ambient temperature, with an exotherm observed. To this solution was added Pd$_2$(dba)$_3$ (28 mg, 0.04 mmol), SPhos (25 mg, 0.12 mmol) and 3-bromopyridazine (0.25 g, 1.6 mmol). The RM was stirred at rt under nitrogen for 18 h. The RM was filtered twice and purified by FCC (silica, EtOAc/hexane) to give the desired product.

Y=43%

MS ES$^+$: 282

Methyl (2R)-2-amino-3-(pyridazin-3-yl)propanoate Hydrochloride

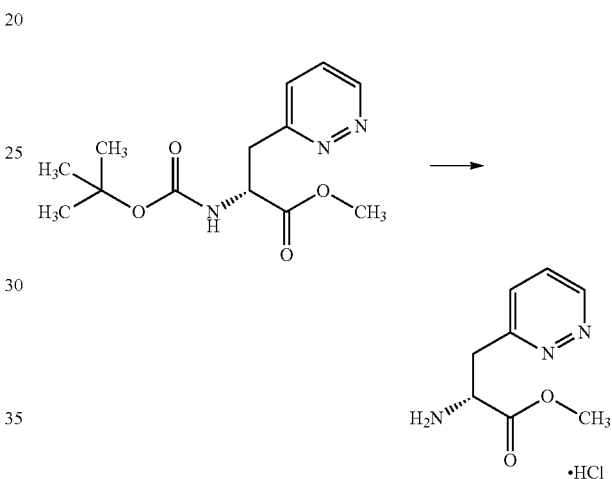

General Procedure C

Y=97%

MS ES$^+$: 182

Ethyl 2-[(diphenylmethylidene)amino]-3-(1,2-oxazol-4-yl)propanoate

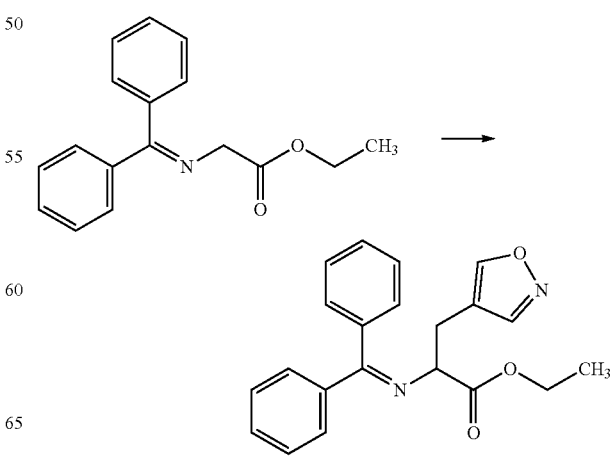

A dry flask was charged with 2M LDA in THF/hexane/toluene (0.59 ml, 1.18 mmol) and cooled to −78° C. under nitrogen. A solution of ethyl 2-[(diphenylmethylidene)amino]acetate (0.30 g, 1.12 mmol) in dry THF (16 ml) was added dropwise. The RM was stirred at −78° C. for 30 min, then 4-(bromomethyl)-1,2-oxazole (0.19 g, 1.18 mmol) was added and stirring continued at −78° C. for 1 h. The RM was allowed to warm to rt and stirred for 16 h. The RM was cooled over ice-water and quenched with sat. NH$_4$Cl. The organics were extracted with EtOAc, dried over sodium sulfate, filtered and concentrated. The desired product was obtained and used directly without further purification.

Y=51%

MS ES$^+$: 349.1

Ethyl 2-amino-3-(1,2-oxazol-4-yl)propanoate Hydrochloride

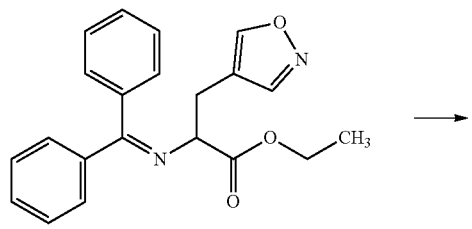

Ethyl 2-[(diphenylmethylidene)amino]-3-(1,2-oxazol-4-yl)propanoate (0.30 g, 0.86 mmol) was dissolved in diethyl ether (4 ml) and cooled to 0° C. 1M hydrochloric acid (2.0 ml, 1.0 mmol) was added dropwise, the RM was allowed to warm to rt and stirred for 16 h. The RM was diluted with water and washed with diethyl ether. The aqueous phase was dried in vacuo to give the desired product, used as is.

Y=94%

MS ES$^+$: 185.2

Ethyl 2-[(diphenylmethylidene)amino]-3-(1,2-oxazol-3-yl)propanoate

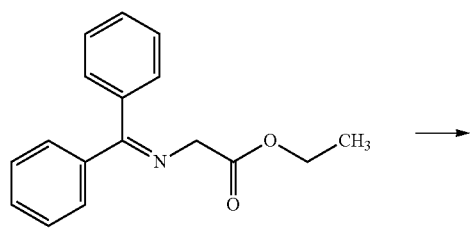

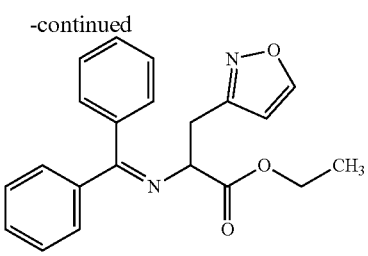

A dry flask was charged with 2M LDA in THF/hexane/toluene (0.78 ml, 1.56 mmol) and cooled to −78° C. under nitrogen. A solution of ethyl 2-[(diphenylmethylidene)amino]acetate (0.40 g, 1.49 mmol) in dry THF (14 ml) was added dropwise. The RM was stirred at −78° C. for 30 min, then 3-(bromomethyl)isoxazole (0.148 ml, 1.56 mmol) was added and stirring continued at −78° C. for 1 h. The RM was allowed to warm to rt and stirred for 16 h. The RM was cooled over ice-water and quenched with sat. NH$_4$Cl. The organics were extracted with EtOAc, dried over sodium sulfate, filtered and concentrated. The desired product was obtained as a yellow oil and used directly without further purification.

Y=25%

MS ES$^+$: 349.1

Ethyl 2-amino-3-(1,2-oxazol-3-yl)propanoate Hydrochloride

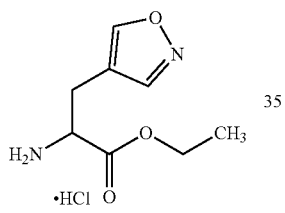

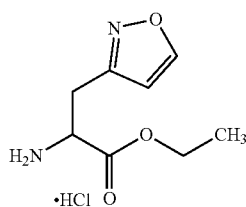

Ethyl 2-[(diphenylmethylidene)amino]-3-(1,2-oxazol-3-yl)propanoate (0.13 g, 0.39 mmol) was dissolved in diethyl ether (2 ml) and cooled to 0° C. 1M hydrochloric acid (1.9 ml, 1.9 mmol) was added dropwise; the RM was allowed to warm to rt and stirred for 16 h. The RM was diluted with 1M hydrochloric acid and washed with diethyl ether. The aqueous phase was dried in vacuo to give the desired product as a yellow solid, used as is.

Y=81%

MS ES$^+$: 185

6-(prop-1-en-2-yl)-2,3-dihydro-1H-inden-5-amine

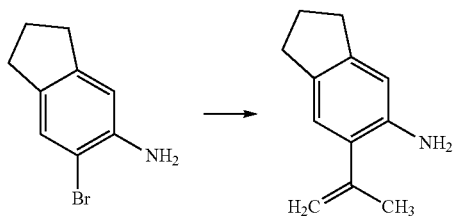

6-bromo-2,3-dihydro-1H-inden-5-amine (1.50 g, 7.1 mmol) and K₃PO₄ (3.75 g, 17.7 mmol) were placed in a tube. Toluene (12 ml) and water (6 ml) were added. Palladium acetate (0.16 g, 0.7 mmol), tricyclohexylphosphine (0.20 g, 0.7 mmol) and isopropenylboronic acid pinacol ester (1.78 g, 10.6 mmol) were then added, the tube sealed at heated at 105° C. for 16 h. The RM was filtered through Celite, the organic solvent evaporated, and the resulting suspension partitioned between EtOAc and brine. The organic phase was concentrated and purified by FCC (silica, 4:1 hexane/EtOAc) to give the desired product.
Y=5%
MS ES⁺: 174.3

6-(propan-2-yl)-2,3-dihydro-1H-inden-5-amine

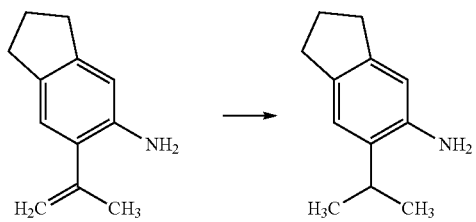

6-(prop-1-en-2-yl)-2,3-dihydro-1H-inden-5-amine (0.267 g, 1.54 mmol) was dissolved in MeOH (5 ml). 10% wt. Pd/C (16 mg) was added and the RM purged with argon. The RM was hydrogenated using Parr hydrogenation apparatus for 6 h. The RM was filtered through Celite and concentrated to give the desired product, used without further purification.
Y=82%
MS ES⁺: 176.3

5-isocyanato-6-(propan-2-yl)-2,3-dihydro-1H-indene

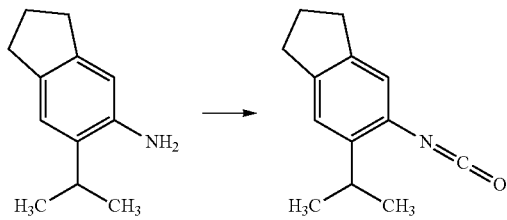

6-(propan-2-yl)-2,3-dihydro-1H-inden-5-amine (222 mg, 1.27 mmol) was dissolved in THF (10 ml) and triethylamine (0.19 ml, 0.14 mmol) was added. The RM was then treated with triphosgene (128 mg, 0.4 mmol), the RM heated at reflux for 4 h and cooled to RT. The solvent was removed in vacuo, the residue dissolved in pentane and filtered through silica.
The filtrate was evaporated to give the desired product.
Y=26%
MS ES⁺ in MeOH: 234.3 (carbamate)

Methyl (2R)-2-{[(tert-butoxy)carbonyl]amino}-3-(pyrimidin-5-yl)propanoate

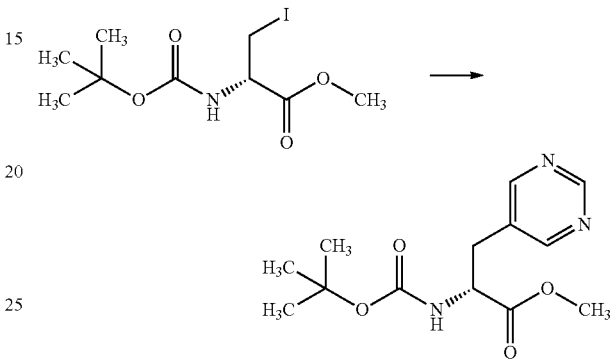

Zinc powder (0.12 g, 1.8 mmol) was added to a dry flask purged with nitrogen. Dry DMF (1.0 ml) was added followed by iodine (43 mg, 0.2 mmol). The solution changed from colourless to yellow and then back to colourless. Methyl (2S)-2-{[(tert-butoxy)carbonyl]amino}-3-Iodopropanoate (0.20 g, 0.60 mmol) was added, followed by iodine (43 mg, 0.2 mmol). The solution was stirred at ambient temperature, with an exotherm observed. To this solution was added Pd₂(dba)₃ (28 mg, 0.04 mmol), SPhos (24 mg, 0.12 mmol) and 5-iodopyrimidine (0.33 g, 1.6 mmol). The RM was stirred at rt under nitrogen for 18 h. The RM was filtered twice and then purified by FCC (silica, EtOAc/hexane) to give the desired product.
Y=80%
MS ES⁺: 282

Methyl (2R)-2-amino-3-(pyrimidin-5-yl)propanoate Hydrochloride

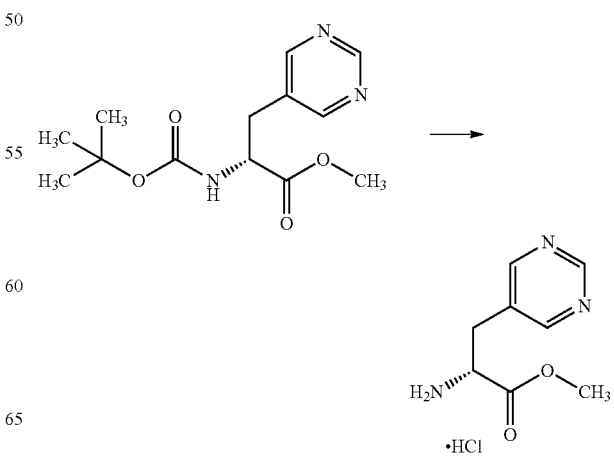

General Procedure C

Y=94%
MS ES+: 182.2

Methyl (2R)-2-{[(tert-butoxy)carbonyl]amino}-3-(pyrazin-2-yl)propanoate

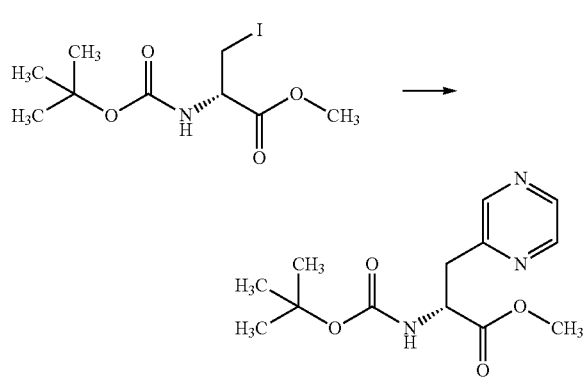

Zinc powder (0.24 g, 3.6 mmol) was added to a dry flask purged with nitrogen. Dry DMF (2 ml) was added followed by iodine (86 mg, 0.4 mmol). The solution changed from colourless to yellow and then back to colourless. Methyl (2S)-2-{[(tert-butoxy)carbonyl]amino}-3-Iodopropanoate (0.40 g, 1.2 mmol) was added, followed by iodine (86 mg, 0.4 mmol). The solution was stirred at ambient temperature, with an exotherm observed. To this solution was added Pd$_2$(dba)$_3$ (28 mg, 0.04 mmol), SPhos (24 mg, 0.12 mmol) and 2-iodopyrazine (0.32 g, 1.5 mmol). The RM was stirred at rt under nitrogen for 18 h. The RM was filtered twice and then purified by FCC (silica, EtOAc/hexane) to give the desired product.
Y=90%
MS ES+: 282

Methyl (2R)-2-amino-3-(pyrazin-2-yl)propanoate Hydrochloride

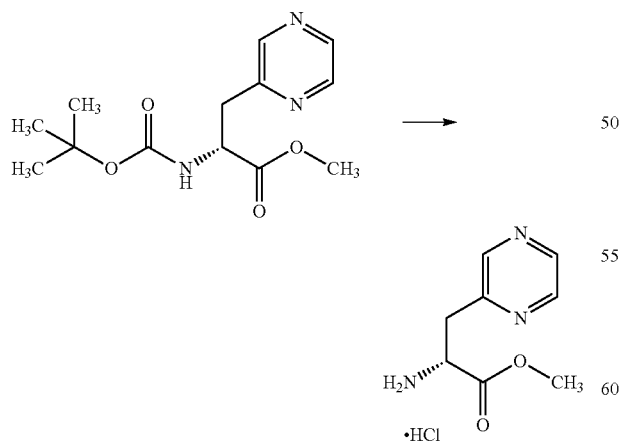

General Procedure C

Y=66%
MS ES+: 182.1

Ethyl 2-[(diphenylmethylidene)amino]-3-(pyridazin-4-yl)propanoate

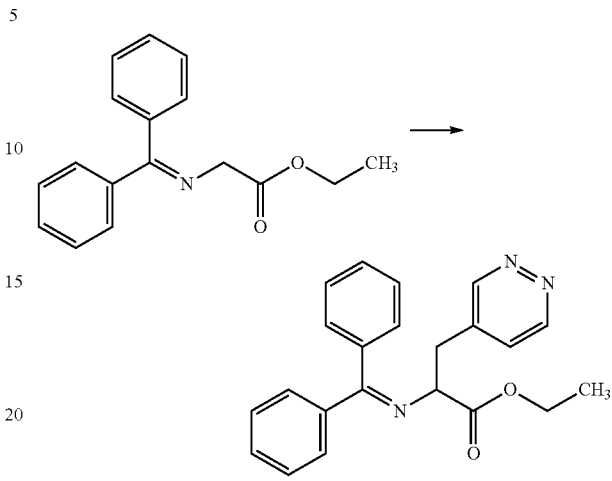

A dry flask was charged with 2M LDA in THF/hexane/toluene (1.2 ml, 4.86 mmol) and cooled to −78° C. under nitrogen. A solution of ethyl 2-[(diphenylmethylidene)amino]acetate (0.65 g, 2.43 mmol) in dry THF (25 ml) was added dropwise. The RM was stirred at −78° C. for 30 min, then 4-(bromomethyl)pyridazine hydrobromide (0.65 g, 2.55 mmol) and triethylamine (0.356 ml, 2.55 mmol) were added and stirring continued at −78° C. for 1 h. The RM was allowed to warm to rt and stirred for 16 h. The RM was cooled over ice-water and quenched with sat. NH$_4$Cl. The organics were extracted with EtOAc, dried over sodium sulfate, filtered and concentrated. The crude was purified by FCC (silica, 20% (EtOAc+1% Et$_3$N) in hexane to give the desired product.
Y=13%
MS ES+: 360.1

Ethyl 2-amino-3-(pyridazin-4-yl)propanoate Hydrochloride

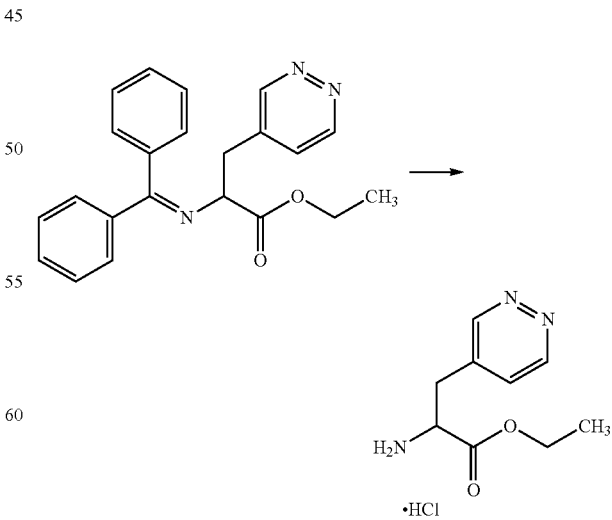

Ethyl 2-[(diphenylmethylidene)amino]-3-(pyridazin-4-yl)propanoate (0.14 g, 0.38 mmol) was dissolved in diethyl ether (2.5 ml). 1M hydrochloric acid (1.0 ml, 1.0 mmol) was added and the RM stirred for 16 h. The RM was diluted with 1M hydrochloric acid and washed with diethyl ether. The aqueous phase was dried in vacuo to give the desired product as a brown oil, used as is.

Y=83%
MS ES+: 196

(pyrimidin-4-yl)methyl Methanesulfonate

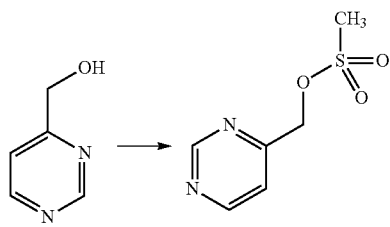

A solution of (pyrimidin-4-yl)methanol (0.20 g, 1.82 mmol) in DCM (4 ml) was cooled to 0° C. and treated with triethylamine (0.506 ml, 3.63 mmol) and methanesulfonic acid (0.281 ml, 3.63 mmol). The RM was allowed to warm to RT and stirred for 4 h. The RM was diluted with DCM, washed sequentially with water and brine, dried over sodium sulfate and concentrated to give the desired product, used directly.

Y=91%
MS ES+: 188.9

Ethyl 2-[(diphenylmethylidene)amino]-3-(pyrimidin-4-yl)propanoate

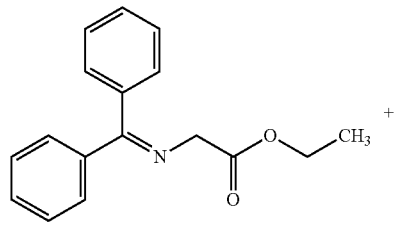

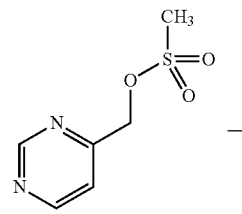

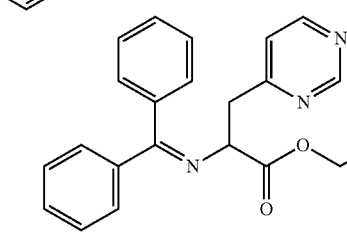

A dry flask was charged with 2M LDA in THF/hexane/toluene (2.25 ml, 4.50 mmol) and cooled to −78° C. under nitrogen. A solution of ethyl 2-[(diphenylmethylidene) amino]acetate (0.60 g, 2.24 mmol) in dry THF (20 ml) was added dropwise. The RM was stirred at −78° C. for 30 min, then (pyrimidin-4-yl)methyl methanesulfonate (0.44 g, 2.36 mmol) was added and stirring continued at −78° C. for 1 h. The RM was allowed to warm to rt and stirred for 16 h. The RM was cooled over ice-water and quenched with sat. NH₄Cl. The organics were extracted with EtOAc, dried over sodium sulfate, filtered and concentrated to give the desired product, used directly in the next step.

Y=14%
MS ES+: 360.1

Ethyl 2-amino-3-(pyrimidin-4-yl)propanoate Hydrochloride

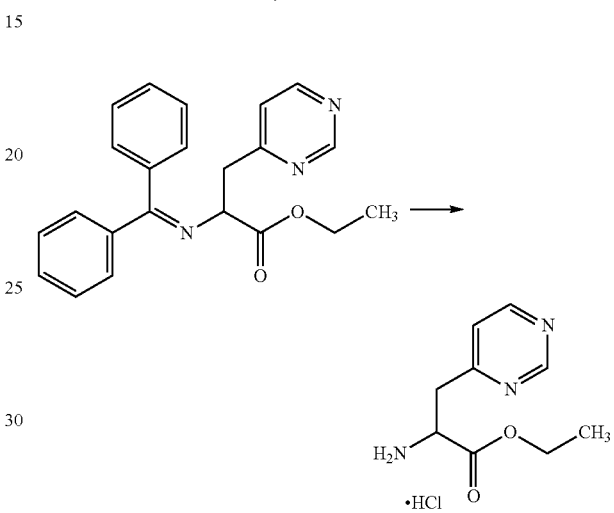

Ethyl 2-[(diphenylmethylidene)amino]-3-(pyrimidin-4-yl)propanoate (0.46 g, 1.71 mmol) was dissolved in diethyl ether (3 ml). 1M hydrochloric acid (3 ml, 3 mmol) was added and the RM stirred for 16 h. The RM was diluted with 1M hydrochloric acid and washed with diethyl ether. The aqueous phase was dried in vacuo to give the desired product, used as is.

Y=25%
MS ES+: 196

Example Compounds of the Disclosure

The following compounds of the disclosure were prepared as follows, with the necessary steps and starting materials required as previously described:

2A

Methyl 2-{[(1,2,3,5,6,7-hexahydro-s-indacen-4-yl)carbamoyl]amino}-3-(3-hydroxyphenyl)propanoate

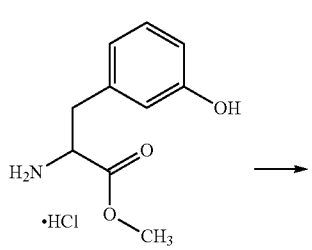

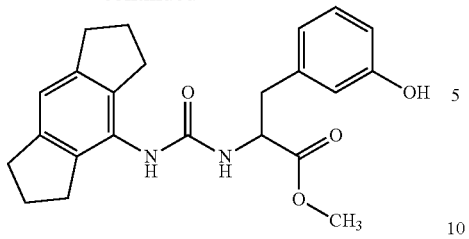

SM: methyl 2-amino-3-(3-hydroxyphenyl)propanoate hydrochloride

General Procedure A

Y=8%

MS ES+: 395.2

$^1$H NMR (400 MHz, DMSO-d6) δ 9.31 (s, 1H), 7.88 (s, 1H), 7.08 (t, J=8 Hz, 1H), 6.87 (s, 1H), 6.67-6.61 (m, 1H), 6.61-6.55 (m, 2H), 6.29 (d, J=8 Hz, 1H), 4.48-4.43 (m, 1H), 3.64 (s, 3H), 2.99-2.83 (m, 2H), 2.79 (t, J=7 Hz, 4H), 2.65 (t, J=8 Hz, 4H), 1.98-1.91 (m, 4H).

2B

Methyl 2-{[(1,2,3,5,6,7-hexahydro-s-indacen-4-yl)carbamoyl]amino}-3-(2-hydroxyphenyl)propanoate

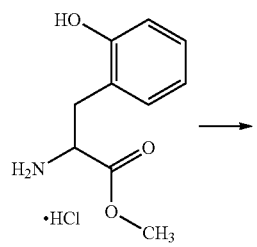

SM: methyl 2-amino-3-(2-hydroxyphenyl)propanoate hydrochloride

General Procedure A

Y=16%

MS ES+: 395

$^1$H NMR (400 MHz, DMSO-d6) δ 9.44 (s, 1H), 7.81 (s, 1H), 7.09-7.00 (m, 2H), 6.86 (s, 1H), 6.79 (d, J=7 Hz, 1H), 6.73-6.70 (m, 1H), 6.27 (d, J=8 Hz, 1H), 4.50-4.45 (m, 1H), 3.60 (s, 3H), 3.04-2.82 (m, 2H), 2.78 (t, J=7 Hz, 4H), 2.67-2.55 (m, 4H), 1.97-1.90 (m, 4H).

2C

Methyl 3-(3-acetylphenyl)-2-{[(1,2,3,5,6,7-hexahydro-s-indacen-4-yl)carbamoyl]amino}propanoate

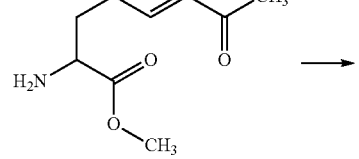

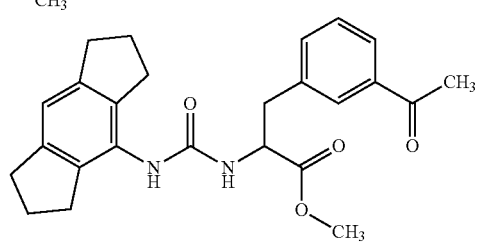

SM: Methyl 3-(3-acetylphenyl)-2-aminopropanoate

General Procedure A

Y=71%

MS ES+: 421.3

$^1$H NMR (400 MHz, CDCl$_3$) δ 7.82 (d, J=8 Hz, 1H), 7.66 (s, 1H), 7.35 (t, J=8 Hz, 1H), 7.26 (s, 1H), 7.03 (s, 1H), 5.88 (s, 1H), 4.91-4.82 (m, 2H), 3.75 (s, 3H), 3.27-3.20 (m, 1H), 3.11-3.04 (m, 1H), 2.88 (t, J=7 Hz, 4H), 2.81-2.72 (m, 2H), 2.71-2.61 (m, 2H), 2.57 (s, 3H), 2.08-1.97 (m, 4H).

2D

Methyl (2R)-3-(4-cyanophenyl)-2-{[(1,2,3,5,6,7-hexahydro-s-indacen-4-yl)carbamoyl]amino}propanoate

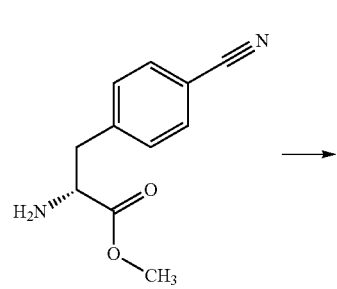

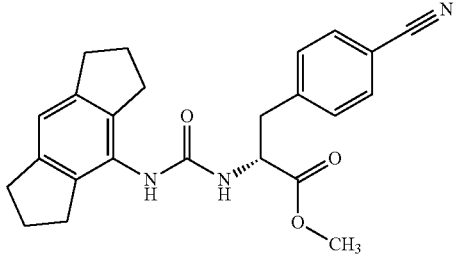

SM: methyl (2R)-2-amino-3-(4-cyanophenyl)propanoate

General Procedure A

Y=15%

MS ES+: 404.2

¹H NMR (400 MHz, DMSO-d6) δ 7.83-7.74 (m, 3H), 7.42 (d, J=8 Hz, 2H), 6.87 (s, 1H), 6.42 (d, J=8 Hz, 1H), 4.59-4.53 (m, 1H), 3.66 (s, 3H), 3.19-3.15 (m, 1H), 3.07-3.01 (m, 1H), 2.78 (t, J=7 Hz, 4H), 2.61-2.54 (m, 4H), 1.94 (quint, J=7 Hz, 4H).

2E

Methyl(2R)-3-(3-cyanophenyl)-2-{[(1,2,3,5,6,7-hexahydro-s-indacen-4-yl)carbamoyl]amino}propanoate

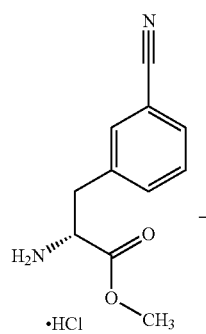

→

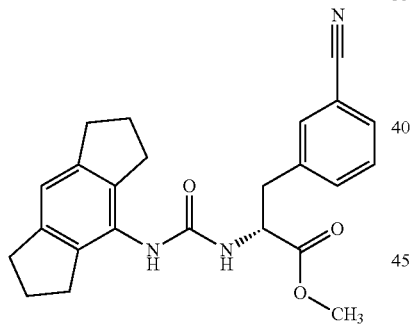

SM: methyl (2R)-2-amino-3-(3-cyanophenyl)propanoate hydrochloride

General Procedure A

The product was further purified by crystallisation from MeOH to give the title compound as a white solid.

Y=5%

MS ES+: 404.2

¹H NMR (400 MHz, DMSO-d6) δ 7.81 (s, 1H), 7.72 (d, J=7 Hz, 1H), 7.66 (s, 1H), 7.58-7.50 (m 2H), 6.87 (s, 1H), 6.42 (d, J=8 Hz, 1H), 4.58-4.52 (m, 1H), 3.67 (s, 3H), 3.17-3.14 (m, 1H), 3.04-2.99 (m, 1H), 2.78 (t, J=7 Hz, 4H), 2.60 (t, J=7 Hz, 4H), 1.98-1.90 (m, 4H).

2F

Methyl (2R)-2-{[(1,2,3,5,6,7-hexahydro-s-indacen-4-yl)carbamoyl]amino}-3-(pyridin-2-yl)propanoate

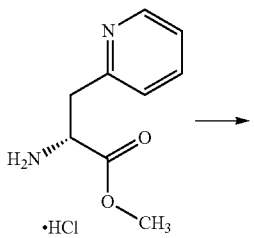

→

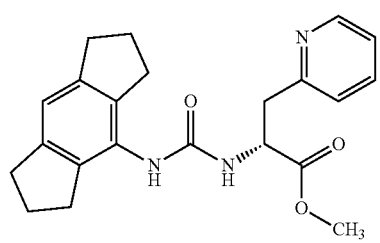

SM: methyl (2R)-2-amino-3-(pyridin-2-yl)propanoate hydrochloride

General Procedure A

Y=23%

MS ES+: 380

¹H NMR (400 MHz, DMSO-d6) δ 8.48-8.46 (m, 1H), 7.89 (s, 1H), 7.73-7.71 (m, 1H), 7.30-7.22 (m, 2H), 6.87 (s, 1H), 6.45 (d, J=8 Hz, 1H), 4.69-4.62 (m, 1H), 3.33 (s, 3H), 3.21-3.13 (m, 2H), 2.78 (t, J=7 Hz, 4H), 2.66-2.56 (m, 4H), 1.97-1.89 (m, 4H).

2G

Methyl2-{[(1,2,3,5,6,7-hexahydro-s-indacen-4-yl)carbamoyl]amino}-3-[3-(hydroxymethyl)phenyl]propanoate

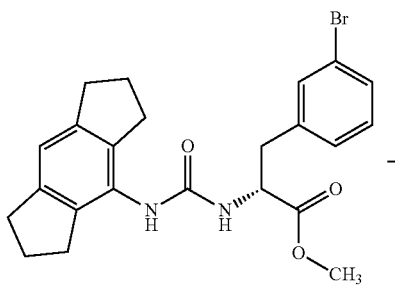

→

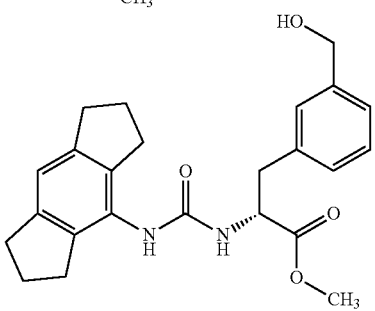

In a sealed tube (tributylstannyl)methanol (52 mg, 0.164 mmol, 1.5 eq.), tetrakis(triphenylphosphine)palladium(0) (6.3 mg, 0.005 mmol, 0.05 eq.) and methyl 3-(3-bromophenyl)-2-{[(1,2,3,5,6,7-hexahydro-s-indacen-4-yl)carbamoyl]amino}propanoate (50 mg, 0.109 mmol) were dissolved in anhydrous dioxane under Ar atmosphere at room temperature. The reaction mixture was stirred at 80° C. for 18 h. After cooling to room temperature, the reaction mixture was concentrated and purified by flash column chromatography (DCM/MeOH) to obtain the desired product as a yellow solid.

Y=45%

MS ES+: 409.2

¹H NMR (400 MHz, DMSO-d6) δ 7.86 (s, 1H), 7.26 (t, J=8 Hz, 1H), 7.19 (d, J=8 Hz, 1H), 7.13 (s, 1H), 7.05 (d, J=7 Hz, 1H), 6.87 (s, 1H), 6.33 (d, J=8 Hz, 1H), 5.16 (t, J=5 Hz, 1H), 4.52-4.43 (m, 3H), 3.64 (s, 3H), 3.06-3.02 (m, 1H), 2.98-2.92 (m, 1H), 2.79 (t, J=7 Hz, 4H), 2.64 (t, J=7 Hz, 4H), 2.00-1.89 (m, 4H).

2H

Methyl (2R)-2-{[(1,2,3,5,6,7-hexahydro-s-indacen-4-yl)carbamoyl]amino}-3-(pyridin-3-yl)propanoate SM: methyl (2R)-2-amino-3-(pyridin-3-yl)propanoate hydrochloride General Procedure A The product was further purified by preparative HPLC.

Y=6%

MS ES+: 380.3

¹H NMR (400 MHz, DMSO-d6) δ 8.46-8.44 (m, 1H), 8.41 (d, J=2 Hz, 1H), 7.85 (s, 1H), 7.63-7.61 (m, 1H), 7.35-7.32 (m, 1H), 6.87 (s, 1H), 6.45 (d, J=8 Hz, 1H), 4.55-4.49 (m, 1H), 3.66 (s, 3H), 3.13-3.08 (m, 1H), 3.01-2.95 (m, 1H), 2.78 (t, J=7 Hz, 4H), 2.61 (t, J=7 Hz, 4H), 1.98-1.90 (m, 4H).

2I

Methyl 2-{[(1,2,3,5,6,7-hexahydro-s-indacen-4-yl)carbamoyl]amino}-3-[3-(1-methyl-1H-imidazol-5-yl)phenyl]propanoate In a sealed tube 1-methyl-5-(tributylstannyl)imidazole (61 mg, 0.164 mmol, 1.5 eq.), tetrakis(triphenylphosphine)palladium(0) (6.3 mg, 0.005 mmol, 0.05 eq.) and methyl 3-(3-bromophenyl)-2-{[(1,2,3,5,6,7-hexahydro-s-indacen-4-yl)carbamoyl]amino}propanoate (50 mg, 0.109 mmol) were dissolved in anhydrous dioxane under Ar atmosphere at room temperature. The reaction mixture was stirred at 80° C. for 18 h. After cooling to room temperature, the reaction mixture was concentrated and purified by preparative HPLC to give the desired product as a yellow gum.

Y=10%

MS ES+: 459.4

¹H NMR (400 MHz, DMSO-d6) δ 9.05 (s, 1H), 7.84-7.73 (m, 2H), 7.52-7.45 (m, 3H), 7.41-7.34 (m, 1H), 6.87 (s, 1H), 6.46 (d, J=8 Hz, 1H), 4.61-4.54 (m, 1H), 3.83 (s, 3H), 3.67 (s, 3H), 3.19-3.14 (m, 1H), 3.07-3.01 (m, 1H), 2.77 (t, J=7 Hz, 4H), 2.60-2.55 (m, 4H), 1.98-1.89 (m, 4H).

2J

Methyl 2-{[(1,2,3,5,6,7-hexahydro-s-indacen-4-yl)carbamoyl]amino}-3-[3-(1H-pyrazol-5-yl)phenyl]propanoate

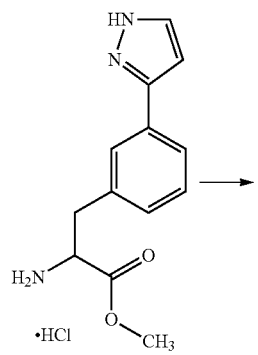

SM: methyl 2-amino-3-[3-(1H-pyrazol-5-yl)phenyl]propanoate hydrochloride

General Procedure A

Y=18%
MS ES+: 445.3
1H NMR (400 MHz, DMSO-d6) δ 12.86 (s, 1H), 7.85 (s, 1H), 7.78 (s, 1H), 7.73-7.58 (m, 2H), 7.33 (t, J=7 Hz, 1H), 7.19-7.06 (m, 1H), 6.85 (s, 1H), 6.67 (s, 1H), 6.37 (d, J=8 Hz, 1H), 4.58-4.49 (m, 1H), 3.66 (s, 3H), 3.13-3.08 (m, 1H), 3.03-2.97 (m, 1H), 2.77 (t, J=7 Hz, 4H), 2.61 (t, J=7 Hz, 4H), 1.96-1.86 (m, 4H).

2K

Methyl(2R)-2-{[(1,2,3,5,6,7-hexahydro-s-indacen-4-yl)carbamoyl]amino}-3-(3-hydroxyphenyl)propanoate

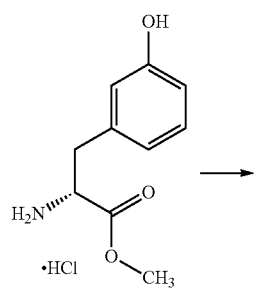

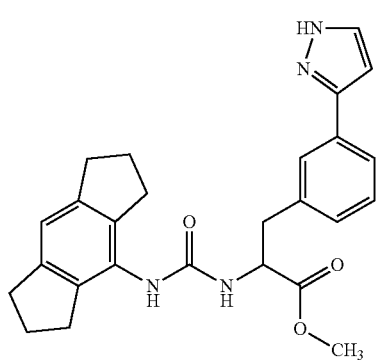

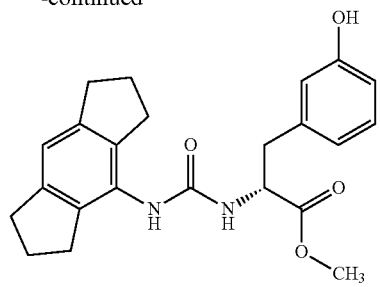

SM: methyl (2R)-2-amino-3-(3-hydroxyphenyl)propanoate hydrochloride

General Procedure A

Y=50%
MS ES+: 395.1
1H NMR (400 MHz, DMSO-d6) δ 9.33 (s, 1H), 7.89 (s, 1H), 7.08 (t, J=8 Hz, 1H), 6.87 (s, 1H), 6.66-6.61 (m, 1H), 6.61-6.56 (m, 2H), 6.30 (d, J=8 Hz, 1H), 4.48-4.43 (m, 1H), 3.64 (s, 3H), 2.97-2.93 (m, 1H), 2.90-2.85 (m, 1H), 2.79 (t, J=7 Hz, 4H), 2.68-2.60 (m, 4H), 1.98-191 (m, 4H).

2L

Methyl (2R)-2-{[(1,2,3,5,6,7-hexahydro-s-indacen-4-yl)carbamoyl]amino}-3-[3-(1H-pyrazol-3-yl)phenyl]propanoate

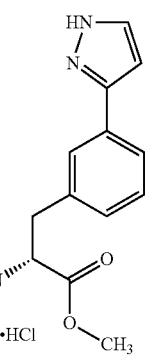

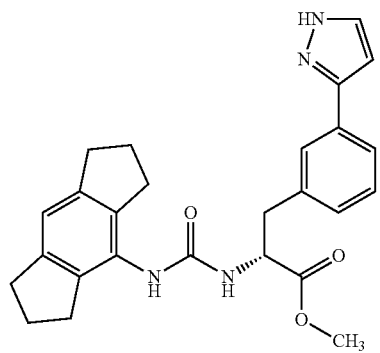

SM: methyl (2R)-2-amino-3-[3-(1H-pyrazol-5-yl)phenyl]propanoate hydrochloride

General Procedure A

The product was further purified by flash column chromatography to give the title compound.

Y=32%

MS ES+: 445

¹H NMR (400 MHz, DMSO-d6) δ 12.86 (s, 1H), 7.88-7.50 (m, 4H), 7.41-7.28 (m, 1H), 7.19-7.06 (m, 1H), 6.85 (s, 1H), 6.67 (s, 1H), 6.37 (d, J=8 Hz, 1H), 4.61-4.47 (m, 1H), 3.66 (s, 3H), 3.13-3.09 (m, 1H), 3.03-2.98 (m, 1H), 2.77 (t, J=7 Hz, 4H), 2.61 (t, J=7 Hz, 4H), 1.95-1.87 (m, 4H).

2M

Methyl(2R)-2-{[(1,2,3,5,6,7-hexahydro-s-indacen-4-yl)carbamoyl]amino}-3-[3-(hydroxymethyl)phenyl]propanoate

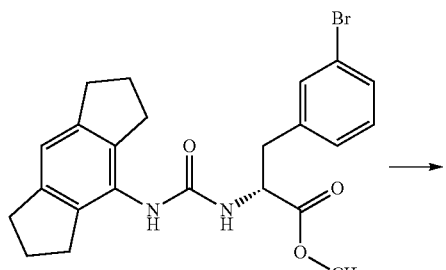

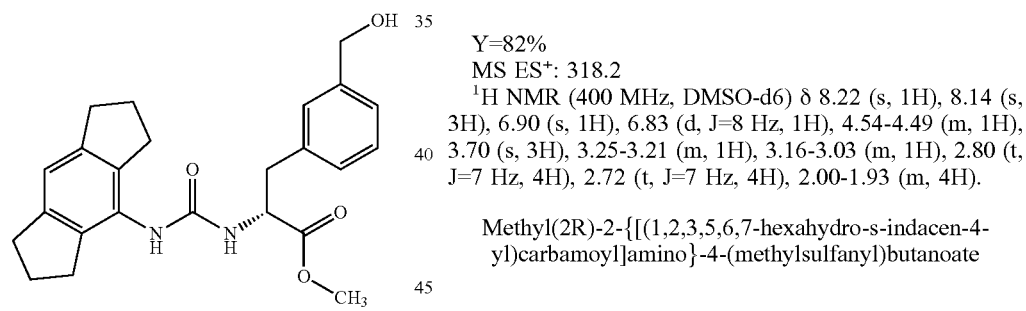

In a sealed tube (tributylstannyl)methanol (153 mg, 0.44 mmol, 1 eq.), tetrakis(triphenylphosphine)palladium(O) (25.2 mg, 0.005 mmol) and methyl (2R)-3-(3-bromophenyl)-2-{[(1,2,3,5,6,7-hexahydro-s-indacen-4-yl)carbamoyl]amino}propanoate (200 mg, 0.44 mmol) were dissolved in anhydrous dioxane under Ar atmosphere at room temperature. The reaction mixture was stirred at 80° C. for 18 h. After cooling to room temperature the reaction mixture was concentrated and purified by flash column chromatography (DCM/MeOH) to give the title compound as a yellow solid.

Y=10%

MS ES+: 409

¹H NMR (400 MHz, DMSO-d6) δ 7.86 (s, 1H), 7.26 (t, J=8 Hz, 1H), 7.19 (d, J=8 Hz, 1H), 7.13 (s, 1H), 7.05 (d, J=8 Hz, 1H), 6.87 (s, 1H), 6.34 (d, J=8 Hz, 1H), 5.16 (t, J=6 Hz, 1H), 4.52-4.43 (m, 3H), 3.64 (s, 3H), 3.06-3.02 (m, 1H), 2.98-2.93 (m, 1H), 2.79 (t, J=7 Hz, 4H), 2.64 (t, J=7 Hz, 4H), 1.98-1.91 (m, 4H).

2N

Methyl(2R)-3-amino-2-{[(1,2,3,5,6,7-hexahydro-s-indacen-4-yl)carbamoyl]amino}propanoate

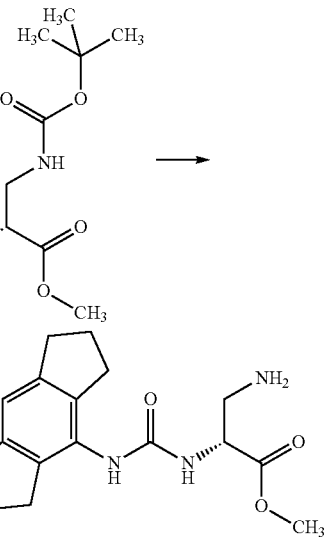

SM: methyl (2R)-3-{[(tert-butoxy)carbonyl]amino}-2-{[(1,2,3,5,6,7-hexahydro-s-indacen-4-yl)carbamoyl]amino}propanoate General Procedure C

Y=82%

MS ES+: 318.2

¹H NMR (400 MHz, DMSO-d6) δ 8.22 (s, 1H), 8.14 (s, 3H), 6.90 (s, 1H), 6.83 (d, J=8 Hz, 1H), 4.54-4.49 (m, 1H), 3.70 (s, 3H), 3.25-3.21 (m, 1H), 3.16-3.03 (m, 1H), 2.80 (t, J=7 Hz, 4H), 2.72 (t, J=7 Hz, 4H), 2.00-1.93 (m, 4H).

Methyl(2R)-2-{[(1,2,3,5,6,7-hexahydro-s-indacen-4-yl)carbamoyl]amino}-4-(methylsulfanyl)butanoate

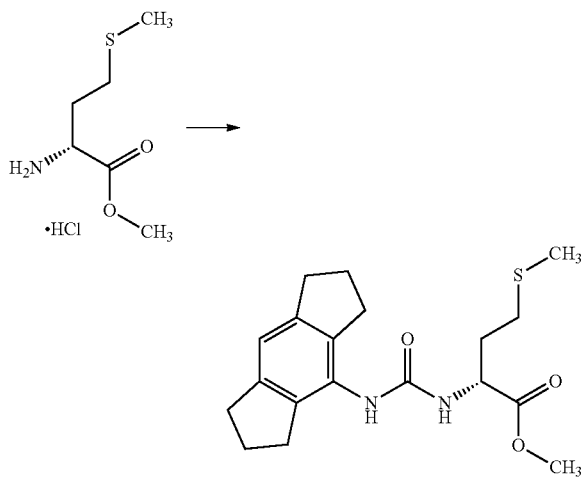

SM: D-Methionine methyl ester hydrochloride

General Procedure A

Y=72%

MS ES+: 363.2

¹H NMR (400 MHz, DMSO-d6) δ 7.78 (s, 1H), 6.88 (s, 1H), 6.52 (d, J=8 Hz, 1H), 4.35-4.30 (m, 1H), 3.66 (s, 3H), 2.79 (t, J=7 Hz, 4H), 2.68 (t, J=7 Hz, 4H), 2.06 (s, 3H), 2.00-1.85 (m, 6H).

2P

Methyl(2R)-3-(3-acetamidophenyl)-2-{[(1,2,3,5,6,7-hexahydro-s-indacen-4-yl)carbamoyl]amino}propanoate

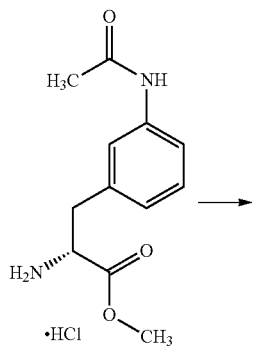

•HCl

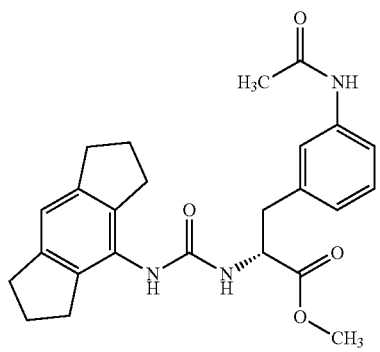

SM: methyl (2R)-2-amino-3-(3-acetamidophenyl)propanoate hydrochloride

General Procedure A

The final compound was further purified by FCC to give the title compound as a white solid.

Y=11%

MS ES+: 436.4

¹H NMR (400 MHz, DMSO-d6) δ 7.91 (s, 1H), 6.93 (t, J=8 Hz, 1H), 6.87 (s, 1H), 6.47-6.40 (m, 1H), 6.40-6.35 (m, 1H), 6.32-6.24 (m, 2H), 5.00 (s, 1H), 4.46-4.34 (m, 1H), 3.64 (s, 2H), 2.91-2.75 (m, 6H), 2.67-2.63 (m, 4H), 1.98-1.91 (m, 4H).

2Q

Methyl 2-{[(1,2,3,5,6,7-hexahydro-s-indacen-4-yl)carbamoyl]amino}-3-(1-methyl-1H-pyrazol-4-yl)propanoate

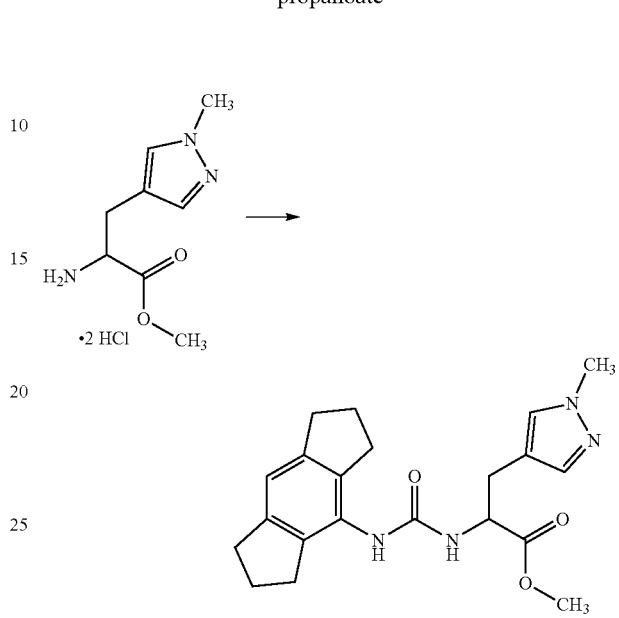

SM: methyl 2-amino-3-(1-methyl-1H-pyrazol-4-yl)propanoate dihydrochloride

General Procedure A

The final compound was further purified by FCC to give the title compound as a white solid.

Yield=5%

MS ES+: 383.3

¹H NMR (400 MHz, DMSO-d6) δ 7.91 (s, 1H), 7.45 (s, 1H), 7.22 (d, J=1 Hz, 1H), 6.88 (s, 1H), 6.30 (d, J=8 Hz, 1H), 4.45-4.35 (m, 1H), 3.79 (s, 3H), 3.66 (s, 3H), 2.91-2.82 (m, 2H), 2.79 (t, J=7 Hz, 4H), 2.67 (t, J=7 Hz, 4H), 1.99-1.92 (m, 4H).

2R

Methyl(2R)-2-{[(1,2,3,5,6,7-hexahydro-s-indacen-4-yl)carbamoyl]amino}-3-[3-(2-oxopyrrolidin-1-yl)phenyl]propanoate

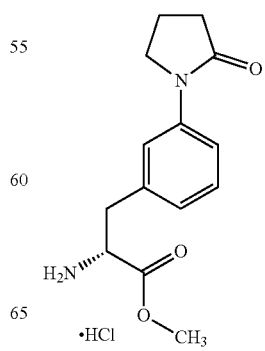

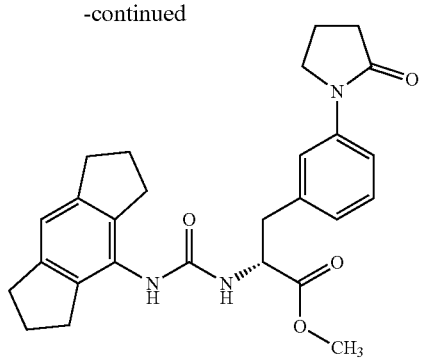

SM: methyl (2R)-2-amino-3-{3-[(2-oxocyclopentyl)amino]phenyl}propanoate

General Procedure A

The final compound was further purified by FCC to give the title compound as a white solid.
Y=38%
MS ES⁺: 462.8
¹H NMR (400 MHz, DMSO-d6) δ 7.85 (s, 1H), 7.62-7.54 (m, 1H), 7.46 (s, 1H), 7.30 (t, J=8 Hz, 1H), 6.95 (d, J=8 Hz, 1H), 6.87 (s, 1H), 6.33 (d, J=8 Hz, 1H), 4.53-4.48 (m, 1H), 3.89-3.76 (m, 2H), 3.66 (s, 3H), 3.10-2.90 (m, 2H), 2.78 (t, J=7 Hz, 4H), 2.62 (t, J=7 Hz, 4H), 2.10-2.02 (m, 2H), 1.97-1.90 (m, 4H).

2S 1,5-dimethyl(2R)-2-{[(1,2,3,5,6,7-hexahydro-s-indacen-4-yl)carbamoyl]amino}pentanedioate

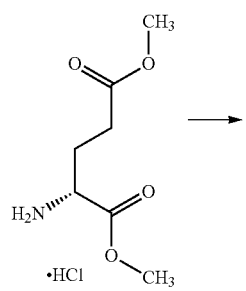

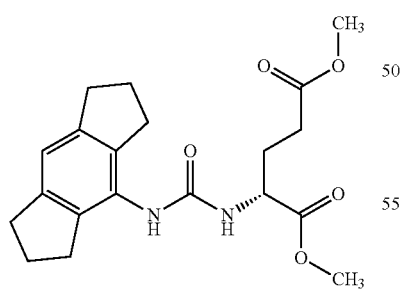

SM: 1,5-dimethyl (2R)-2-aminopentanedioate hydrochloride

General Procedure A

Y=34%
MS ES⁺: 375.2
¹H NMR (400 MHz, DMSO-d6) δ 7.80 (s, 1H), 6.88 (s, 1H), 6.49 (d, J=8 Hz, 1H), 4.28-4.22 (m, 1H), 3.65 (s, 3H), 3.60 (s, 3H), 2.80 (t, J=7 Hz, 4H), 2.68 (t, J=7 Hz, 4H), 2.45-2.35 (m, 2H), 2.05-1.92 (m, 5H), 1.91-1.80 (m, 1H).

2T

Ethyl 2-[({1H,2H,3H,6H,7H,8H,9H-cyclopenta[a]naphthalen-5-yl}carbamoyl)amino] acetate

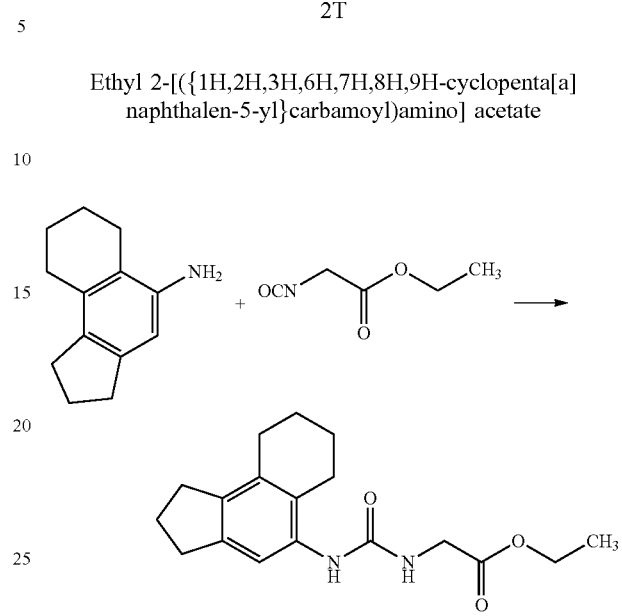

1H,2H,3H,6H,7H,8H,9H-cyclopenta[a]naphthalen-5-amine (20 mg, 0.107 mmol) was dissolved in ACN (1 ml). To this was added a solution of ethyl 2-isocyanatoacetate (17 mg, 1.2 eq., 0.128 mmol) in ACN (1 ml) and the reaction mixture stirred at room temperature overnight. The resulting precipitate was filtered, washed with ACN and dried under reduced pressure to give the title compound as a white solid.
Y=97%
MS ES⁺: 317
¹H NMR (400 MHz, DMSO-d6) δ 7.69 (s, 1H), 7.34 (s, 1H), 6.68 (t, J=6 Hz, 1H), 4.14-4.08 (m, 2H), 3.84 (d, J=6 Hz, 2H), 2.78 (t, J=8 Hz, 2H), 2.67 (t, J=7 Hz, 2H), 2.55 (t, J=5 Hz, 2H), 2.52-2.46 (m, 6H), 2.01-1.94 (m, 2H), 1.76-1.66 (m, 4H), 1.21 (t, J=7 Hz, 3H).

2U

Methyl(2R)-2-{[(1,2,3,5,6,7-hexahydro-s-indacen-4-yl)carbamoyl]amino}-3-{3-[(1H-pyrazol-3-yl)amino]phenyl}propanoate

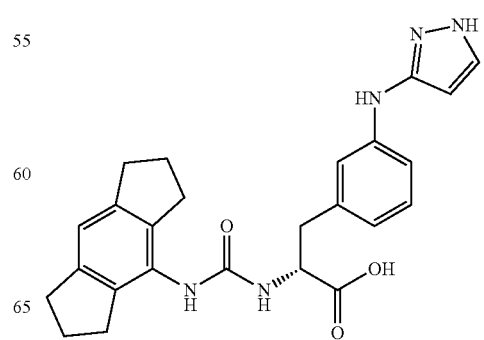

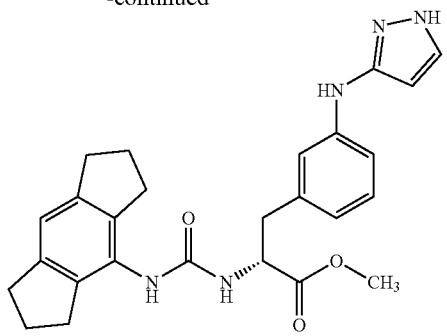

SM: (2R)-2-{[(1,2,3,5,6,7-hexahydro-s-indacen-4-yl)carbamoyl]amino}-3-{3-[(1H-pyrazol-3-yl)amino]phenyl}propanoic acid General Procedure B The product was further purified by preparative HPLC to give the desired product as a white solid.
Y=38%
MS ES⁺: 460
¹H NMR (400 MHz, DMSO-d6) δ 8.40 (s, 1H), 7.90 (s, 1H), 7.57 (d, J=2 Hz, 1H), 7.18-7.13 (m, 2H), 7.12-7.07 (m, 1H), 6.86 (s, 1H), 6.53 (d, J=7 Hz, 1H), 6.26 (d, J=8 Hz, 1H), 5.86 (d, J=2 Hz, 1H), 4.47 (m, 1H), 3.65 (s, 3H), 2.97-2.86 (m, 2H), 2.78 (t, J=7 Hz, 4H), 2.66-2.62 (m, 4H), 1.97-1.90 (m, 4H).

2V (2R)-2-{[(1,2,3,5,6,7-hexahydro-s-indacen-4-yl)carbamoyl]amino}-3-[3-(1H-pyrazol-3-yl)phenyl]propanoic acid

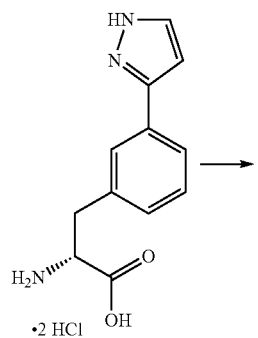

(2R)-2-amino-3-[3-(1H-pyrazol-3-yl)phenyl]propanoic acid dihydrochloride (180 mg, 0.59 mmol) was dissolved in 1 M NaOH (0.7 ml, 1.20 mmol) and cooled to 0° C. The resulting solution was then treated dropwise with a solution of intermediate A (120 mg, 0.60 mmol) in acetone (1.4 ml). After stirring at room temperature for 24 h a further portion of intermediate A (120 mg, 0.60 mmol) in acetone (1.4 ml) was added. The RM was stirred at rt for a further 24 h. The RM was filtered and the collected solid was triturated with acetone. This was further purified by preparative HPLC to give the title compound as a white powder.
Y=7%
MS ES⁺ 431.1
¹H NMR (400 MHz, DMSO-d6) δ 12.92 (s, 2H), 7.87 (s, 1H), 7.70 (s, 1H), 7.67-7.61 (m, 2H), 7.32 (t, J=8 Hz, 1H), 7.14 (d, J=8 Hz, 1H), 6.84 (s, 1H), 6.64 (d, J=2 Hz, 1H), 6.25 (d, J=8 Hz, 1H), 4.46-4.41 (m, 1H), 3.17-3.12 (m, 1H), 3.01-2.96 (m, 1H), 2.77 (t, J=7 Hz, 4H), 2.62 (t, J=7 Hz, 4H), 1.94-1.87 (m, 4H).

2W 1,4-dimethyl(2R)-2-{[(1,2,3,5,6,7-hexahydro-s-indacen-4-yl)carbamoyl]amino}butanedioate

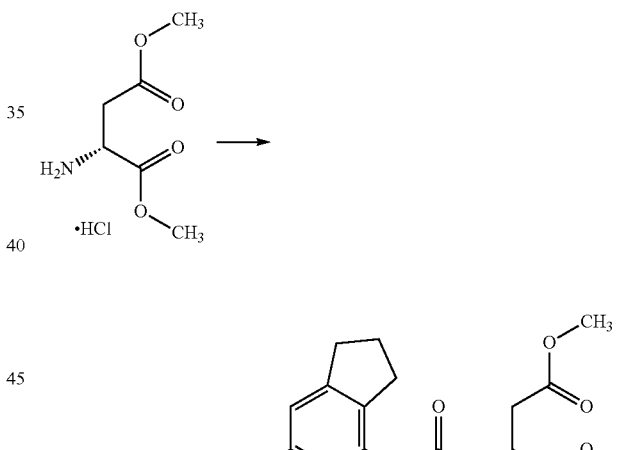

SM: 1,4-dimethyl (2R)-2-aminobutanedioate hydrochloride

General Procedure A

Y=46.7%
MS ES⁺: 361.0
¹H NMR (400 MHz, DMSO-d6) δ 8.02 (s, 1H), 6.88 (s, 1H), 6.57 (d, J=8.5 Hz, 1H), 4.64-4.54 (m, 1H), 3.65 (s, 3H), 3.63 (s, 3H), 2.87-2.74 (m, 6H), 2.67 (t, J=7.3 Hz, 4H), 2.02-1.88 (m, 4H).

2X ethyl 2-{[(1,2,3,5,6,7-hexahydro-s-indacen-4-yl)carbamoyl]amino}acetate

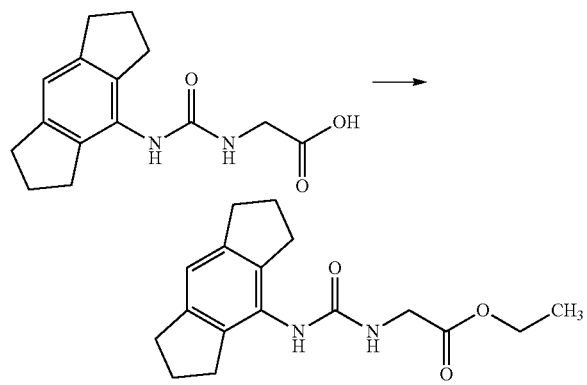

2-{[(1,2,3,5,6,7-hexahydro-s-indacen-4-yl)carbamoyl]amino}acetic acid (80 mg, 0.3 mmol) was suspended in dioxane (1 ml) and then treated with 1,1'-carbonyldiimidazole (61 mg, 0.37 mmol). After stirring at rt for 15 min ethanol (2 ml, 33.5 mmol) was added and the RM refluxed for 4 h. The RM was evaporated, triturated with water, filtered and recrystallised from boiling ethanol to give the title compound as a white powder.

Y=22%
MS ES+: 303.1
$^1$H NMR (400 MHz, DMSO) δ 7.92 (s, 1H), 6.89 (s, 1H), 6.33 (t, J=6 Hz, 1H), 4.13-4.07 (m, 2H), 3.81 (d, J=6 Hz, 2H), 2.80 (t, J=7 Hz, 4H), 2.70 (t, J=7 Hz, 4H), 2.09-1.84 (m, 4H), 1.21 (t, J=7 Hz, 3H).

2Y methyl(2R)-2-{[(1,2,3,5,6,7-hexahydro-s-indacen-4-yl)carbamoyl]amino}-3-henylpropanoate

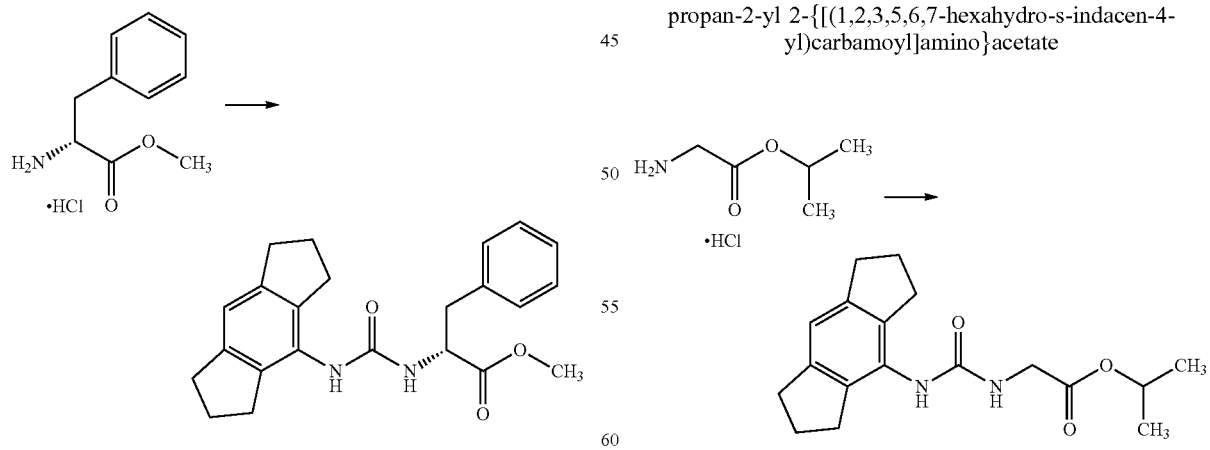

SM: methyl (2R)-2-amino-3-phenylpropanoate hydrochloride

General Procedure A

Y=44%
MS ES+: 379.1

$^1$H NMR (400 MHz, DMSO) δ 7.85 (s, 1H), 7.49-7.05 (m, 5H), 6.87 (s, 1H), 6.33 (d, J=8 Hz, 1H), 4.53-4.44 (m, 1H), 3.64 (s, 3H), 3.11-3.01 (m, 1H), 3.0-2.92 (m, 1H), 2.79 (t, J=7 Hz, 4H), 2.63 (t, J=7 Hz, 4H), 2.03-1.87 (m, 4H).

2Z methyl(2R)-2-{[(1,2,3,5,6,7-hexahydro-s-indacen-4-yl)carbamoyl]amino}-3-(4-hydroxyphenyl)propanoate

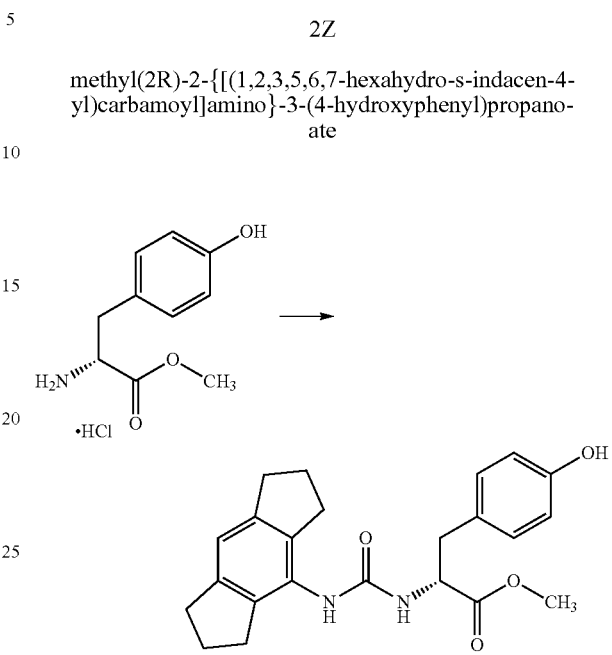

SM: methyl (2R)-2-amino-3-(4-hydroxyphenyl)propanoate hydrochloride

General Procedure A

Y=33%
MS ES+: 395.3
$^1$H NMR (400 MHz, DMSO) δ 9.25 (s, 1H), 7.86 (s, 1H), 6.96 (d, J=8 Hz, 2H), 6.87 (s, 1H), 6.68 (d, J=8 Hz, 2H), 6.24 (d, J=8 Hz, 1H), 4.44-4.37 (m, 1H), 2.96-2.83 (m, 2H), 2.79 (t, J=7 Hz, 4H), 2.64 (t, J=7 Hz, 4H), 2.0-1.90 (m, 4H).

2AA propan-2-yl 2-{[(1,2,3,5,6,7-hexahydro-s-indacen-4-yl)carbamoyl]amino}acetate SM: propan-2-yl 2-aminoacetate hydrochloride General Procedure A

Y=58%
MS ES+: 317.2

¹H NMR (400 MHz, DMSO) δ 7.91 (s, 1H), 6.89 (s, 1H), 6.32 (t, J=6 Hz, 1H), 4.97-4.88 (m, 1H), 3.78 (d, J=6 Hz, 2H), 2.80 (t, J=7 Hz, 4H), 2.71 (t, J=7 Hz, 4H), 2.0-1.92 (m, 4H), 1.22 (d, J=6 Hz, 6H).

2BB methyl(2R)-3-carbamoyl-2-{[(1,2,3,5,6,7-hexahydro-s-indacen-4yl) carbamoyl]amino}propanoate

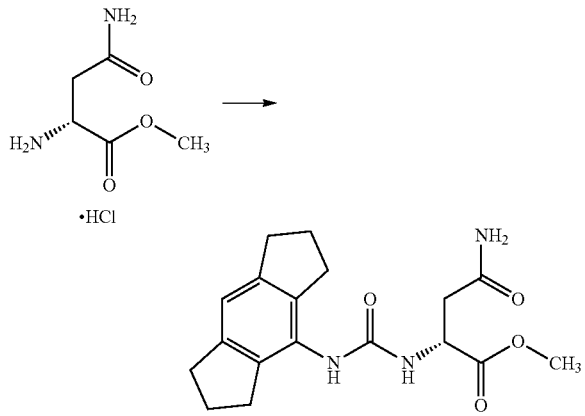

SM: methyl (2R)-2-amino-3-carbamoylpropanoate hydrochloride

General Procedure A

Y=50%
MS ES⁺: 346.1
¹H NMR (400 MHz, DMSO) δ 8.07 (s, 1H), 7.46 (s, 1H), 6.96 (s, 1H), 6.87 (s, 1H), 6.44 (d, J=8 Hz, 1H), 4.50 (s, 1H), 3.62 (s, 3H), 2.79 (t, J=7 Hz, 4H), 2.74-2.64 (m, 5H), 2.56 (d, J=4 Hz, 1H), 2.04-1.89 (m, 4H).

2CC methyl (2R)-2-{[(1,2,3,5,6,7-hexahydro-s-indacen-4-yl)carbamoyl]amino}-3-(thiophen-2-yl)propanoate

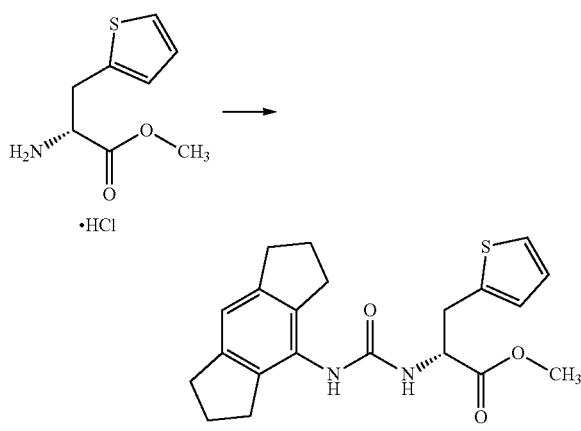

SM: methyl (2R)-2-amino-3-(thiophen-2-yl)propanoate hydrochloride

General Procedure A

Y=81%
MS ES⁺: 385.1
¹H NMR (400 MHz, DMSO) δ 7.99 (s, 1H), 7.41-7.38 (m, 1H), 7.0-6.97 (m, 1H), 6.88 (s, 2H), 6.43 (d, J=8 Hz, 1H), 4.55-4.48 (m, 1H), 3.67 (s, 3H), 3.31-3.20 (m, 2H), 2.80 (t, J=7 Hz, 4H), 2.68 (t, J=7 Hz, 4H), 2.00-1.92 (m, 4H).

2DD methyl 2-{[(1,2,3,5,6,7-hexahydro-s-indacen-4-yl)carbamoyl]amino}-3-(1H-imidazol-1-yl)propanoate

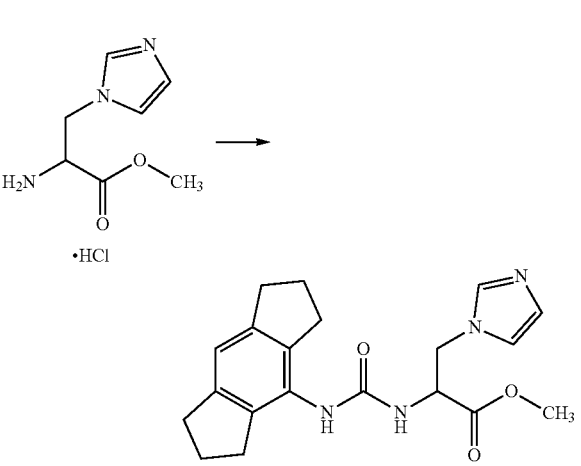

SM: methyl 2-amino-3-(1H-imidazol-1-yl)propanoate hydrochloride

General Procedure A

Y=64%
MS ES⁺: 369.2
¹H NMR (400 MHz, DMSO) δ 7.97 (s, 1H), 7.53 (s, 1H), 7.07 (s, 1H), 6.90 (d, J=4 Hz, 2H), 6.51 (d, J=8 Hz, 1H), 4.65-4.55 (m, 1H), 4.46-4.27 (m, 2H), 3.69 (s, 3H), 2.80 (t, J=7 Hz, 4H), 2.67 (t, J=7 Hz, 4H), 2.00-1.93 (m, 4H).

2EE methyl 2-{[(1,2,3,5,6,7-hexahydro-s-indacen-4-yl)carbamoyl]amino}acetate

SM: Intermediate A and methyl 2-aminoacetate hydrochloride

General Procedure A

Y=68%
MS ES+: 289.0
1H NMR (400 MHz, DMSO) δ 7.92 (s, 1H), 6.89 (s, 1H), 6.34 (t, J=6 Hz, 1H), 3.84 (d, J=6 Hz, 2H), 3.64 (s, 3H), 2.80 (t, J=7 Hz, 4H), 2.70 (t, J=7 Hz, 4H), 2.09-1.84 (m, 4H).

2FF (2S)-2-{[(1,2,3,5,6,7-hexahydro-s-indacen-4-yl)carbamoyl]amino}-3-phenylpropanoic acid

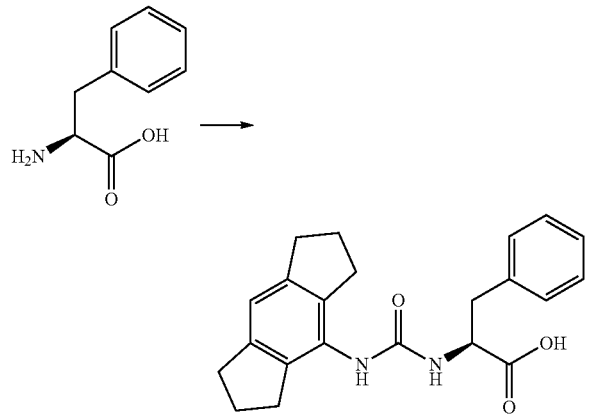

SM: (2S)-2-amino-3-phenylpropanoic acid

General Procedure A

Y=62%
MS ES+: 365.1;
1H NMR (400 MHz, DMSO-d6) δ 12.76 (s, 1H), 7.88 (s, 1H), 7.36-7.26 (m, J=7 Hz, 2H), 7.27-7.17 (m, 3H), 6.86 (s, 1H), 6.23 (d, J=8 Hz, 1H), 4.49-4.39 (m, 1H), 3.13-3.05 (m, 1H), 2.98-2.90 (m, 1H), 2.79 (t, J=7 Hz, 4H), 2.65 (t, J=7 Hz, 4H), 2.00-1.90 (m, 4H).

2GG methyl 2-{[(1,2,3,5,6,7-hexahydro-s-indacen-4-yl)carbamoyl]amino}-3-phenylpropanoate

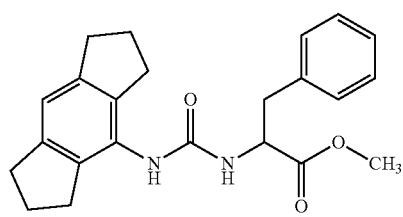 [SMILES: COC(=O)C(Cc1ccccc1)NC(=O)Nc1c2c(cc3c1CCC3)CCC2]

Mixture of: methyl (2R)-2-{[(1,2,3,5,6,7-hexahydro-s-indacen-4-yl)carbamoyl]amino}-3-phenylpropanoate and methyl (2S)-2-{[(1,2,3,5,6,7-hexahydro-s-indacen-4-yl)carbamoyl]amino}-3-phenylpropanoate

2HH methyl(2R)-3-(3-aminophenyl)-2-{[(1,2,3,5,6,7-hexahydro-s-indacen-4yl) carbamoyl] amino}propanoate

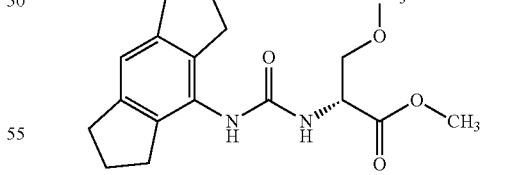

SM: Intermediate A and methyl (2R)-2-amino-3-(3-acetamidophenyl)propanoate

General Procedure A

Y=10%
MS ES+: 394.7
1H NMR (400 MHz, DMSO-d6) δ 7.91 (s, 1H), 6.93 (t, J=8 Hz, 1H), 6.87 (s, 1H), 6.47-6.40 (m, 1H), 6.40-6.35 (m, 1H), 6.34-6.23 (m, 2H), 5.00 (s, 1H), 4.46-4.34 (m, 1H), 3.64 (s, 2H), 2.91-2.75 (m, 6H), 2.65 (t, J=7.8 Hz, 4H), 2.01-1.89 (m, 4H).

2II methyl(2R)-2-{[(1,2,3,5,6,7-hexahydro-s-indacen-4-yl)carbamoyl]amino}-3-methoxypropanoate SM: Methyl (2R)-2-amino-3-methoxypropanoate hydrochloride General Procedure A Y=75%
MS ES+: 333.1
1H NMR (400 MHz, DMSO-d6) δ 7.99 (s, 1H), 6.87 (s, 1H), 6.51 (d, J=9 Hz, 1H), 4.45-4.37 (m, 1H), 3.77-3.70 (m, 1H), 3.66 (s, 3H), 3.61-3.52 (m, 1H), 3.28 (s, 3H), 2.79 (t, J=7 Hz, 4H), 2.68 (t, J=7 Hz, 4H), 2.03-1.89 (m, 4H).

2JJ methyl(2R)-2-{[(1,2,3,5,6,7-hexahydro-s-indacen-4-yl)carbamoyl]amino}-3-hydroxypropanoate

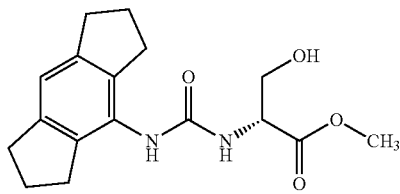 [SMILES: COC(=O)[C@@H](CO)NC(=O)Nc1c2c(cc3c1CCC3)CCC2]

SM: methyl (2R)-2-amino-3-hydroxypropanoate hydrochloride

General Procedure A

The compound was further purified by trituration in a minimum amount of DMSO. The resulting solid was filtered, washed sequentially with ACN and Et$_2$O and dried under vacuum to give the title compound as a white powder.
Y=68%
MS ES$^+$: 319.1
$^1$H NMR (400 MHz, DMSO-d6) δ 8.04 (s, 1H), 6.88 (s, 1H), 6.46 (d, J=8 Hz, 1H), 5.17 (t, J=4 Hz, 2H), 4.36-4.19 (m, 1H), 3.90-3.73 (m, 1H), 3.66 (s, 3H), 2.80 (t, J=6 Hz, 4H), 2.75-2.63 (m, 4H), 2.05-1.88 (m, 4H).

2KK ethyl (2R)-2-{[(1,2,3,5,6,7-hexahydro-s-indacen-4-yl)carbamoyl]amino}-3-[3-(1H-pyrazol-4-yl)phenyl]propanoate

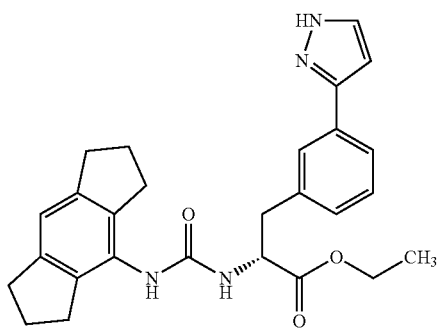

SM: Ethyl (2R)-2-amino-3-[3-(1H-pyrazol-3-yl)phenyl]propanoate hydrochloride

General Procedure A

The compound was further purified by preparative TLC (hexane:ethyl acetate 4:1) to give the title compound as a yellow solid.
Y=1%
MS ES$^+$: 459.2

$^1$H NMR (400 MHz, DMSO-d6) δ 12.93 (broad s, 1H), 8.24 (broad s, 1H), 7.76-7.59 (m, 3H), 7.33 (t, J=8 Hz, 1H), 7.14 (d, J=8 Hz, 1H), 6.84 (s, 1H), 6.80 (broad s, 1H), 6.67 (d, J=2 Hz, 1H), 4.52-4.41 (m, 1H), 4.14-4.03 (m, 2H), 3.12-2.96 (m, 2H), 2.77 (t, J=7 Hz, 4H), 2.62 (t, J=7 Hz, 4H), 1.98-1.90 (m, 4H), 1.16 (t, J=7 Hz, 3H).

2LL (2R)-2-{[(1,2,3,5,6,7-hexahydro-s-indacen-4-yl)carbamoyl]amino}-3-(pyridin-3-yl)propanoic acid

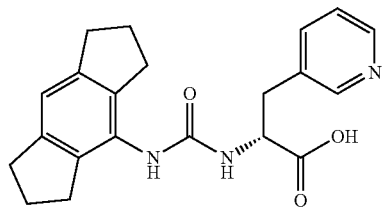 [SMILES: O=C(Nc1c2c(cc3c1CCC3)CCC2)N[C@H](Cc1cccnc1)C(=O)O]

To a suspension of (2R)-2-amino-3-(pyridin-3-yl)propanoic acid (200 mg, 1.2 mmol, 1 eq.) in acetone/H2O (1:1, 8 ml) was added Et$_3$N (252 μl, 1.8 mmol, 1.5 eq.), and the mixture was stirred for 5 min. A solution of intermediate A (264 mg, 1.3 mmol, 1.1 eq.) in THF (2 mL) was added and the reaction mixture stirred overnight at rt. The volume of the mixture was reduced to half in vacuo and the resulting white precipitate filtered off, washed sequentially with water, ACN and Et$_2$O and dried under vacuum to give the title compound as a white powder.
Y=68%
MS ES$^+$: 366.3
$^1$H NMR (400 MHz, DMSO-d6) δ 12.91 (s, 1H), 8.44 (d, J=4 Hz, 1H), 8.41 (s, 1H), 7.86 (s, 1H), 7.61 (d, J=7 Hz, 1H), 7.37-7.29 (m, 1H), 6.86 (s, 1H), 6.32 (d, J=8 Hz, 1H), 4.50-4.38 (m, 1H), 3.18-3.06 (m, 1H), 3.01-2.91 (m, 1H), 2.78 (t, J=7 Hz, 4H), 2.63 (t, J=7 Hz, 4H), 1.98-1.90 (m, 4H).

2MM 2-methoxyethyl(2R)-2-{[(1,2,3,5,6,7-hexahydro-s-indacen-4-yl)carbamoyl]amino}-3-(pyridin-3-yl)propanoate

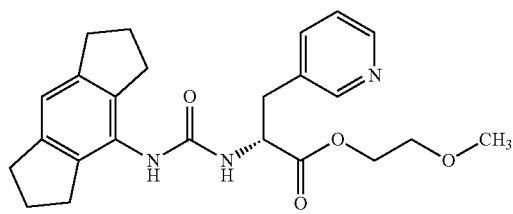 [SMILES: COCCOC(=O)[C@@H](Cc1cccnc1)NC(=O)Nc1c2c(cc3c1CCC3)CCC2]

SM: 2-methoxyethyl (2R)-2-amino-3-(pyridine-3-yl)propanoate hydrochloride

General Procedure A

Y=28%
MS ES$^+$: 424.5

$^1$H NMR (400 MHz, DMSO-d6) δ 8.47-8.44 (m, 1H), 8.42 (d, J=2 Hz, 1H), 7.92 (s, 1H), 7.68-7.59 (m, 1H), 7.38-7.30 (m, 1H), 6.87 (s, 1H), 6.50 (d, J=8 Hz, 1H), 4.58-4.49 (m, 1H), 4.26-4.14 (m, 2H), 3.59-3.48 (m, 2H), 3.28 (s, 3H), 3.14-3.06 (m, 1H), 3.05-2.96 (m, 1H), 2.79 (t, J=7 Hz, 4H), 2.62 (t, J=7 Hz, 4H), 1.98-1.90 (m, 4H).

2NN cyclobutyl (2R)-2-{[(1,2,3,5,6,7-hexahydro-s-indacen-4-yl)carbamoyl]amino}-3-(pyridin-3-yl)propanoate

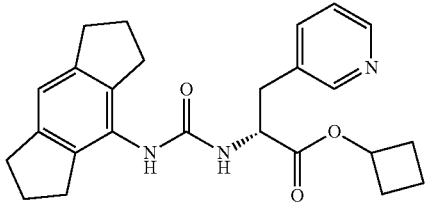 [SMILES: O=C(Nc1c2c(cc3c1CCC3)CCC2)N[C@H](Cc1cccnc1)C(=O)OC1CCC1]

SM: Cyclobutyl (2R)-2-amino-3-(pyridine-3-yl)propanoate

General Procedure A

The crude product was further purified by preparative HPLC (HCOOH buffer) to give the title compound as a white solid.
Y=2%
MS ES+: 420.4
$^1$H NMR (400 MHz, DMSO-d6) δ 8.51-8.35 (m, 2H), 7.91 (s, 1H), 7.68-7.59 (m, 1H), 7.38-7.29 (m, 1H), 6.87 (s, 1H), 6.49 (d, J=8 Hz, 1H), 4.96-4.85 (m, 1H), 4.50-4.39 (m, 1H), 3.12-3.04 (m, 1H), 3.04-2.95 (m, 1H), 2.78 (t, J=7 Hz, 4H), 2.63 (t, J=7 Hz, 4H), 2.30-2.20 (m, 2H), 1.99-1.89 (m, 4H), 1.80-1.68 (m, 1H), 1.67-1.52 (m, 1H).

2OO cyclopropylmethyl(2R)-2-{[(1,2,3,5,6,7-hexahydro-s-indacen-4-yl)carbamoyl]amino}-3-(pyridin-3-yl)propanoate

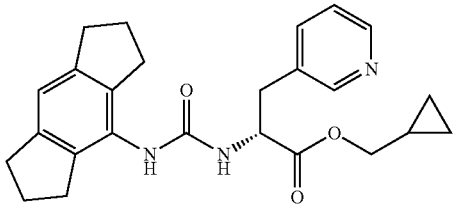 [SMILES: O=C(Nc1c2c(cc3c1CCC3)CCC2)N[C@H](Cc1cccnc1)C(=O)OCC1CC1]

SM: Cyclopropylmethyl (2R)-2-amino-3-(pyridine-3-yl)propanoate

General Procedure A

The product was purified by preparative HPLC (HCOOH buffer) to give the title compound as a white solid.
Y=8%
MS ES+: 420.4

$^1$H NMR (400 MHz, DMSO-d6) δ 8.48-8.40 (m, 2H), 7.93 (s, 1H), 7.64 (d, J=8 Hz, 1H), 7.38-7.29 (m, 1H), 6.87 (s, 1H), 6.51 (d, J=8 Hz, 1H), 4.56-4.47 (m, 1H), 3.91 (d, J=7 Hz, 2H), 3.13-3.05 (m, 1H), 3.05-2.97 (m, 1H), 2.78 (t, J=7 Hz, 4H), 2.63 (t, J=7 Hz, 4H), 2.02-1.85 (m, 4H), 1.13-0.99 (m, 1H), 0.56-0.47 (m, 2H), 0.34-0.21 (m, 2H).

2PP cyclopentyl(2R)-2-{[(1,2,3,5,6,7-hexahydro-s-indacen-4-yl)carbamoyl]amino}-3-(pyridin-3-yl)propanoate

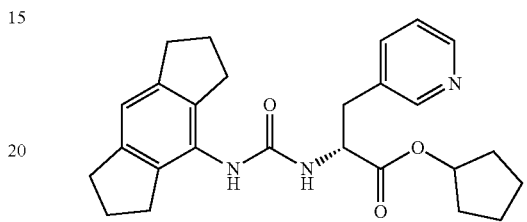

SM: Cyclopentyl (2R)-2-amino-3-(pyridine-3-yl)propanoate ditrifluoromethanesulfonic acid salt General Procedure A The crude product was purified by preparative HPLC (HCOOH buffer) to give the title compound as a white solid.
Y=9%
MS ES+: 434.5
$^1$H NMR (400 MHz, DMSO-d6) δ 8.45 (d, J=5 Hz, 1H), 8.43-8.38 (m, 1H), 7.85 (s, 1H), 7.63 (d, J=8 Hz, 1H), 7.40-7.29 (m, 1H), 6.88 (s, 1H), 6.42 (d, J=8 Hz, 1H), 5.12-5.03 (m, 1H), 4.47-4.37 (m, 1H), 3.11-2.94 (m, 2H), 2.79 (t, J=7 Hz, 4H), 2.63 (d, J=7 Hz, 4H), 1.95 2.02-1.88 (m, 4H), 1.87-1.72 (m, 2H), 1.67-1.46 (m, 6H).

2Q methyl(2R)-3-cyano-2-{[(1,2,3,5,6,7-hexahydro-s-indacen-4yl)carbamoyl]amino}propanoate

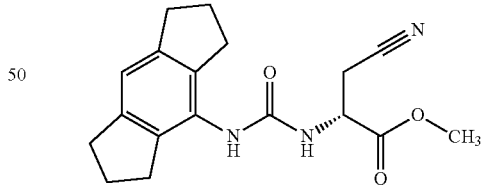

Methyl (2R)-3-carbamoyl-2-{[(1,2,3,5,6,7-hexahydro-s-indacen-4-yl)carbamoyl]amino}propanoate (Example 2BB) (103 mg, 0.3 mmol, 1 eq.) was suspended in anhydrous DCM (3 ml). Para-tosyl chloride (239 mg, 1.2 mmol, 4.2 eq.) was added, followed by pyridine (240 al, 3 mmol, 10 eq.) and the RM stirred at rt under argon for 72 h. The RM was evaporated and the resulting solid washed sequentially with DCM, H$_2$O and Et$_2$O. The crude was purified by preparative HPLC (formic acid buffer) to give the title compound.
Y=13%
MS ES+: 350.3 [M+Na]+

¹H NMR (400 MHz, DMSO-d6) δ 8.09 (s, 1H), 6.90 (s, 1H), 6.82 (d, J=8 Hz, 1H), 4.61-4.53 (m, 1H), 3.69 (s, 3H), 3.11-2.95 (m, 2H), 2.80 (t, J=7 Hz, 4H), 2.70 (t, J=7 Hz, 4H), 2.91-1.93 (m, J=7 Hz, 4H).

2RR ethyl(2R)-2-{[(1,2,3,5,6,7-hexahydro-s-indacen-4-yl)carbamoyl]amino}-3-(pyridin-3-yl)propanoate

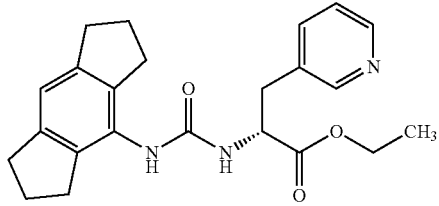 [SMILES: CCOC(=O)[C@@H](Cc1cccnc1)NC(=O)Nc1c2c(cc3c1CCC3)CCC2]

SM: (2R)-2-amino-3-(pyridin-3-yl)propanoic acid hydrochloride

General Procedure A

Y=69%

MS ES⁺: 394.5

¹H NMR (400 MHz, DMSO-d6) δ 8.45 (d, J=3 Hz, 2H), 8.42 (s, 1H), 7.88 (s, 1H), 7.63 (d, J=7 Hz, 1H), 7.37-7.28 (m, 1H), 6.87 (s, 1H), 6.46 (d, J=8 Hz, 1H), 4.54-4.41 (m, 1H), 4.15-4.07 (m, 1H), 3.14-2.94 (m, 2H), 2.79 (t, J=7 Hz, 4H), 2.62 (t, J=7 Hz, 4H), 1.98-1.90 (m, J=7 Hz, 4H), 1.17 (t, J=7 Hz, 3H).

2SS (2R)-2-{[(1,2,3,5,6,7-hexahydro-s-indacen-4-yl)carbamoyl]amino}-3-phenylpropanoic acid

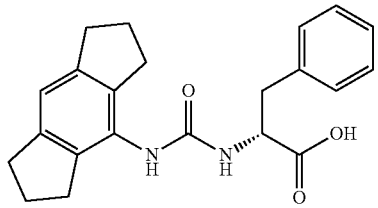 [SMILES: O=C(Nc1c2c(cc3c1CCC3)CCC2)N[C@H](Cc1ccccc1)C(=O)O]

Methyl (2R)-2-{[(1,2,3,5,6,7-hexahydro-s-indacen-4-yl)carbamoyl]amino}-3-phenylpropanoate[Intermediate 2Y] (31 mg, 0.08 mmol) was dissolved in MeOH (2 ml) and water (2 ml) then treated with LiOH.H2O (6 mg, 0.14 mmol). The RM was stirred at rt for 18 h.

2TT

Methyl 2-{[(1,2,3,5,6,7-hexahydro-s-indacen-4-yl)carbamoyl]amino}-3-(4-methyl-1H-pyrazol-1-yl)propanoate

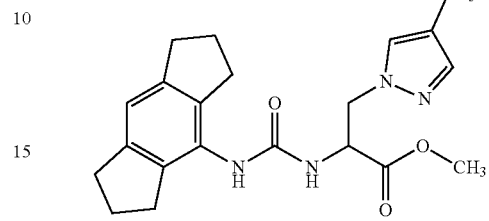

SM: methyl 2-amino-3-(4-methyl-1H-pyrazol-1-yl)propanoate hydrochloride

General Procedure A

Y=13%

MS ES⁺: 383.3

¹H NMR (400 MHz, DMSO-d6) δ 8.05 (s, 1H), 7.38 (t, J=1 Hz, 1H), 7.26 (t, J=1 Hz, 1H), 6.89 (s, 1H), 6.36 (d, J=8 Hz, 1H), 4.67-4.58 (m, 1H), 4.50-4.35 (m, 2H), 3.66 (s, 3H), 2.80 (t, J=7 Hz, 4H), 2.66 (t, J=7 Hz, 4H), 2.03-1.89 (m, 7H)

2UU

Ethyl (2R)-2-({[2,6-bis(propan-2-yl)phenyl]carbamoyl}amino)-3-(pyridin-3-yl)propanoate

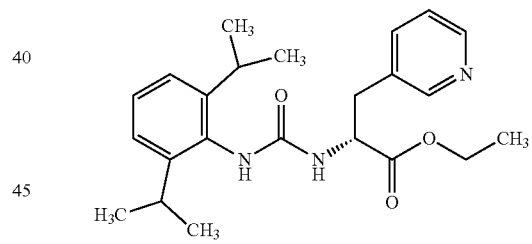

A vial was charged with methyl (2R)-2-amino-3-(3-cyanophenyl)propanoate hydrochloride (50 mg, 0.217 mol), 4-N,N-dimethylaminopyridine (approx. 2 mg) and MeCN (1 ml). A solution of 2,6-diisopropylphenylisocyanate (43 mg, 0.217 mmol) in MeCN (1 ml) was added followed by triethylamine (0.076 ml, 0.54 mmol). The vial was sealed and stirred at rt for 18 h. The resulting solution was diluted with DCM, washed with water, dried over Na₂SO₄ and evaporated. The crude product was purified by FCC (silica, 0-100% EtOAc in hexane) to give the desired product as a white solid.

Y=48%

MS ES⁺: 398.3

¹H NMR (400 MHz, DMSO-d6) δ 8.45 (d, J=5 Hz, 2H), 7.64 (d, J=7 Hz, 1H), 7.57 (s, 1H), 7.40-7.30 (m, 1H), 7.19 (t, J=8 Hz, 1H), 7.10 (s, 1H), 7.08 (s, 1H), 6.55 (d, J=7 Hz, 1H), 4.55-4.45 (m, 1H), 4.09 (q, J=7 Hz, 2H), 3.19-3.05 (m, 2H), 3.05-2.95 (m, 2H), 1.17 (t, J=7 Hz, 3H), 1.09 (d, J=6 Hz, 12H).

2VV

Ethyl 2-{[(1,2,3,5,6,7-hexahydro-s-indacen-4-yl)carbamoyl]amino}-3-(pyrimidin-2-yl)propanoate

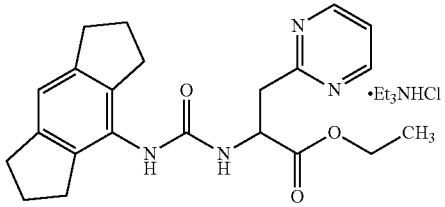

SM: ethyl 2-amino-3-(pyrimidin-2-yl)propanoate dihydrochloride

General Procedure A

Y=43%

MS ES+: 395.5

¹H NMR (400 MHz, DMSO-d6) δ 9.77 (s, 1H), 8.74 (d, J=5 Hz, 2H), 7.94 (s, 1H), 7.39 (t, J=5 Hz, 1H), 6.87 (s, 1H), 6.51 (d, J=9 Hz, 1H), 4.83-4.72 (m, 1H), 4.10-4.00 (m, 3H), 3.13-3.02 (m, 6H), 2.78 (t, J=7 Hz, 4H), 2.66-2.58 (m, 4H), 2.00-1.86 (m, 4H), 1.19 (t, J=7 Hz, 9H), 1.10 (t, J=7 Hz, 3H). Complexed with triethylamine hydrochloride.

2WW

Methyl (2R)-2-{[(1,2,3,5,6,7-hexahydro-s-indacen-4-yl)carbamoyl]amino}-3-(5-methoxypyridin-3-yl)propanoate

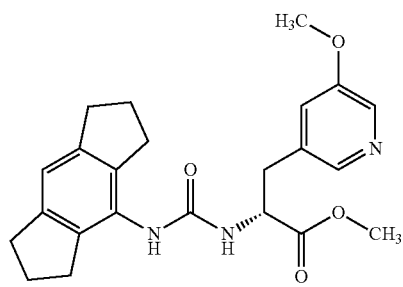 [SMILES: COC(=O)[C@@H](Cc1cncc(OC)c1)NC(=O)Nc1c2c(cc3c1CCC3)CCC2]

SM: methyl (2R)-2-amino-3-(5-methoxypyridin-3-yl)propanoate dihydrochloride

General Procedure A

The product was purified by acidic preparative HPLC, then further purified by preparative TLC (silica, 9:1 DCM/MeOH isocratic).

Y=15%

MS ES+: 410.5

¹H NMR (300 MHz, CDCl₃) δ 8.19 (s, 1H), 7.91 (s, 1H), 7.05 (s, 1H), 6.96 (s, 1H), 5.85 (s, 1H), 4.92-4.82 (m, 2H), 3.82 (s, 3H), 3.75 (s, 3H), 3.23-3.15 (m, 1H), 3.05-2.97 (m, 1H), 2.89 (t, J=8 Hz, 4H), 2.77-2.67 (m, 4H), 2.10-2.00 (m, 4H)

2XX

Ethyl 2-{[(1,2,3,5,6,7-hexahydro-s-indacen-4-yl)carbamoyl]amino}-3-(3-methyl-1,2,4-oxadiazol-5-yl)propanoate

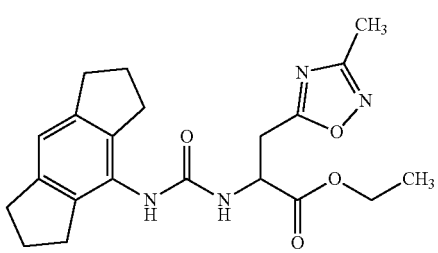 [SMILES: CCOC(=O)C(Cc1nc(C)no1)NC(=O)Nc1c2c(cc3c1CCC3)CCC2]

SM: ethyl 2-amino-3-(3-methyl-1,2,4-oxadiazol-5-yl)propanoate hydrochloride

General Procedure A

The crude product was purified by acidic preparative HPLC to give the desired product.

Y=23%

MS ES+: 399.5

¹H NMR (400 MHz, DMSO-d6) δ 8.00 (s, 1H), 6.89 (s, 1H), 6.61 (d, J=8 Hz, 1H), 4.75-4.67 (m, 1H), 4.16-4.07 (m, 2H), 3.46-3.35 (m, 2H), 2.79 (t, J=7 Hz, 4H), 2.65 (t, J=7 Hz, 4H), 2.32 (s, 3H), 2.01-1.90 (m, 4H), 1.17 (t, J=7 Hz, 3H)

2YY

Methyl (2R)-2-{[(1,2,3,5,6,7-hexahydro-s-indacen-4-yl)carbamoyl]amino}-3-(pyridazin-3-yl)propanoate

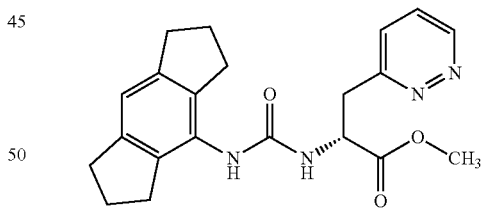

SM: methyl (2R)-2-amino-3-(pyridazin-3-yl)propanoate hydrochloride

General Procedure A

The crude product was purified by acidic preparative HPLC to give the desired product as a white solid.

Y=23%

MS ES+: 381.4

¹H NMR (400 MHz, DMSO-d6) δ 9.12 (dd, J=5, 2 Hz, 1H), 7.90 (s, 1H), 7.66-7.58 (m, 2H), 6.86 (s, 1H), 6.53 (d, J=8 Hz, 1H), 4.76-4.71 (m, 1H), 3.63 (s, 3H), 3.44-3.32 (m, 2H), 2.79-2.75 (m, 4H), 2.60-2.56 (m, 4H), 1.96-1.89 (m, 4H)

2ZZ

Ethyl 2-{[(1,2,3,5,6,7-hexahydro-s-indacen-4-yl)carbamoyl]amino}-3-(1,2-oxazol-4-yl)propanoate

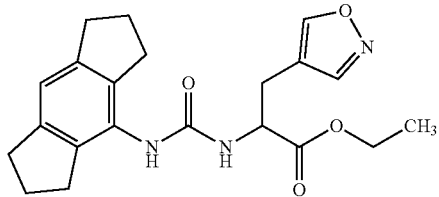 [SMILES: CCOC(=O)C(Cc1cnoc1)NC(=O)Nc1c2c(cc3c1CCC3)CCC2]

SM: ethyl 2-amino-3-(1,2-oxazol-4-yl)propanoate hydrochloride

General Procedure A

The crude product was purified by acidic preparative HPLC to give the desired product as a white solid.

Y=16%

MS ES+: 384.8

¹H NMR (400 MHz, DMSO-d6) δ 8.73 (s, 1H), 8.47 (s, 1H), 7.88 (s, 1H), 6.88 (s, 1H), 6.49 (d, J=8 Hz, 1H), 4.49-4.40 (m, 1H), 4.11 (q, J=8 Hz, 2H), 2.97-2.84 (m, 2H), 2.81-2.78 (m, 4H), 2.68-2.64 (m, 4H), 1.99-1.92 (m, 4H), 1.19 (t, J=8 Hz, 3H)

2AB

Ethyl 2-{[(1,2,3,5,6,7-hexahydro-s-indacen-4-yl)carbamoyl]amino}-3-(1,2-oxazol-3-yl)propanoate

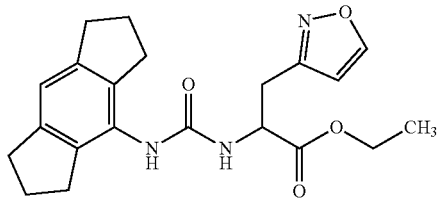 [SMILES: CCOC(=O)C(Cc1ccon1)NC(=O)Nc1c2c(cc3c1CCC3)CCC2]

SM: ethyl 2-amino-3-(1,2-oxazol-3-yl)propanoate hydrochloride

General Procedure A

Y=66%

MS ES+: 384

¹H NMR (400 MHz, DMSO-d6) δ 8.85 (d, J=2 Hz, 1H), 7.95 (s, 1H), 6.88 (s, 1H), 6.51-6.48 (m, 2H), 4.62-4.53 (m, 1H), 4.17-4.06 (m, 2H), 3.19-3.06 (m, 2H), 2.81-2.78 (m, 4H), 2.68-2.64 (m, 4H), 2.00-1.89 (m, 4H), 1.18 (t, J=7 Hz, 3H)

2AC

Ethyl 2-{[(1,2,3,5,6,7-hexahydro-s-indacen-4-yl)carbamoyl]amino}-3-(1,3-oxazol-2-yl)propanoate

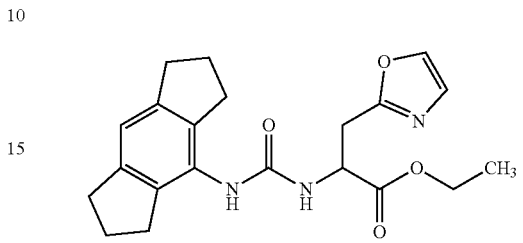

SM: ethyl 2-amino-3-(1,3-oxazol-2-yl)propanoate hydrochloride

General Procedure A

Y=21%

MS ES+: 384.4

¹H NMR (400 MHz, DMSO-d6) δ 8.05 (s, 1H), 8.03 (s, 1H), 7.15 (s, 1H), 6.88 (s, 1H), 6.53 (d, J=8 Hz, 1H), 4.69-4.63 (m, 1H), 4.14-4.04 (m, 2H), 3.23 (d, J=6 Hz, 2H), 2.82-2.76 (m, 4H), 2.68-2.63 (m, 4H), 1.99-1.90 (m, 4H), 1.16 (t, J=7 Hz, 3H)

2AD

Ethyl (2R)-2-({[6-(propan-2-yl)-2,3-dihydro-1H-inden-5-yl]carbamoyl}amino)-3-(pyridin-3-yl)propanoate

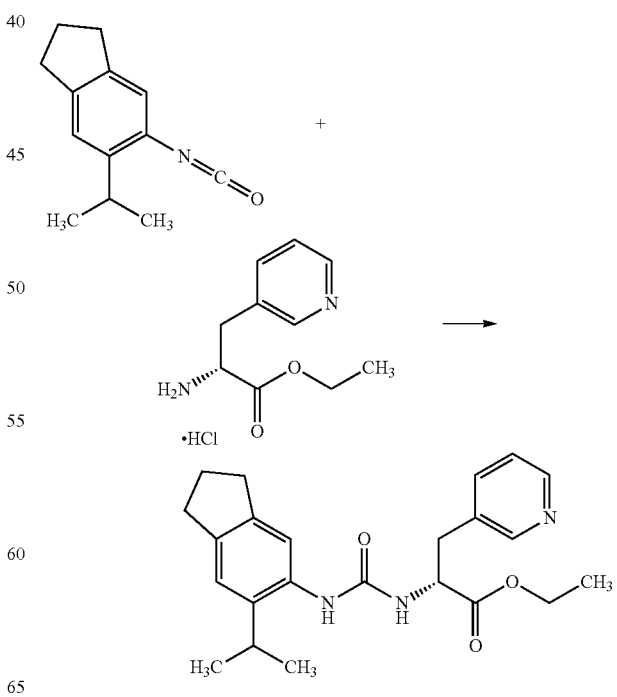

A solution of 5-isocyanato-6-(propan-2-yl)-2,3-dihydro-1H-indene (30 mg, 0.15 mmol), ethyl (2R)-2-amino-3-

(pyridin-3-yl)propanoate hydrochloride (34 mg, 0.15 mmol) and DMAP (small spatula end) in acetonitrile (3 ml) was treated with triethylamine (52 µl, 0.37 mmol). The RM was stirred at rt for 16 h. The RM was concentrated, diluted with 1M HCl and extracted with DCM. The organic phase was dried over sodium sulfate and evaporated. The resulting solid was suspended in hexane, filtered and washed with Et$_2$O. The crude product was further purified by prep TLC (silica, EtOAc/hexane) to give the desired product.
Y=22%
MS ES$^+$: 396.2
$^1$H NMR (400 MHz, DMSO-d6) δ 8.52-8.48 (m, 2H), 7.77-7.72 (m, 2H), 7.46-7.40 (m, 1H), 7.25 (s, 1H), 7.07 (s, 1H), 6.72 (d, J=9 Hz, 1H), 4.58-4.49 (m, 1H), 4.15-4.06 (m, 2H), 3.15-2.96 (m, 3H), 2.82-2.71 (m, 4H), 2.01-1.91 (m, 2H), 1.20-1.09 (m, 9H)

2AE

Methyl (2R)-2-{[(1,2,3,5,6,7-hexahydro-s-indacen-4-yl)carbamoyl]amino}-3-(pyrimidin-5-yl)propanoate

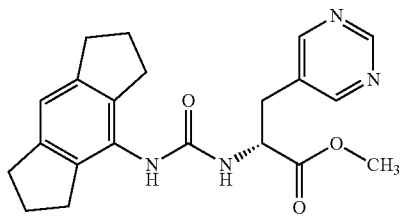 [SMILES: COC(=O)[C@@H](Cc1cncnc1)NC(=O)Nc1c2c(cc3c1CCC3)CCC2]

SM: methyl (2R)-2-amino-3-(pyrimidin-5-yl)propanoate hydrochloride

General Procedure A

The crude product was purified by acidic preparative HPLC to give the desired product as a white solid.
Y=85%
MS ES$^+$: 381.5
$^1$H NMR (400 MHz, DMSO-d6) δ 9.07 (s, 1H), 8.66 (s, 2H), 7.84 (s, 1H), 6.87 (s, 1H), 6.53 (d, J=8 Hz, 1H), 4.60-4.53 (m, 1H), 3.68 (s, 3H), 3.15 (dd, J=14, 5 Hz, 1H), 3.01-2.95 (m, 1H), 2.80-2.76 (m, 4H), 2.61-2.57 (m, 4H), 1.98-1.90 (m, 4H).

2AF

Methyl (2R)-2-{[(1,2,3,5,6,7-hexahydro-s-indacen-4-yl)carbamoyl]amino}-3-(pyrazin-2-yl)propanoate

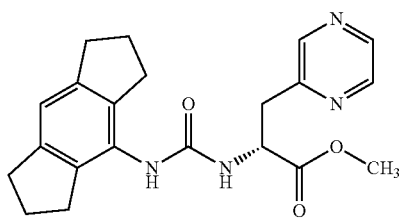 [SMILES: COC(=O)[C@@H](Cc1cnccn1)NC(=O)Nc1c2c(cc3c1CCC3)CCC2]

SM: methyl (2R)-2-amino-3-(pyrazin-2-yl)propanoate hydrochloride

General Procedure A

The crude product was purified by acidic preparative HPLC to give the desired product as a white solid.
Y=3%
MS ES$^+$: 381.5
$^1$H NMR (400 MHz, DMSO-d6) δ 8.60-8.55 (m, 2H), 8.52 (d, J=3 Hz, 1H), 7.88 (s, 1H), 6.87 (s, 1H), 6.51 (d, J=8 Hz, 1H), 4.73-4.65 (m, 1H), 3.64 (s, 3H), 3.30-3.16 (m, 2H), 2.80-2.76 (m, 4H), 2.61-2.57 (m, 4H), 1.96-1.90 (m, 4H).

2AG

Ethyl 2-{[(1,2,3,5,6,7-hexahydro-s-indacen-4-yl)carbamoyl]amino}-3-(pyridazin-4-yl)propanoate

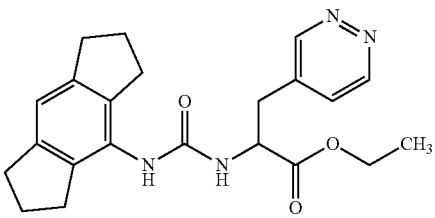 [SMILES: CCOC(=O)C(Cc1ccnnc1)NC(=O)Nc1c2c(cc3c1CCC3)CCC2]

SM: ethyl 2-amino-3-(pyridazin-4-yl)propanoate hydrochloride

General Procedure A

The crude product was purified by acidic preparative HPLC to give the desired product as a white solid.
Y=21%
MS ES$^+$: 395.4
$^1$H NMR (400 MHz, DMSO-d6) δ 9.14 (d, J=5 Hz, 1H), 9.11 (s, 1H), 7.83 (s, 1H), 7.56-7.54 (m, 1H), 6.88 (s, 1H), 6.51 (d, J=8 Hz, 1H), 4.61-4.53 (m, 1H), 4.12 (q, J=7 Hz, 2H), 3.15 (dd, J=14, 5 Hz, 1H), 3.06-3.0 (m, 1H), 2.80-2.76 (m, 4H), 2.62-2.58 (m, 4H), 1.98-1.90 (m, 4H), 1.19 (t, J=7 Hz, 3H).

2AH

Ethyl (2R)-2-{[(1,2,3,5,6,7-hexahydro-s-indacen-4-yl)carbamoyl]amino}-3-(pyrimidin-2-yl)propanoate

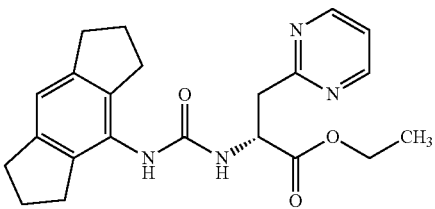 [SMILES: CCOC(=O)[C@@H](Cc1ncccn1)NC(=O)Nc1c2c(cc3c1CCC3)CCC2]

SM: ethyl 2-amino-3-(pyrimidin-2-yl)propanoate dihydrochloride

The racemic compound was synthesised according to the procedure detailed for Example 2VV. The racemate was separated by chiral HPLC to give the desired product as a white solid.
Y=14%
MS ES$^+$: 395

¹H NMR (400 MHz, DMSO-d6) δ 8.74 (d, J=5 Hz, 2H), 7.92 (s, 1H), 7.40 (t, J=5 Hz, 1H), 6.87 (s, 1H), 6.49 (d, J=9 Hz, 1H), 4.85-4.69 (m, 1H), 4.05 (q, J=7 Hz, 2H), 3.32-3.29 (m, 2H), 2.78 (t, J=7 Hz, 4H), 2.71-2.56 (m, 4H), 2.04-1.83 (m, 4H), 1.10 (t, J=7 Hz, 3H).

2AI ethyl 2-{[(1,2,3,5,6,7-hexahydro-s-indacen-4-yl)carbamoyl]amino}-3-(pyrimidin-4-yl)propanoate

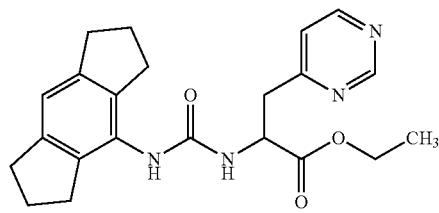 [SMILES: CCOC(=O)C(Cc1ccncn1)NC(=O)Nc1c2c(cc3c1CCC3)CCC2]

SM: ethyl 2-amino-3-(pyrimidin-4-yl)propanoate hydrochloride

General Procedure A

The crude product was purified by acidic preparative HPLC to give the desired product as a white solid.
Y=10%
MS ES⁺: 395.4
¹H NMR (400 MHz, DMSO-d6) δ 9.09 (d, J=1 Hz, 1H), 8.72 (d, J=5 Hz, 1H), 7.92 (s, 1H), 7.49-7.42 (m, 1H), 6.87 (s, 1H), 6.53 (d, J=8 Hz, 1H), 4.73-4.66 (m, 1H), 4.09 (q, J=7 Hz, 2H), 3.23-3.16 (m, 1H), 3.06-3.0 (m, 1H), 2.81-2.76 (m, 4H), 2.64-2.58 (m, 4H), 1.98-1.88 (m, 4H), 1.15 (t, J=7 Hz, 3H).

2AJ

2-{[(1,2,3,5,6,7-hexahydro-s-indacen-4-yl)carbamoyl]amino}-3-(pyrimidin-2-yl)propanoic acid

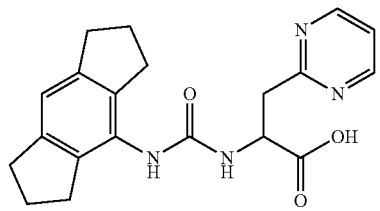

SM: 2-amino-3-(pyrimidin-2-yl)propanoic acid dihydrochloride

General Procedure A

Y=26%
MS ES⁺: 367.1
¹H NMR (300 MHz, DMSO-d6) δ 12.58 (br. s, 1H), 8.73 (d, J=5 Hz, 2H), 7.89 (s, 1H), 7.38 (t, J=5 Hz, 1H), 6.86 (s, 1H), 6.39 (d, J=9 Hz, 1H), 4.77-4.68 (m, 1H), 2.80-2.75 (m, 4H), 2.64-2.58 (m, 4H), 1.98-1.88 (m, 4H). 2 protons obscured by water or DMSO peak.

SUMMARY—TABLE OF DISCLOSED STRUCTURES

| Example no. | Structure | Name |
|---|---|---|
| 2A | 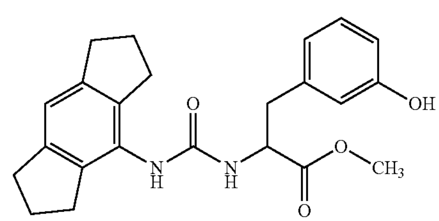 [SMILES: COC(=O)C(Cc1cccc(O)c1)NC(=O)Nc1c2c(cc3c1CCC3)CCC2] | methyl 2-{[(1,2,3,5,6,7-hexahydro-s-indacen-4-yl)carbamoyl]amino}-3-(3-hydroxyphenyl)propanoate |
| 2B | 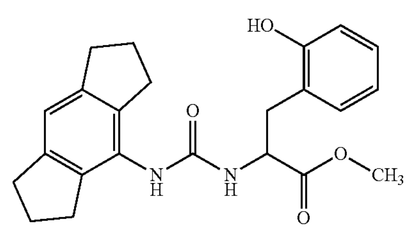 [SMILES: COC(=O)C(Cc1ccccc1O)NC(=O)Nc1c2c(cc3c1CCC3)CCC2] | Methyl2-{[(1,2,3,5,6,7-hexahydro-s-indacen-4-yl)carbamoyl]amino}-3-(2-hydroxyphenyl)propanoate |
| 2C | 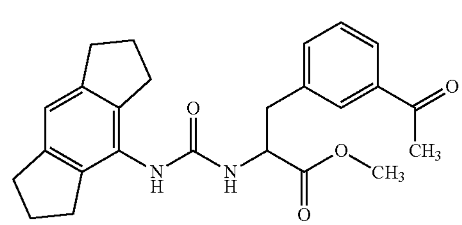 [SMILES: COC(=O)C(Cc1cccc(C(C)=O)c1)NC(=O)Nc1c2c(cc3c1CCC3)CCC2] | methyl 3-(3-acetylphenyl)-2-{[(1,2,3,5,6,7-hexahydro-s-indacen-4-yl)carbamoyl]amino}propanoate |

| Example no. | Structure | Name |
|---|---|---|
| 2D | 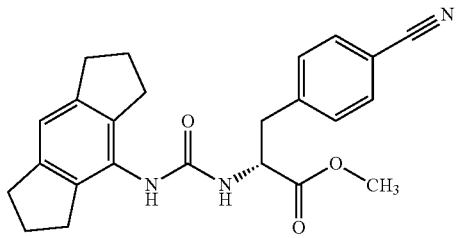 [SMILES: COC(=O)[C@@H](Cc1ccc(C#N)cc1)NC(=O)Nc1c2c(cc3c1CCC3)CCC2] | methyl (2R)-3-(4-cyanophenyl)-2-{[(1,2,3,5,6,7-hexahydro-s-indacen-4-yl)carbamoyl]amino}propanoate |
| 2E | 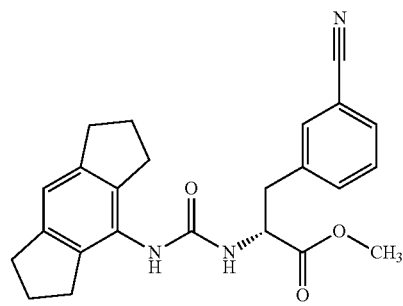 [SMILES: COC(=O)[C@@H](Cc1cccc(C#N)c1)NC(=O)Nc1c2c(cc3c1CCC3)CCC2] | methyl (2R)-3-(3-cyanophenyl)-2-{[(1,2,3,5,6,7-hexahydro-s-indacen-4-yl)carbamoyl]amino}propanoate |
| 2F | 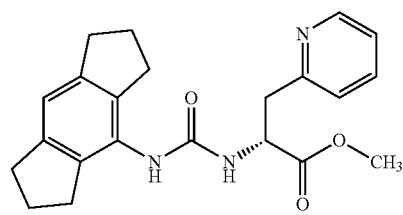 | methyl (2R)-2-{[(1,2,3,5,6,7-hexahydro-s-indacen-4-yl)carbamoyl]amino}-3-(pyridin-2-yl)propanoate |
| 2G | 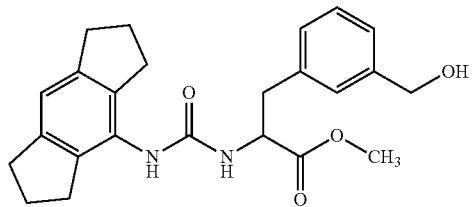 [SMILES: COC(=O)C(Cc1cccc(CO)c1)NC(=O)Nc1c2c(cc3c1CCC3)CCC2] | methyl 2-{[(1,2,3,5,6,7-hexahydro-s-indacen-4-yl)carbamoyl]amino}-3-[3-(hydroxymethyl)phenyl]propanoate |
| 2H | 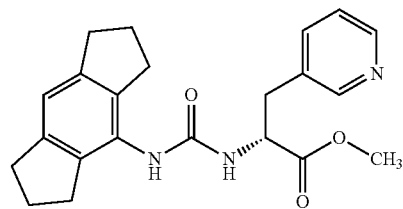 | methyl (2R)-2-{[(1,2,3,5,6,7-hexahydro-s-indacen-4-yl)carbamoyl]amino}-3-(pyridin-3-yl)propanoate |
| 2I | 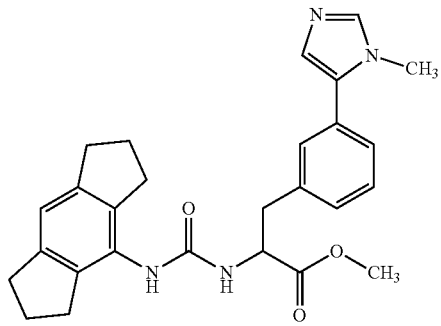 [SMILES: COC(=O)C(Cc1cccc(-c2cncn2C)c1)NC(=O)Nc1c2c(cc3c1CCC3)CCC2] | methyl 2-{[(1,2,3,5,6,7-hexahydro-s-indacen-4-yl)carbamoyl]amino}-3-[3-(1-methyl-1H-imidazol-5-yl)phenyl]propanoate |

-continued

| Example no. | Structure | Name |
|---|---|---|
| 2J | 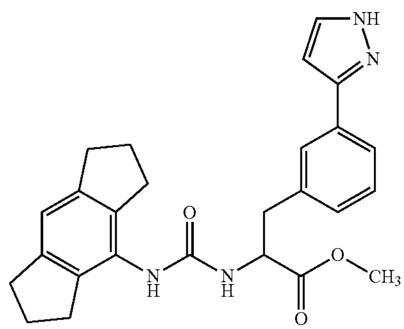 [SMILES: COC(=O)C(Cc1cccc(-c2cc[nH]n2)c1)NC(=O)Nc1c2c(cc3c1CCC3)CCC2] | Methyl 2-{[(1,2,3,5,6,7-hexahydro-s-indacen-4-yl)carbamoyl]amino}-3-[3-(1H-pyrazol-5-yl)phenyl]propanoate |
| 2K | 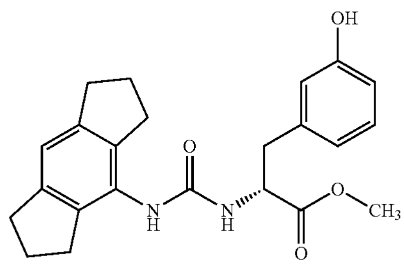 [SMILES: COC(=O)[C@@H](Cc1cccc(O)c1)NC(=O)Nc1c2c(cc3c1CCC3)CCC2] | methyl (2R)-2-{[(1,2,3,5,6,7-hexahydro-s-indacen-4-yl)carbamoyl]amino}-3-(3-hydroxyphenyl)propanoate |
| 2L | 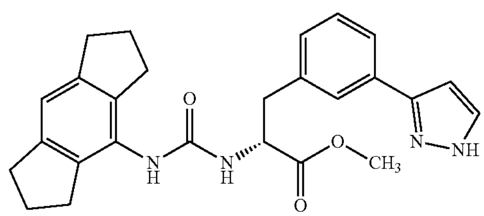 [SMILES: COC(=O)[C@@H](Cc1cccc(-c2cc[nH]n2)c1)NC(=O)Nc1c2c(cc3c1CCC3)CCC2] | methyl (2R)-2-{[(1,2,3,5,6,7-hexahydro-s-indacen-4-yl)carbamoyl]amino}-3-[3-(1H-pyrazol-3-yl)phenyl]propanoate |
| 2M | 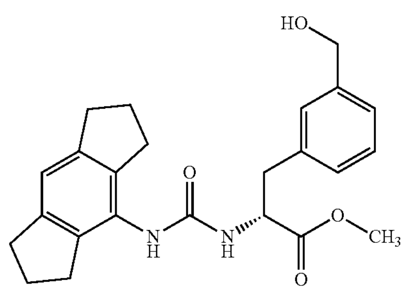 [SMILES: COC(=O)[C@@H](Cc1cccc(CO)c1)NC(=O)Nc1c2c(cc3c1CCC3)CCC2] | methyl (2R)-2-{[(1,2,3,5,6,7-hexahydro-s-indacen-4-yl)carbamoyl]amino}-3-[3-(hydroxymethyl)phenyl]propanoate |
| 2N | 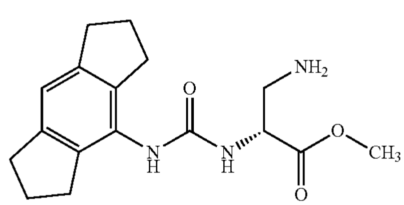 [SMILES: COC(=O)[C@@H](CN)NC(=O)Nc1c2c(cc3c1CCC3)CCC2] | methyl (2R)-3-amino-2-{[(1,2,3,5,6,7-hexahydro-s-indacen-4-yl)carbamoyl]amino}propanoate |
| 2O | 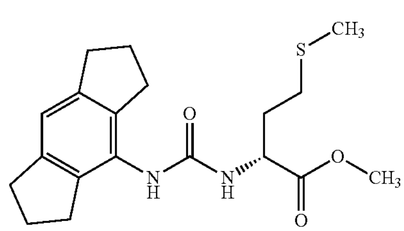 [SMILES: COC(=O)[C@@H](CCSC)NC(=O)Nc1c2c(cc3c1CCC3)CCC2] | methyl (2R)-2-{[(1,2,3,5,6,7-hexahydro-s-indacen-4-yl)carbamoyl]amino}-4-(methylsulfanyl)butanoate |

-continued

| Example no. | Structure | Name |
|---|---|---|
| 2P | 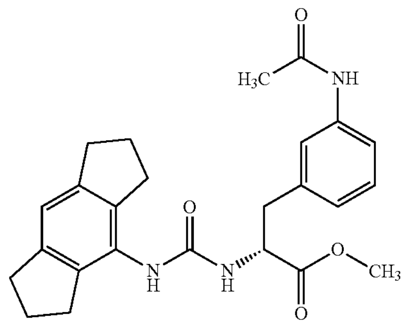 [SMILES: COC(=O)[C@@H](Cc1cccc(NC(C)=O)c1)NC(=O)Nc1c2c(cc3c1CCC3)CCC2] | methyl (2R)-3-(3-acetamidophenyl)-2-{[(1,2,3,5,6,7-hexahydro-s-indacen-4-yl)carbamoyl]amino}propanoate |
| 2Q | 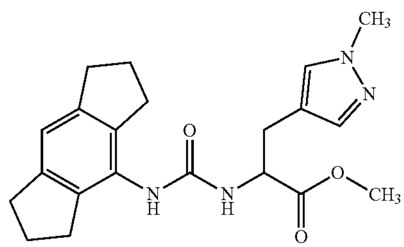 [SMILES: COC(=O)C(Cc1cnn(C)c1)NC(=O)Nc1c2c(cc3c1CCC3)CCC2] | methyl 2-{[(1,2,3,5,6,7-hexahydro-s-indacen-4-yl)carbamoyl]amino}-3-(1-methyl-1H-pyrazol-4-yl)propanoate |
| 2R | 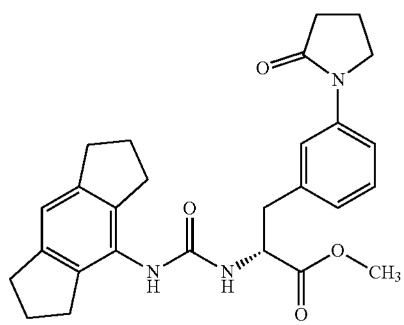 [SMILES: COC(=O)[C@@H](Cc1cccc(N2CCCC2=O)c1)NC(=O)Nc1c2c(cc3c1CCC3)CCC2] | methyl (2R)-2-{[(1,2,3,5,6,7-hexahydro-s-indacen-4-yl)carbamoyl]amino}-3-[3-(2-oxopyrrolidin-1-yl)phenyl]propanoate |
| 2S | 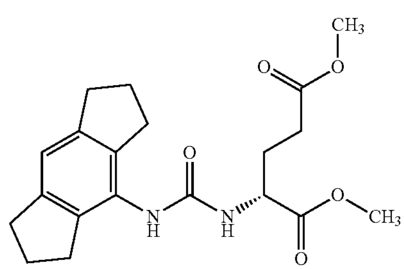 [SMILES: COC(=O)CC[C@@H](NC(=O)Nc1c2c(cc3c1CCC3)CCC2)C(=O)OC] | 1,5-dimethyl (2R)-2-{[(1,2,3,5,6,7-hexahydro-s-indacen-4-yl)carbamoyl]amino}pentanedioate |
| 2T | 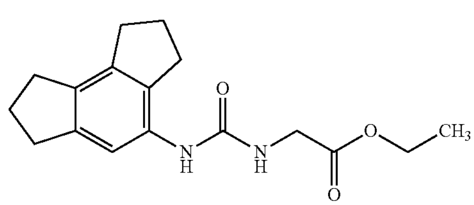 [SMILES: CCOC(=O)CNC(=O)Nc1cc2c(c3c1CCC3)CCC2] | ethyl 2-[({1H,2H,3H,6H,7H,8H,9H-cyclopenta[a]naphthalen-5-yl}carbamoyl)amino]acetate |

| Example no. | Structure | Name |
|---|---|---|
| 2U | 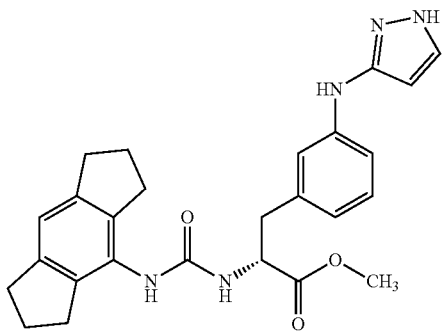 [SMILES: COC(=O)[C@@H](Cc1cccc(Nc2cc[nH]n2)c1)NC(=O)Nc1c2c(cc3c1CCC3)CCC2] | methyl (2R)-2-{[(1,2,3,5,6,7-hexahydro-s-indacen-4-yl)carbamoyl]amino}-3-{3-[(1H-pyrazol-3-yl)amino]phenyl}propanoate |
| 2V | 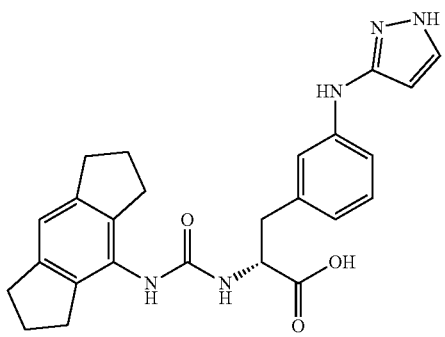 [SMILES: O=C(Nc1c2c(cc3c1CCC3)CCC2)N[C@H](Cc1cccc(Nc2cc[nH]n2)c1)C(=O)O] | (2R)-2-{[(1,2,3,5,6,7-hexahydro-s-indacen-4-yl)carbamoyl]amino}-3-[3-(1H-pyrazol-3-yl)phenyl]propanoic acid |
| 2W | 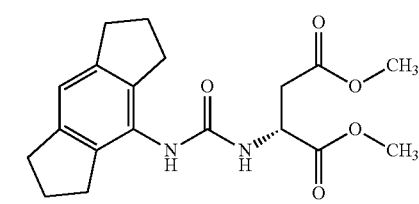 [SMILES: COC(=O)C[C@@H](NC(=O)Nc1c2c(cc3c1CCC3)CCC2)C(=O)OC] | 1,4-dimethyl (2R)-2-{[(1,2,3,5,6,7-hexahydro-s-indacen-4-yl)carbamoyl]amino}butanedioate |
| 2X | 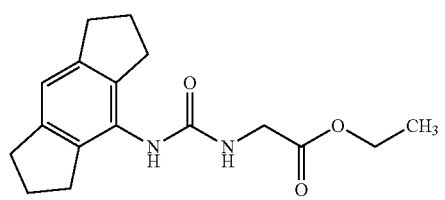 [SMILES: CCOC(=O)CNC(=O)Nc1c2c(cc3c1CCC3)CCC2] | ethyl 2-{[(1,2,3,5,6,7-hexahydro-s-indacen-4-yl)carbamoyl]amino}acetate |
| 2Y | 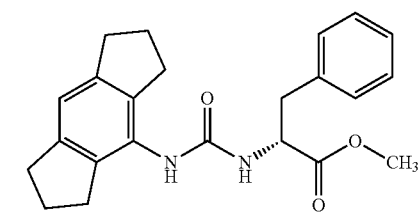 [SMILES: COC(=O)[C@@H](Cc1ccccc1)NC(=O)Nc1c2c(cc3c1CCC3)CCC2] | methyl (2R)-2-{[(1,2,3,5,6,7-hexahydro-s-indacen-4-yl)carbamoyl]amino}-3-phenylpropanoate |
| 2Z | 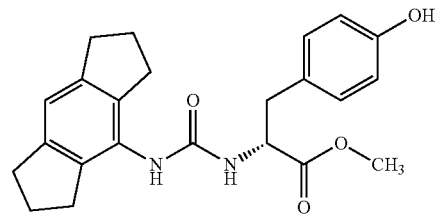 [SMILES: COC(=O)[C@@H](Cc1ccc(O)cc1)NC(=O)Nc1c2c(cc3c1CCC3)CCC2] | methyl (2R)-2-{[(1,2,3,5,6,7-hexahydro-s-indacen-4-yl)carbamoyl]amino}-3-(4-hydroxyphenyl)propanoate |

-continued

| Example no. | Structure | Name |
|---|---|---|
| 2AA | 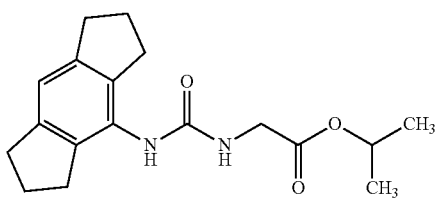 [SMILES: CC(C)OC(=O)CNC(=O)Nc1c2c(cc3c1CCC3)CCC2] | propan-2-yl 2-{[(1,2,3,5,6,7-hexahydro-s-indacen-4-yl)carbamoyl]amino}acetate |
| 2BB | 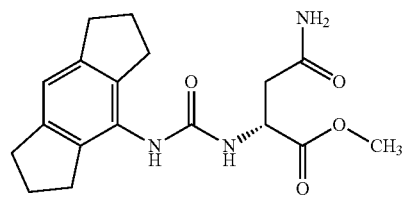 [SMILES: COC(=O)[C@@H](CC(N)=O)NC(=O)Nc1c2c(cc3c1CCC3)CCC2] | methyl (2R)-3-carbamoyl-2-{[(1,2,3,5,6,7-hexahydro-s-indacen-4-yl)carbamoyl]amino}propanoate |
| 2CC | 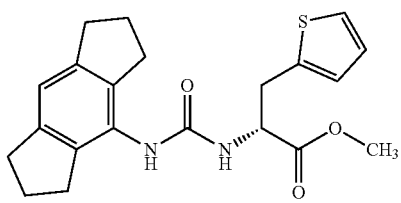 [SMILES: COC(=O)[C@@H](Cc1cccs1)NC(=O)Nc1c2c(cc3c1CCC3)CCC2] | methyl (2R)-2-{[(1,2,3,5,6,7-hexahydro-s-indacen-4-yl)carbamoyl]amino}-3-(thiophen-2-yl)propanoate |
| 2DD | 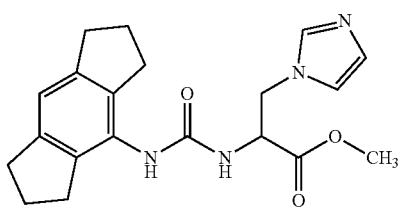 [SMILES: COC(=O)C(Cn1ccnc1)NC(=O)Nc1c2c(cc3c1CCC3)CCC2] | methyl 2-{[(1,2,3,5,6,7-hexahydro-s-indacen-4-yl)carbamoyl]amino}-3-(1H-imidazol-1-yl)propanoate |
| 2EE | 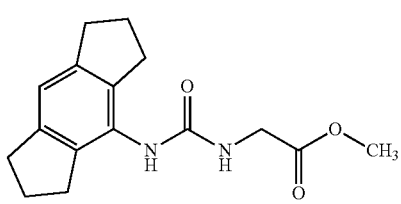 [SMILES: COC(=O)CNC(=O)Nc1c2c(cc3c1CCC3)CCC2] | methyl 2-{[(1,2,3,5,6,7-hexahydro-s-indacen-4-yl)carbamoyl]amino}acetate |
| 2FF | 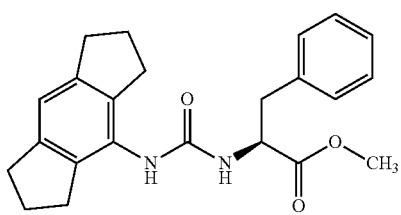 [SMILES: COC(=O)[C@H](Cc1ccccc1)NC(=O)Nc1c2c(cc3c1CCC3)CCC2] | (2S)-2-{[(1,2,3,5,6,7-hexahydro-s-indacen-4-yl)carbamoyl]amino}-3-phenylpropanoic acid |
| 2GG | 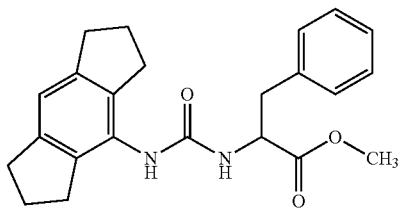 | methyl 2-{[(1,2,3,5,6,7-hexahydro-s-indacen-4-yl)carbamoyl]amino}-3-phenylpropanoate |

-continued

| Example no. | Structure | Name |
|---|---|---|
| 2HH | 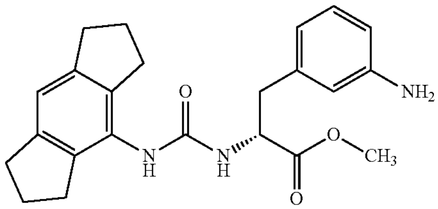 [SMILES: COC(=O)[C@@H](Cc1cccc(N)c1)NC(=O)Nc1c2c(cc3c1CCC3)CCC2] | methyl (2R)-3-(3-aminophenyl)-2-{[(1,2,3,5,6,7-hexahydro-s-indacen-4-yl)carbamoyl]amino}propanoate |
| 2II | 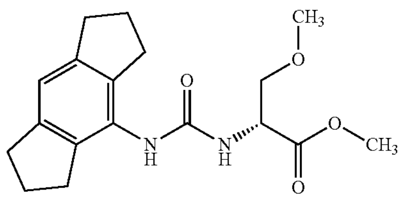 [SMILES: COC[C@@H](NC(=O)Nc1c2c(cc3c1CCC3)CCC2)C(=O)OC] | methyl (2R)-2-{[(1,2,3,5,6,7-hexahydro-s-indacen-4-yl)carbamoyl]amino}-3-methoxypropanoate |
| 2JJ | 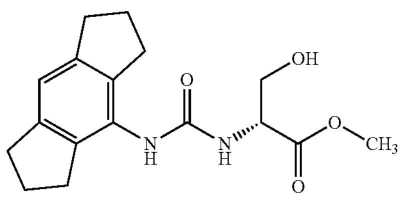 | methyl (2R)-2-{[(1,2,3,5,6,7-hexahydro-s-indacen-4-yl)carbamoyl]amino}-3-hydroxypropanoate |
| 2KK | 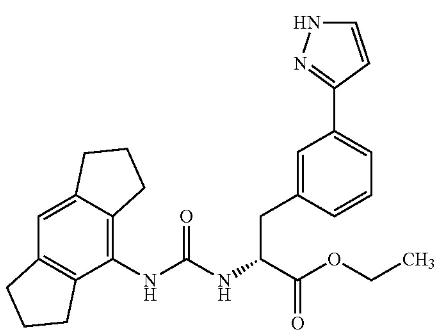 [SMILES: CCOC(=O)[C@@H](Cc1cccc(-c2cc[nH]n2)c1)NC(=O)Nc1c2c(cc3c1CCC3)CCC2] | ethyl (2R)-2-{[(1,2,3,5,6,7-hexahydro-s-indacen-4-yl)carbamoyl]amino}-3-[3-(1H-pyrazol-4-yl)phenyl]propanoate |
| 2LL | 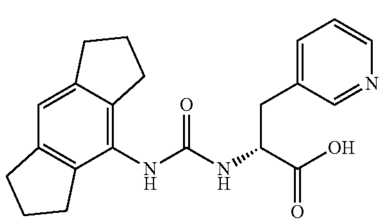 [SMILES: O=C(Nc1c2c(cc3c1CCC3)CCC2)N[C@H](Cc1cccnc1)C(=O)O] | (2R)-2-{[(1,2,3,5,6,7-hexahydro-s-indacen-4-yl)carbamoyl]amino}-3-(pyridin-3-yl)propanoic acid |
| 2MM | 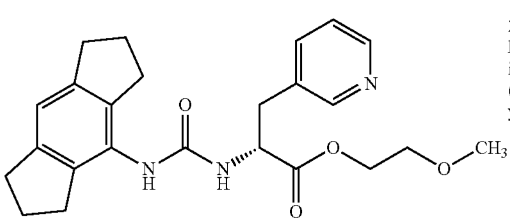 | 2-methoxyethyl (2R)-2-{[(1,2,3,5,6,7-hexahydro-s-indacen-4-yl)carbamoyl]amino}-3-(pyridin-3-yl)propanoate |

-continued

| Example no. | Structure | Name |
|---|---|---|
| 2NN | 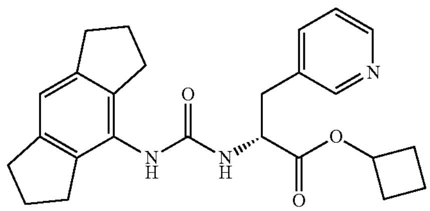 [SMILES: O=C(Nc1c2c(cc3c1CCC3)CCC2)N[C@H](Cc1cccnc1)C(=O)OC1CCC1] | cyclobutyl (2R)-2-{[(1,2,3,5,6,7-hexahydro-s-indacen-4-yl)carbamoyl]amino}-3-(pyridin-3-yl)propanoate |
| 2OO | 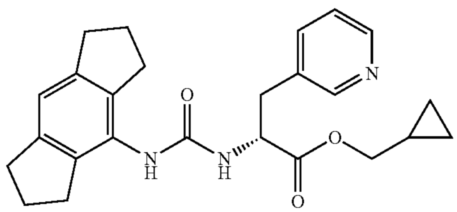 [SMILES: O=C(Nc1c2c(cc3c1CCC3)CCC2)N[C@H](Cc1cccnc1)C(=O)OCC1CC1] | cyclopropylmethyl (2R)-2-{[(1,2,3,5,6,7-hexahydro-s-indacen-4-yl)carbamoyl]amino}-3-(pyridin-3-yl)propanoate |
| 2PP | 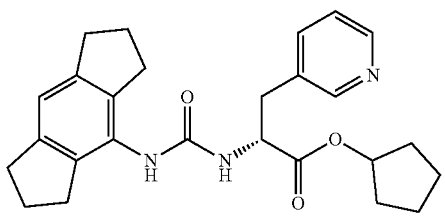 [SMILES: O=C(Nc1c2c(cc3c1CCC3)CCC2)N[C@H](Cc1cccnc1)C(=O)OC1CCCC1] | cyclopentyl (2R)-2-{[(1,2,3,5,6,7-hexahydro-s-indacen-4-yl)carbamoyl]amino}-3-(pyridin-3-yl)propanoate |
| 2QQ | 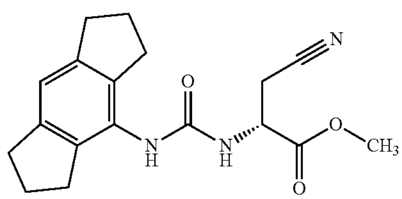 [SMILES: COC(=O)[C@@H](CC#N)NC(=O)Nc1c2c(cc3c1CCC3)CCC2] | methyl (2R)-3-cyano-2-{[(1,2,3,5,6,7-hexahydro-s-indacen-4-yl)carbamoyl]amino}propanoate |
| 2RR | 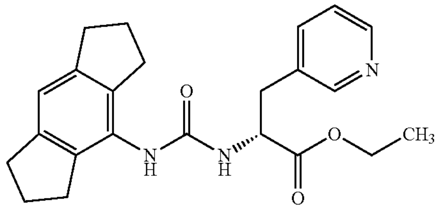 [SMILES: CCOC(=O)[C@@H](Cc1cccnc1)NC(=O)Nc1c2c(cc3c1CCC3)CCC2] | ethyl (2R)-2-{[(1,2,3,5,6,7-hexahydro-s-indacen-4-yl)carbamoyl]amino}-3-(pyridin-3-yl)propanoate |
| 2SS | 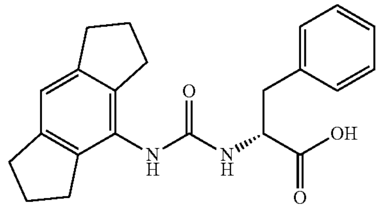 [SMILES: O=C(Nc1c2c(cc3c1CCC3)CCC2)N[C@H](Cc1ccccc1)C(=O)O] | (2R)-2-{[(1,2,3,5,6,7-hexahydro-s-indacen-4-yl)carbamoyl]amino}-3-phenylpropanoic acid |
| 2TT | 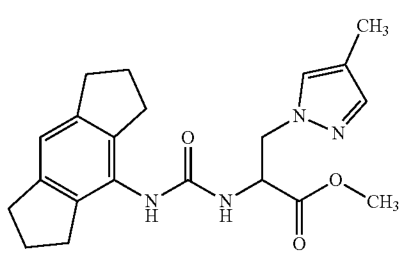 [SMILES: COC(=O)C(Cn1cc(C)cn1)NC(=O)Nc1c2c(cc3c1CCC3)CCC2] | methyl 2-{[(1,2,3,5,6,7-hexahydro-s-indacen-4-yl)carbamoyl]amino}-3-(4-methyl-1H-pyrazol-1-yl)propanoate |

| Example no. | Structure | Name |
|---|---|---|
| 2UU | 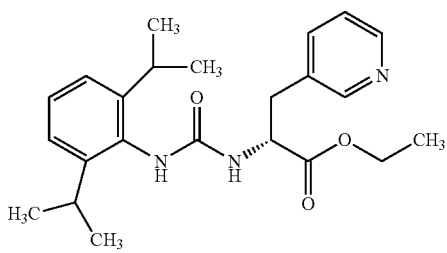 [SMILES: CCOC(=O)[C@@H](Cc1cccnc1)NC(=O)Nc1c(C(C)C)cccc1C(C)C] | ethyl (2R)-2-({[2,6-bis(propan-2-yl)phenyl]carbamoyl}amino)-3-(pyridin-3-yl)propanoate |
| 2VV | 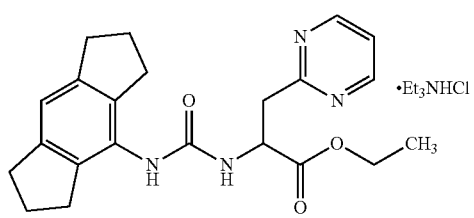 ·Et₃NHCl | ethyl 2-{[(1,2,3,5,6,7-hexahydro-s-indacen-4-yl)carbamoyl]amino}-3-(pyrimidin-2-yl)propanoate |
| 2WW | 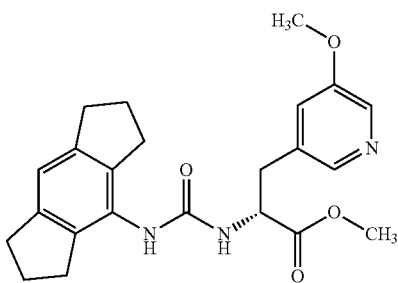 [SMILES: COC(=O)[C@@H](Cc1cncc(OC)c1)NC(=O)Nc1c2c(cc3c1CCC3)CCC2] | methyl (2R)-2-{[(1,2,3,5,6,7-hexahydro-s-indacen-4-yl)carbamoyl]amino}-3-(5-methoxypyridin-3-yl)propanoate |
| 2XX | 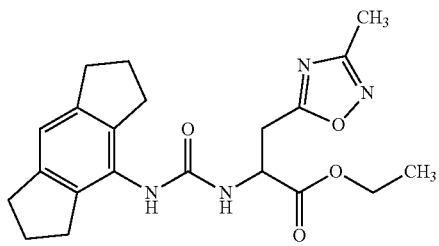 [SMILES: CCOC(=O)C(Cc1nc(C)no1)NC(=O)Nc1c2c(cc3c1CCC3)CCC2] | ethyl 2-{[(1,2,3,5,6,7-hexahydro-s-indacen-4-yl)carbamoyl]amino}-3-(3-methyl-1,2,4-oxadiazol-5-yl)propanoate |
| 2YY | 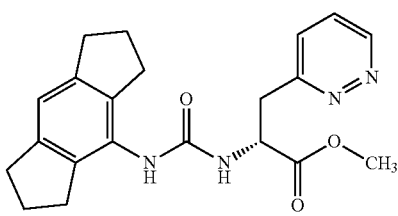 [SMILES: COC(=O)[C@@H](Cc1cccnn1)NC(=O)Nc1c2c(cc3c1CCC3)CCC2] | methyl (2R)-2-{[(1,2,3,5,6,7-hexahydro-s-indacen-4-yl)carbamoyl]amino}-3-(pyridazin-3-yl)propanoate |
| 2ZZ | 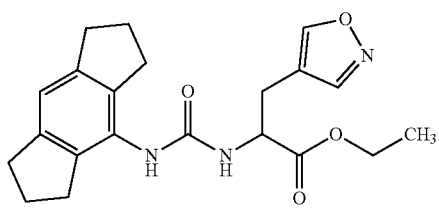 | ethyl 2-{[(1,2,3,5,6,7-hexahydro-s-indacen-4-yl)carbamoyl]amino}-3-(1,2-oxazol-4-yl)propanoate |

| Example no. | Structure | Name |
|---|---|---|
| 2AB | 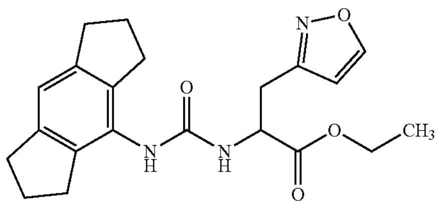 | Ethyl 2-{[(1,2,3,5,6,7-hexahydro-s-indacen-4-yl)carbamoyl]amino}-3-(1,2-oxazol-3-yl)propanoate |
| 2AC | 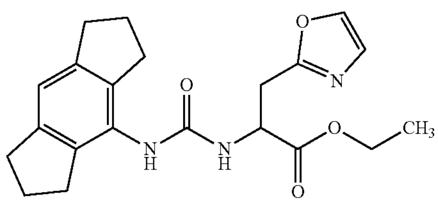 [SMILES: CCOC(=O)C(Cc1ncco1)NC(=O)Nc1c2c(cc3c1CCC3)CCC2] | ethyl 2-{[(1,2,3,5,6,7-hexahydro-s-indacen-4-yl)carbamoyl]amino}-3-(1,3-oxazol-2-yl)propanoate |
| 2AD | 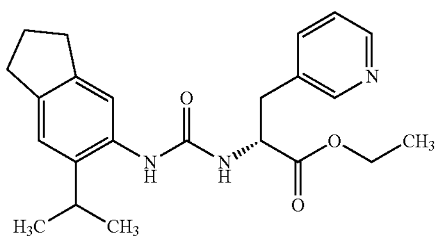 [SMILES: CCOC(=O)[C@@H](Cc1cccnc1)NC(=O)Nc1cc2c(cc1C(C)C)CCC2] | ethyl (2R)-2-(1[6-(propan-2-yl)-2,3-dihydro-1H-inden-5-yl]carbamoyl}amino)-3-(pyridin-3-yl)propanoate |
| 2AE | 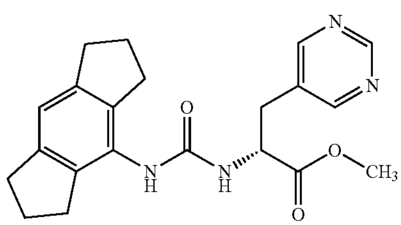 [SMILES: COC(=O)[C@@H](Cc1cncnc1)NC(=O)Nc1c2c(cc3c1CCC3)CCC2] | methyl (2R)-2-{[(1,2,3,5,6,7-hexahydro-s-indacen-4-yl)carbamoyl]amino}-3-(pyrimidin-5-yl)propanoate |
| 2AF | 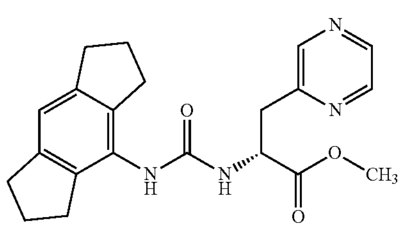 [SMILES: COC(=O)[C@@H](Cc1cnccn1)NC(=O)Nc1c2c(cc3c1CCC3)CCC2] | methyl (2R)-2-{[(1,2,3,5,6,7-hexahydro-s-indacen-4-yl)carbamoyl]amino}-3-(pyrazin-2-yl)propanoate |
| 2AG | 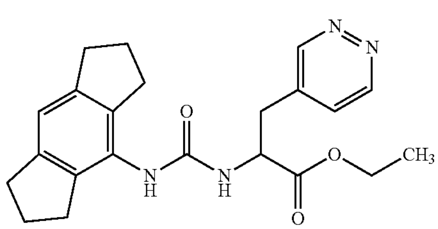 [SMILES: CCOC(=O)C(Cc1ccnnc1)NC(=O)Nc1c2c(cc3c1CCC3)CCC2] | ethyl 2-{[(1,2,3,5,6,7-hexahydro-s-indacen-4-yl)carbamoyl]amino}-3-(pyridazin-4-yl)propanoate |
| 2AH | 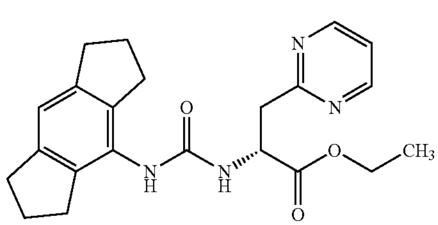 [SMILES: CCOC(=O)[C@@H](Cc1ncccn1)NC(=O)Nc1c2c(cc3c1CCC3)CCC2] | ethyl (2R)-2-{[(1,2,3,5,6,7-hexahydro-s-indacen-4-yl)carbamoyl]amino}-3-(pyrimidin-2-yl)propanoate |

-continued

| Example no. | Structure | Name |
|---|---|---|
| 2AI | 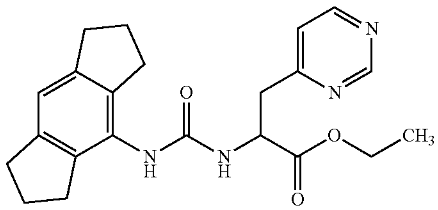 [SMILES: CCOC(=O)C(Cc1ccncn1)NC(=O)Nc1c2c(cc3c1CCC3)CCC2] | ethyl 2-{[(1,2,3,5,6,7-hexahydro-s-indacen-4-yl)carbamoyl]amino}-3-(pyrimidin-4-yl)propanoate |
| 2AJ | 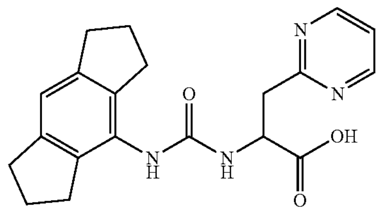 | 2-{[(1,2,3,5,6,7-hexahydro-s-indacen-4-yl)carbamoyl]amino}-3-(pyrimidin-2-yl)propanoic acid |

Activity

Determination of the Inhibitory Activity In Vitro

The biological activity of the compounds of the present disclosure was determined utilising the assay described hereinafter.

PBMC IC50 Determination Assay

The compounds of the present disclosure were tested for their inhibitory activity against IL1-β release upon NLRP3 activation in peripheral blood mononuclear cells (PBMC).

PBMC were isolated from buffy coats by density gradient centrifugation on Histopaque-1077 (Sigma, cat no. 10771). Isolated cells were seeded into the wells of a 96-well plate and incubated for 3 h with lipopolysaccharide (LPS). Following medium exchange, the compounds of the present disclosure were added (a single compound per well) and the cells were incubated for 30 min. Next, the cells were stimulated either with ATP (5 mM) or nigericin (10 μM) for 1 h and the cell culture media from the wells were collected for further analysis.

The release of IL-1β into the media was determined by a quantitative detection of IL-1β in 5 the media using an IL-1β enzyme-linked immunosorbent assay (ELISA) Ready-SET-Go!, eBioscience cat. No. 88-7261-88. Briefly, in a first step, high affinity binding plates (Corning, Costar 9018 or NUNC Maxisorp Cat No. 44-2404) were coated overnight at 4° C. with specific capture antibody included in the kit (anti-human IL-1β ref. 14-7018-68). Subsequently, plates were blocked with blocking buffer for 1 h at room temperature (rt) and after washing with a buffer (PBS with 0.05% Tween-20) incubated with protein standard and culture media. After 2 h of incubation at rt, plates were washed and incubated with biotinylated detection antibody included in the kit (anti-human IL-1β Biotin ref. 33-7110-68) for 1 h at rt. Plates were washed and incubated with HRP-streptavidin for 30 min at rt and washed again. The signal was developed after addition of 3,39,S,59-tetramethylbenzidine-peroxidase (TMB) until color appeared and the reaction was stopped by 2 M $H_2SO_4$. A microplate spectrophotometer (BioTek) was used to detect signals with 450 nm. The detection range of IL-1β ELISA was 2-150 ng/ml.

The determination of the $IC_{50}$ values was preformed using the Graph Pad Prism software and the measured $IC_{50}$ values of compounds of the present disclosure are shown in Table 1 below.

TABLE 1

| Example No. | PBMCs, $IC_{50}$, μM |
|---|---|
| 2A | 2.5 |
| 2B | 0.06 |
| 2C | 0.35 |
| 2D | 1.4 |
| 2E | 1.7 |
| 2F | 4.2 |
| 2G | 1.4 |
| 2H | 0.88 |
| 2I | 0.96 |
| 2J | 0.41 |
| 2K | 1.3 |
| 2L | 0.14 |
| 2M | 0.38 |
| 2N | 9.3 |
| 2O | 3.2 |
| 2P | 0.14 |
| 2Q | 2.4 |
| 2R | 0.33 |
| 2S | 3.5 |
| 2T | 3.1 |
| 2U | 0.31 |
| 2V | 0.52 |
| 2W | 2.9 |
| 2X | 1.5 |
| 2Y | 1.4 |
| 2Z | 0.10 |
| 2AA | 1.8 |
| 2BB | 32 |
| 2CC | 0.5 |
| 2DD | 6.2 |
| 2EE | 3.7 |
| 2FF | 9.1 |
| 2GG | 6.4 |
| 2HH | 4.4 |
| 2II | 5.3 |
| 2JJ | 26 |
| 2KK | 0.33 |
| 2LL | 2 |
| 2MM | 2.9 |
| 2NN | 0.6 |
| 2OO | 0.47 |
| 2PP | 0.24 |
| 2QQ | <10 |
| 2RR | 1.7 |
| 2SS | 14 |
| 2TT | 14 |
| 2UU | 21 |
| 2VV | 0.12 |
| 2WW | 0.45 |

TABLE 1-continued

| Example No. | PBMCs, IC$_{50}$, μM |
|---|---|
| 2XX | 5.1 |
| 2YY | 3.3 |
| 2ZZ | 3.3 |
| 2AB | 1.8 |
| 2AC | 0.67 |
| 2AD | 2.9 |
| 2AE | 4.5 |
| 2AF | 0.46 |
| 2AG | 6.0 |
| 2AH | 0.036 |
| 2AI | 6.8 |
| 2AJ | 15 |

These results show that the compounds of the present disclosure are capable of inhibiting IL-1β release upon inflammasome activation.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I) or a pharmaceutically acceptable salt thereof:

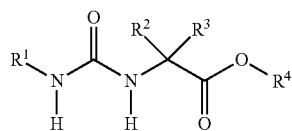
(I)

wherein:

R$_1$ is a hexahydroindacene ring:

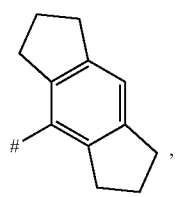

wherein # denotes the bond to the nitrogen atom of Formula (I), optionally substituted by 1, 2, 3 or 4 substituents independently selected from (1-6C)alkyl, (2-6C)alkenyl, (2-6C)alkynyl, (3-8C)cycloalkyl, (1-3C)alkoxy, halo, oxo, hydroxy, cyano, amino, (1-3C)alkylamino, di-[(1-3C)alkyl]-amino, CF$_3$, OCF$_3$, S(O)$_2$CH$_3$, S(O)CH$_3$, S(O)$_2$NH$_2$, S(O)$_2$NHCH$_3$, S(O)$_2$N(CH$_3$)$_2$, NHS(O)$_2$CH$_3$, and N(CH$_3$)S(O)$_2$CH$_3$;

R$_2$ is H;

R$_3$ is (1-4C)alkyl R$_7$, wherein R$_7$ is selected from a 5 or 6 membered monocyclic aryl or non-aryl ring system comprising 1, 2, or 3 heteroatoms independently selected from oxygen, nitrogen and sulfur, or 3, 4, 5 or 6 membered monocyclic heterocyclyl ring system comprising 1 or 2 heteroatoms independently selected from oxygen, nitrogen and sulfur, wherein said heterocyclic R$_7$ ring system is optionally substituted with 1 or more substituents independently selected from (1-6C) alkyl, alkylhydroxy, nitro, OH, COCH$_3$, halo, amino, cyano, and R$_8$, or wherein R$_7$ is selected from a 5 or 6 membered monocyclic aryl or non-aryl ring system optionally comprising 1, 2 or 3 heteroatoms independently selected from oxygen, nitrogen and sulfur, 3, 4, 5 or 6 membered monocyclic heterocyclyl ring system optionally comprising 1 or 2 heteroatoms independently selected from oxygen, nitrogen and sulfur, and a 3, 4, 5 or 6 membered saturated or partially unsaturated carbocyclic ring system wherein the R$_7$ ring system is substituted with 1 or more substituents independently selected from (1-6C)alkyl, alkylhydroxy, nitro, OH, COCH$_3$, halo, amino, cyano, and R$_8$, wherein R$_8$ is, an optionally N-linked, 5 or 6 membered monocyclic heteroaryl ring comprising 1 or 2 heteroatoms independently selected from oxygen, nitrogen and sulfur, or a 3, 4, 5 or 6 membered monocyclic heterocyclyl ring system comprising 1 heteroatom independently selected from oxygen, nitrogen and sulfur, said ring being optionally substituted with an alkyl, oxo, halo or amino group; and R$_4$ is H, alkyl, monocyclic saturated carbocyclic ring system, or monocyclic aryl group.

2. The compound of claim 1, wherein R$_3$ is methyl-R$_7$ or ethyl-R$_7$.

3. The compound of claim 1, wherein R$_7$ is a monocyclic aryl, optionally substituted with at least one hydroxyl group.

4. The compound of claim 1, wherein R$_7$ is a monocyclic aryl with a cyano substitution.

5. The compound of claim 1, wherein R$_7$ is a 5 or 6 membered monocyclic aryl ring comprising 1, 2 or 3 heteroatoms independently selected from oxygen, nitrogen, and sulfur.

6. The compound of claim 1, wherein R$_4$ is (1-4C)alkyl or (C3-C6)cycloalkyl.

7. The compound of claim 1, wherein R$_1$ is an unsubstituted hexahydroindacene ring:

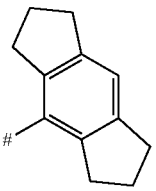

wherein # denotes the bond to the nitrogen atom of Formula (I).

8. A compound selected from the group consisting of:

| Structure | Name |
|---|---|
| 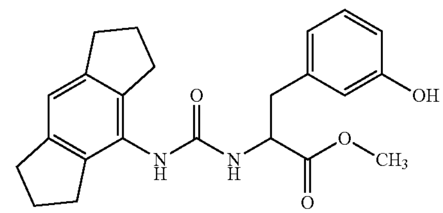 [SMILES: COC(=O)C(Cc1cccc(O)c1)NC(=O)Nc1c2c(cc3c1CCC3)CCC2] | (methyl 2-{[(1,2,3,5,6,7-hexahydro-s-indacen-4-yl)carbamoyl]amino}-3-(3-hydroxyphenyl)propanoate); |
| 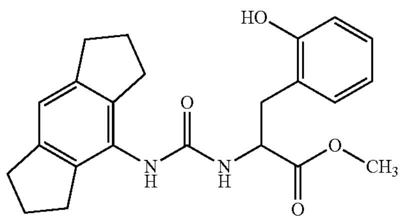 [SMILES: COC(=O)C(Cc1ccccc1O)NC(=O)Nc1c2c(cc3c1CCC3)CCC2] | (methyl2-{[(1,2,3,5,6,7-hexahydro-s-indacen-4-yl)carbamoyl]amino}-3-(2-hydroxyphenyl)propanoate); |
| 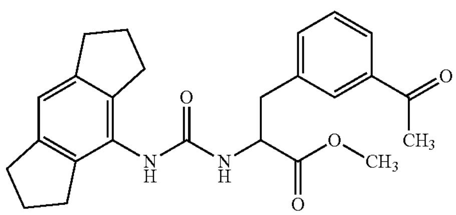 [SMILES: COC(=O)C(Cc1cccc(C(C)=O)c1)NC(=O)Nc1c2c(cc3c1CCC3)CCC2] | (methyl 3-(3-acetylphenyl)-2-{[(1,2,3,5,6,7-hexahydro-s-indacen-4-yl)carbamoyl]amino}propanoate); |
| 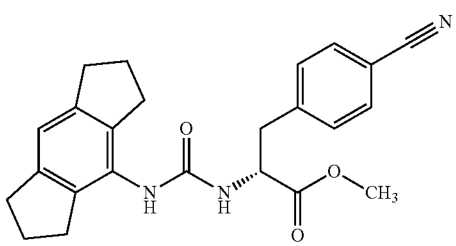 [SMILES: COC(=O)[C@@H](Cc1ccc(C#N)cc1)NC(=O)Nc1c2c(cc3c1CCC3)CCC2] | (methyl (2R)-3-(4-cyanophenyl)-2-{[(1,2,3,5,6,7-hexahydro-s-indacen-4-yl)carbamoyl]amino}propanoate); |
| 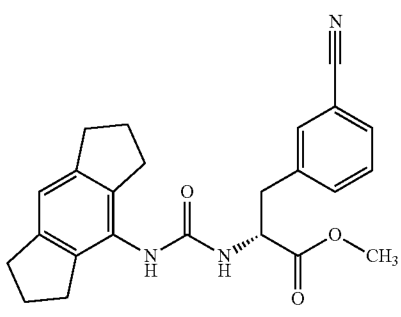 [SMILES: COC(=O)[C@@H](Cc1cccc(C#N)c1)NC(=O)Nc1c2c(cc3c1CCC3)CCC2] | (methyl (2R)-3-(3-cyanophenyl)-2-{[(1,2,3,5,6,7-hexahydro-s-indacen-4-yl)carbamoyl]amino}propanoate); |
| 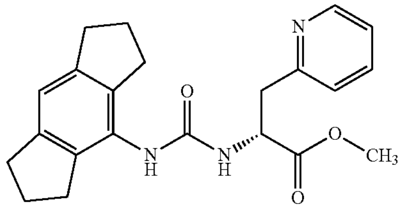 | (methyl (2R)-2-{[(1,2,3,5,6,7-hexahydro-s-indacen-4-yl)carbamoyl]amino}-3-(pyridin-2-yl)propanoate); |

| Structure | Name |
|---|---|
| 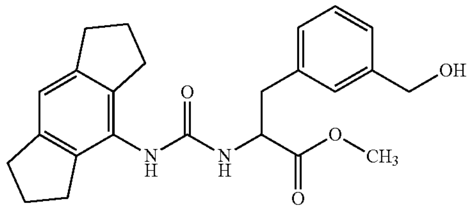 [SMILES: COC(=O)C(Cc1cccc(CO)c1)NC(=O)Nc1c2c(cc3c1CCC3)CCC2] | (methyl 2-{[(1,2,3,5,6,7-hexahydro-s-indacen-4-yl)carbamoyl]amino}-3-[3-(hydroxymethyl)phenyl]propanoate); |
| 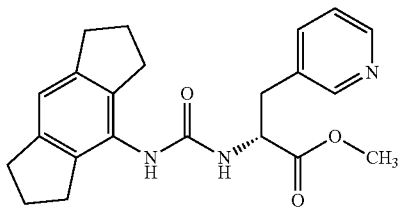 | (methyl (2R)-2-{[(1,2,3,5,6,7-hexahydro-s-indacen-4-yl)carbamoyl]amino}-3-(pyridin-3-yl)propanoate); |
| 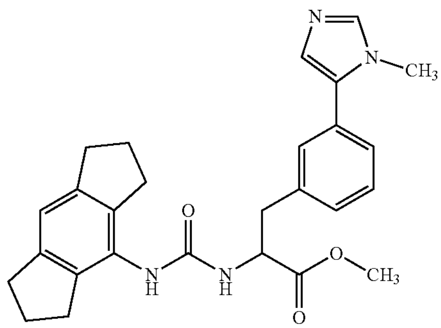 [SMILES: COC(=O)C(Cc1cccc(-c2cncn2C)c1)NC(=O)Nc1c2c(cc3c1CCC3)CCC2] | (methyl 2-{[(1,2,3,5,6,7-hexahydro-s-indacen-4-yl)carbamoyl]amino}-3-[3-(1-methyl-1H-imidazol-5-yl)phenyl]propanoate); |
| 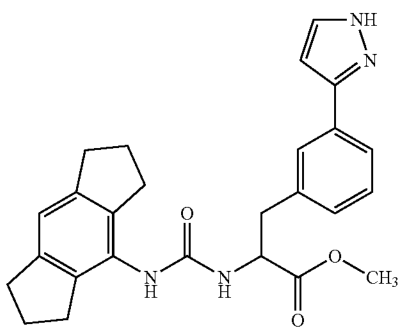 [SMILES: COC(=O)C(Cc1cccc(-c2cc[nH]n2)c1)NC(=O)Nc1c2c(cc3c1CCC3)CCC2] | (methyl 2-{[(1,2,3,5,6,7-hexahydro-s-indacen-4-yl)carbamoyl]amino}-3-[3-(1H-pyrazol-5-yl)phenyl]propanoate); |
| 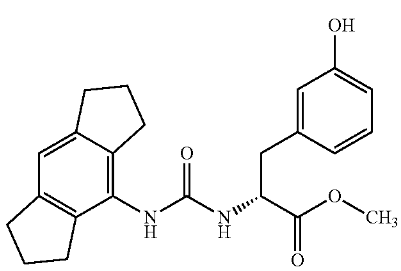 [SMILES: COC(=O)[C@@H](Cc1cccc(O)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-(3-hydroxyphenyl)propanoate); |
| 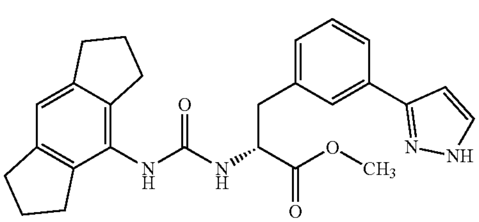 [SMILES: COC(=O)[C@@H](Cc1cccc(-c2cc[nH]n2)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-[3-(1H-pyrazol-3-yl)phenyl]propanoate); |

| Structure | Name |
|---|---|
| 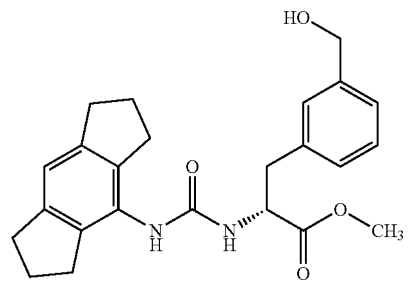 [SMILES: COC(=O)[C@@H](Cc1cccc(CO)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-[3-(hydroxymethyl)phenyl]propanoate); |
| 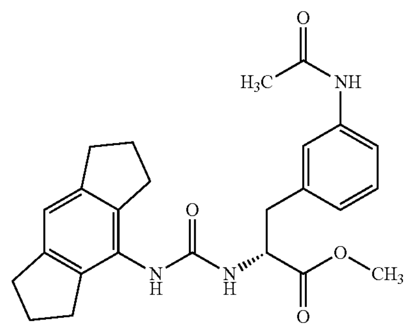 [SMILES: COC(=O)[C@@H](Cc1cccc(NC(C)=O)c1)NC(=O)Nc1c2c(cc3c1CCC3)CCC2] | (methyl (2R)-3-(3-acetamidophenyl)-2-{[(1,2,3,5,6,7-hexahydro-s-indacen-4-yl)carbamoyl]amino}propanoate); |
| 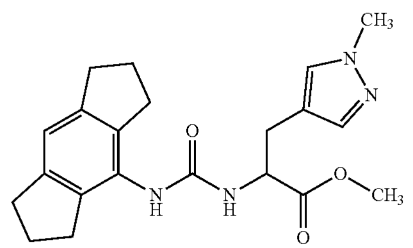 [SMILES: COC(=O)C(Cc1cnn(C)c1)NC(=O)Nc1c2c(cc3c1CCC3)CCC2] | (methyl 2-{[(1,2,3,5,6,7-hexahydro-s-indacen-4-yl)carbamoyl]amino}-3-(1-methyl-1H-pyrazol-4-yl)propanoate); |
| 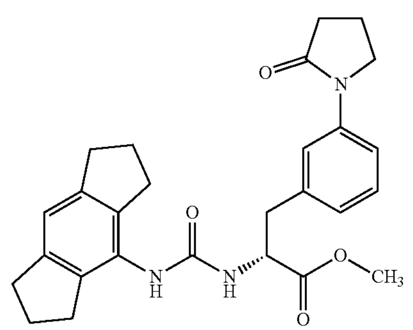 [SMILES: COC(=O)[C@@H](Cc1cccc(N2CCCC2=O)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-[3-(2-oxopyrrolidin-1-yl)phenyl]propanoate); |
| 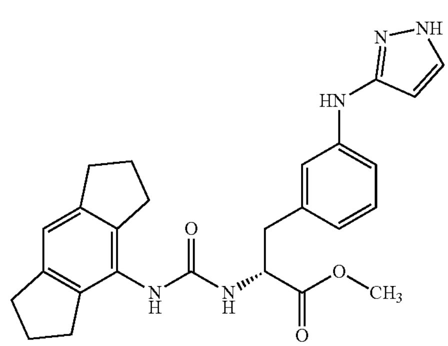 [SMILES: COC(=O)[C@@H](Cc1cccc(Nc2cc[nH]n2)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-{3-[(1H-pyrazol-3-yl)amino]phenyl}propanoate); |

| Structure | Name |
|---|---|
| 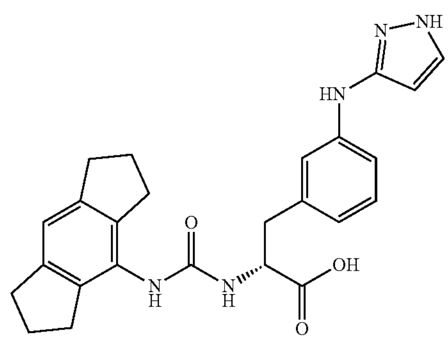 [SMILES: O=C(Nc1c2c(cc3c1CCC3)CCC2)N[C@H](Cc1cccc(Nc2cc[nH]n2)c1)C(=O)O] | ((2R)-2-{[(1,2,3,5,6,7-hexahydro-s-indacen-4-yl)carbamoyl]amino}-3-[3-(1H-pyrazol-3-yl)phenyl]propanoic acid); |
| 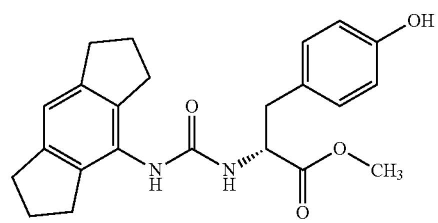 [SMILES: COC(=O)[C@@H](Cc1ccc(O)cc1)NC(=O)Nc1c2c(cc3c1CCC3)CCC2] | (methyl (2R)-2-{[(1,2,3,5,6,7-hexahydro-s-indacen-4-yl)carbamoyl]amino}-3-(4-hydroxyphenyl)propanoate); |
| 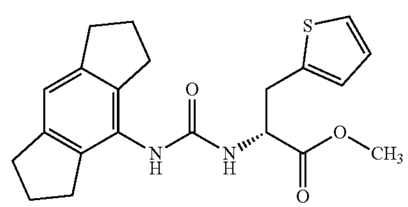 [SMILES: COC(=O)[C@@H](Cc1cccs1)NC(=O)Nc1c2c(cc3c1CCC3)CCC2] | (methyl (2R)-2-{[(1,2,3,5,6,7-hexahydro-s-indacen-4-yl)carbamoyl]amino}-3-(thiophen-2-yl)propanoate); |
| 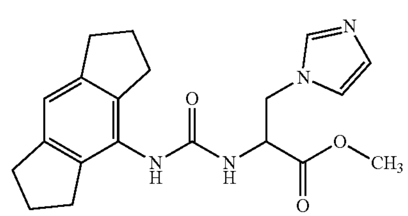 [SMILES: COC(=O)C(Cn1ccnc1)NC(=O)Nc1c2c(cc3c1CCC3)CCC2] | (methyl 2-{[(1,2,3,5,6,7-hexahydro-s-indacen-4-yl)carbamoyl]amino}-3-(1H-imidazol-1-yl)propanoate); |
| 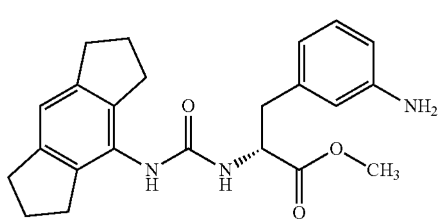 [SMILES: COC(=O)[C@@H](Cc1cccc(N)c1)NC(=O)Nc1c2c(cc3c1CCC3)CCC2] | (methyl (2R)-3-(3-aminophenyl)-2-{[(1,2,3,5,6,7-hexahydro-s-indacen-4-yl)carbamoyl]amino}propanoate); |
| 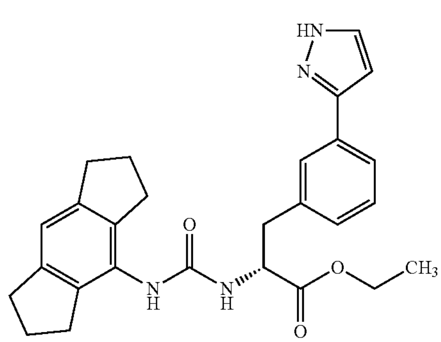 [SMILES: CCOC(=O)[C@@H](Cc1cccc(-c2cc[nH]n2)c1)NC(=O)Nc1c2c(cc3c1CCC3)CCC2] | (ethyl (2R)-2-{[(1,2,3,5,6,7-hexahydro-s-indacen-4-yl)carbamoyl]amino}-3-[3-(1H-pyrazol-4-yl)phenyl]propanoate); |

| Structure | Name |
|---|---|
| 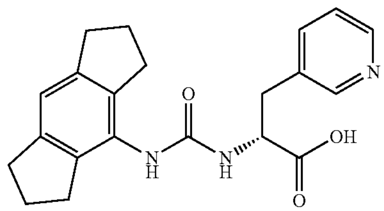 [SMILES: O=C(Nc1c2c(cc3c1CCC3)CCC2)N[C@H](Cc1cccnc1)C(=O)O] | ((2R)-2-{[(1,2,3,5,6,7-hexahydro-s-indacen-4-yl)carbamoyl]amino}-3-(pyridin-3-yl)propanoic acid); |
| 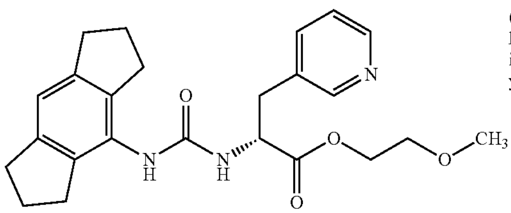 | (2-methoxyethyl (2R)-2-{[(1,2,3,5,6,7-hexahydro-s-indacen-4-yl)carbamoyl]amino}-3-(pyridin-3-yl)propanoate); |
| 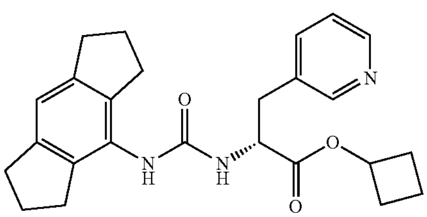 [SMILES: O=C(Nc1c2c(cc3c1CCC3)CCC2)N[C@H](Cc1cccnc1)C(=O)OC1CCC1] | (cyclobutyl (2R)-2-{[(1,2,3,5,6,7-hexahydro-s-indacen-4-yl)carbamoyl]amino}-3-(pyridin-3-yl)propanoate); |
| 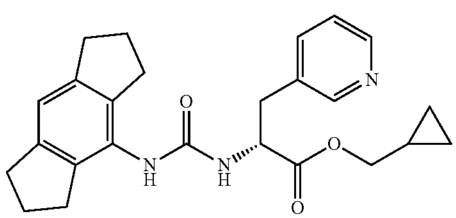 [SMILES: O=C(Nc1c2c(cc3c1CCC3)CCC2)N[C@H](Cc1cccnc1)C(=O)OCC1CC1] | (cyclopropylmethyl (2R)-2-{[(1,2,3,5,6,7-hexahydro-s-indacen-4-yl)carbamoyl]amino}-3-(pyridin-3-yl)propanoate); |
| 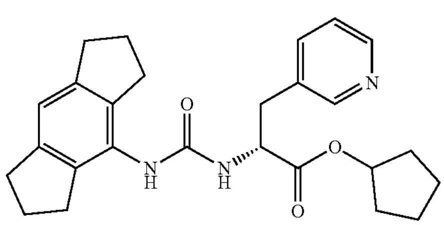 [SMILES: O=C(Nc1c2c(cc3c1CCC3)CCC2)N[C@H](Cc1cccnc1)C(=O)OC1CCCC1] | (cyclopentyl (2R)-2-{[(1,2,3,5,6,7-hexahydro-s-indacen-4-yl)carbamoyl]amino}-3-(pyridin-3-yl)propanoate); |
| 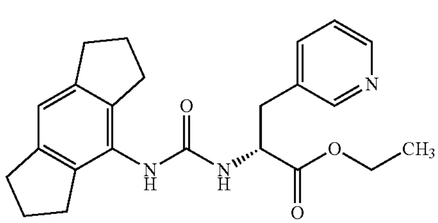 [SMILES: CCOC(=O)[C@@H](Cc1cccnc1)NC(=O)Nc1c2c(cc3c1CCC3)CCC2] | (ethyl (2R)-2-{[(1,2,3,5,6,7-hexahydro-s-indacen-4-yl)carbamoyl]amino}-3-(pyridin-3-yl)propanoate); |
| 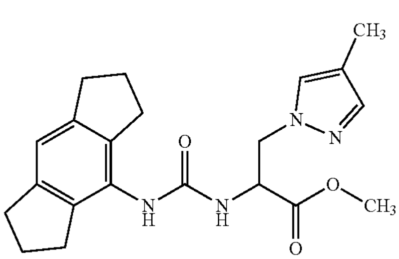 [SMILES: COC(=O)C(Cn1cc(C)cn1)NC(=O)Nc1c2c(cc3c1CCC3)CCC2] | (methyl 2-{[(1,2,3,5,6,7-hexahydro-s-indacen-4-yl)carbamoyl]amino}-3-(4-methyl-1H-pyrazol-1-yl)propanoate); |

-continued

| Structure | Name |
|---|---|
| 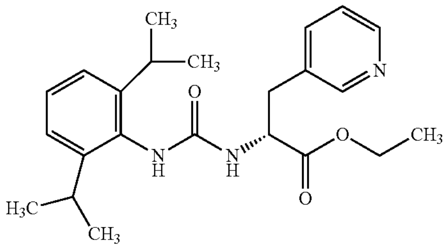 [SMILES: CCOC(=O)[C@@H](Cc1cccnc1)NC(=O)Nc1c(C(C)C)cccc1C(C)C] | (ethyl (2R)-2-({[2,6-bis(propan-2-yl)phenyl]carbamoyl}amino)-3-(pyridin-3-yl)propanoate); |
| | (ethyl 2-{[(1,2,3,5,6,7-hexahydro-s-indacen-4-yl)carbamoyl]amino}-3-(pyrimidin-2-yl)propanoate); •Et₃NHCl |
| 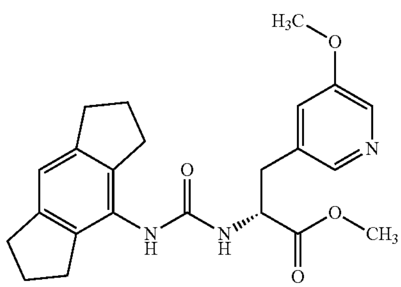 [SMILES: COC(=O)[C@@H](Cc1cncc(OC)c1)NC(=O)Nc1c2c(cc3c1CCC3)CCC2] | (methyl (2R)-2-{[(1,2,3,5,6,7-hexahydro-s-indacen-4-yl)carbamoyl]amino}-3-(5-methoxypyridin-3-yl)propanoate); |
| 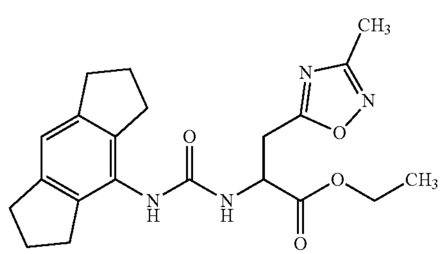 [SMILES: CCOC(=O)C(Cc1nc(C)no1)NC(=O)Nc1c2c(cc3c1CCC3)CCC2] | (ethyl 2-{[(1,2,3,5,6,7-hexahydro-s-indacen-4-yl)carbamoyl]amino}-3-(3-methyl-1,2,4-oxadiazol-5-yl)propanoate); |
| 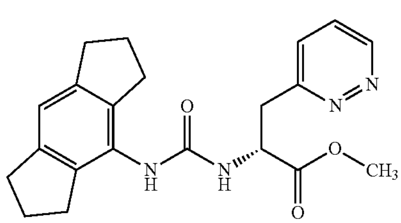 | (methyl (2R)-2-{[(1,2,3,5,6,7-hexahydro-s-indacen-4-yl)carbamoyl]amino}-3-(pyridazin-3-yl)propanoate); |
| 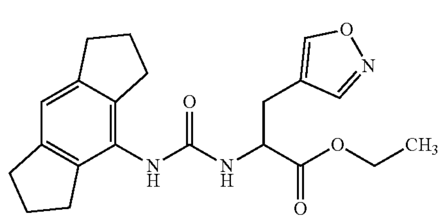 [SMILES: CCOC(=O)C(Cc1cnoc1)NC(=O)Nc1c2c(cc3c1CCC3)CCC2] | (ethyl 2-{[(1,2,3,5,6,7-hexahydro-s-indacen-4-yl)carbamoyl]amino}-3-(1,2-oxazol-4-yl)propanoate); |

| Structure | Name |
|---|---|
| 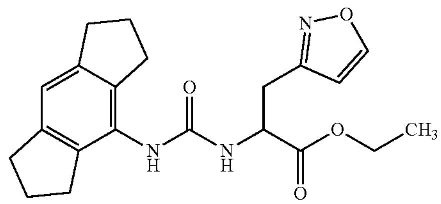 [SMILES: CCOC(=O)C(Cc1ccon1)NC(=O)Nc1c2c(cc3c1CCC3)CCC2] | (ethyl 2-{[(1,2,3,5,6,7-hexahydro-s-indacen-4-yl)carbamoyl]amino}-3-(1,2-oxazol-3-yl)propanoate); |
| 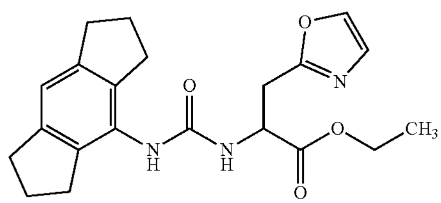 [SMILES: CCOC(=O)C(Cc1ncco1)NC(=O)Nc1c2c(cc3c1CCC3)CCC2] | (ethyl 2-{[(1,2,3,5,6,7-hexahydro-s-indacen-4-yl)carbamoyl]amino}-3-(1,3-oxazol-2-yl)propanoate); |
| 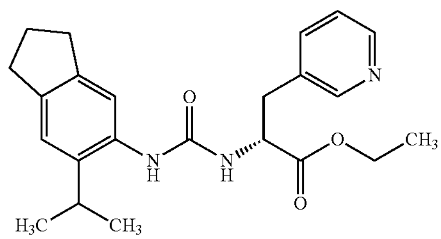 [SMILES: CCOC(=O)[C@@H](Cc1cccnc1)NC(=O)Nc1cc2c(cc1C(C)C)CCC2] | (ethyl (2R)-2-({[6-(propan-2-yl)-2,3-dihydro-1H-inden-5-yl]carbamoyl}amino)-3-(pyridin-3-yl)propanoate); |
| 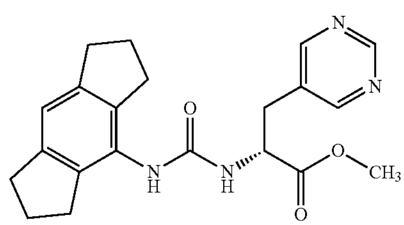 [SMILES: COC(=O)[C@@H](Cc1cncnc1)NC(=O)Nc1c2c(cc3c1CCC3)CCC2] | (methyl (2R)-2-{[(1,2,3,5,6,7-hexahydro-s-indacen-4-yl)carbamoyl]amino}-3-(pyrimidin-5-yl)propanoate); |
| 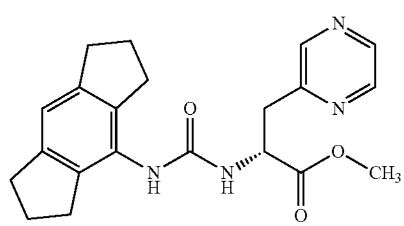 [SMILES: COC(=O)[C@@H](Cc1cnccn1)NC(=O)Nc1c2c(cc3c1CCC3)CCC2] | (methyl (2R)-2-{[(1,2,3,5,6,7-hexahydro-s-indacen-4-yl)carbamoyl]amino}-3-(pyrazin-2-yl)propanoate); |
| 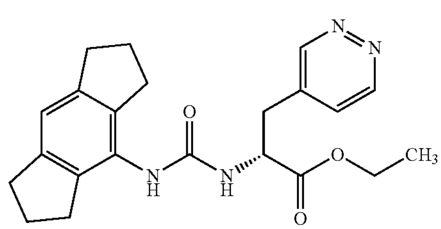 | (ethyl 2-{[(1,2,3,5,6,7-hexahydro-s-indacen-4-yl)carbamoyl]amino}-3-(pyridazin-4-yl)propanoate); |
| 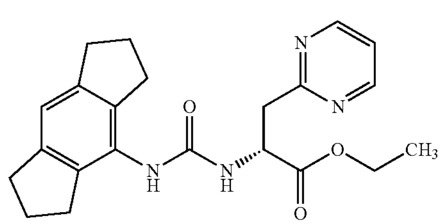 [SMILES: CCOC(=O)[C@@H](Cc1ncccn1)NC(=O)Nc1c2c(cc3c1CCC3)CCC2] | (ethyl (2R)-2-{[(1,2,3,5,6,7-hexahydro-s-indacen-4-yl)carbamoyl]amino}-3-(pyrimidin-2-yl)propanoate); |

-continued

| Structure | Name |
|---|---|
| 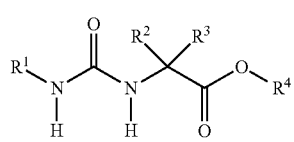 | (ethyl 2-{[(1,2,3,5,6,7-hexahydro-s-indacen-4-yl)carbamoyl]amino}-3-(pyrimidin-4-yl)propanoate); |
| 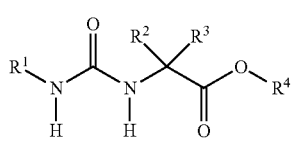 | (2-{[(1,2,3,5,6,7-hexahydro-s-indacen-4-yl)carbamoyl]amino}-3-(pyrimidin-2-yl)propanoic acid). |

9. A compound of Formula (I), or pharmaceutically acceptable salt thereof:

(I)

wherein:
$R_1$ is a 12, 13, 15 or 16 membered tricyclic partially unsaturated carbocyclic ring system, wherein said tricyclic ring system is optionally substituted by 1, 2, 3 or 4 substituents independently selected from (1-6C)alkyl, (2-6C)alkenyl, (2-6C)alkynyl, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$, and $N(CH_3)S(O)_2CH_3$;
$R_2$ is H;
$R_3$ is (1-4C)Alkyl$R_7$;
wherein $R_7$ is selected from a 5 or 6 membered monocyclic aryl or non-aryl ring system comprising 1, 2, or 3 heteroatoms independently selected from oxygen, nitrogen and sulfur, or 3, 4, 5 or 6 membered monocyclic heterocyclyl ring system comprising 1 or 2 heteroatoms independently selected from oxygen, nitrogen and sulfur, wherein said $R_7$ ring system is optionally substituted with 1 or more substituents independently selected from (1-6C)alkyl, alkylhydroxy, nitro, OH, $COCH_3$, halo, amino, cyano, an optionally N-linked 5 or 6 membered monocyclic heteroaryl ring comprising 1 or 2 heteroatoms independently selected from oxygen, nitrogen and sulfur, or an optionally N-linked 3, 4, 5 or 6 membered monocyclic heterocyclyl ring system comprising 1 heteroatom independently selected from oxygen, nitrogen and sulfur, said ring being optionally substituted with an alkyl, oxo, halo, or amino group; and
$R_4$ is H, alkyl, monocyclic saturated carbocyclic ring system, or monocyclic aryl group.

10. A compound of Formula (I), or pharmaceutically acceptable salt thereof:

(I)

wherein:
$R_1$ is a 12, 13, 15 or 16 membered tricyclic partially unsaturated carbocyclic ring system, wherein said tricyclic ring system is optionally substituted by 1, 2, 3 or 4 substituents independently selected from (1-6C)alkyl, (2-6C)alkenyl, (2-6C)alkynyl, (3-8C)cycloalkyl, (1-3C)alkoxy, halo, oxo, hydroxy, cyano, amino, (1-3C)alkylamino, di-[(1-3C)alkyl]-amino, $CF_3$, $OCF_3$, $S(O)_2CH_3$, $S(O)CH_3$, $S(O)_2NH_2$, $S(O)_2NHCH_3$, $S(O)_2N(CH_3)_2$, $NHS(O)_2CH_3$, and $N(CH_3)S(O)_2CH_3$;
$R_2$ is H;
$R_3$ (1-4C)Alkyl$R_7$,
wherein $R_7$ is selected from a 5 or 6 membered monocyclic aryl or non-aryl ring system optionally comprising 1, 2 or 3 heteroatoms independently selected from oxygen, nitrogen and sulfur, 3, 4, 5 or 6 membered monocyclic heterocyclyl ring system optionally comprising 1 or 2 heteroatoms independently selected from oxygen, nitrogen and sulfur, or a 3, 4, 5 or 6 membered saturated or partially unsaturated carbocyclic ring system and said $R_7$ ring system is substituted with 1 or more substituents independently selected from (1-6C) alkyl, alkylhydroxy, nitro, OH, $COCH_3$, halo, amino, cyano, an optionally N-linked 5 or 6 membered monocyclic heteroaryl ring comprising 1 or 2 heteroatoms independently selected from oxygen, nitrogen and sulfur, and an optionally N-linked 3, 4, 5 or 6 membered monocyclic heterocyclyl ring system comprising 1 heteroatom independently selected from oxygen, nitrogen and sulfur, said ring being optionally substituted with an alkyl, oxo, halo, or amino group; and
$R_4$ is H, alkyl, monocyclic saturated carbocyclic ring system, or monocyclic aryl group.

11. A pharmaceutical composition comprising a compound of claim 1 or a pharmaceutically acceptable salt thereof, in a mixture with a pharmaceutically acceptable diluent or carrier.

12. A method of inhibiting the NLRP3 inflammasome activity in vitro or in vivo, said method comprising contacting a cell with an effective amount of a compound of claim 1 or a pharmaceutically acceptable salt thereof.

13. The method of claim 12, wherein the cell is in a patient suffering from a disease or disorder in which inflammasome activity is implicated.

14. The method of claim 13, wherein the disease or disorder in which inflammasome activity is implicated is an auto-inflammatory disorder, an autoimmune disorder, a neurodegenerative disease or cancer.

15. The method of claim 14, wherein the disorder is selected from gastrointestinal cancer, skin cancer, non-small-cell lung carcinoma, and colorectal adenocarcinoma.

16. The method of claim 14, wherein the disorder is selected from cryopyrin-associated auto-inflammatory syndrome (CAPS) including familial cold auto-inflammatory syndrome (FCAS), Muckle-Wells syndrome (MWS), chronic infantile neurological cutaneous and articular (CINCA) syndrome, neonatal-onset multisystem inflammatory disease (NOMID), familial Mediterranean fever, non-alcoholic fatty liver disease (NAFLD), gout, rheumatoid arthritis, Crohn's disease, COPD, fibrosis, obesity, type 2 diabetes, multiple sclerosis, neuro-inflammation occurring in protein misfolding diseases, Parkinson's disease, osteoarthritis, Non-alcoholic steatohepatitis (NASH), and Alzheimer's disease.

17. A method of inhibiting the NLRP3 inflammasome activity in vitro or in vivo, said method comprising contacting a cell with an effective amount of a compound of claim 9 or a pharmaceutically acceptable salt thereof.

18. The method of claim 17, wherein the cell is in a patient suffering from a disease or disorder in which inflammasome activity is implicated.

19. A method of inhibiting the NLRP3 inflammasome activity in vitro or in vivo, said method comprising contacting a cell with an effective amount of a compound of claim 10 or a pharmaceutically acceptable salt thereof.

20. The method of claim 19, wherein the cell is in a patient suffering from a disease or disorder in which inflammasome activity is implicated.

* * * * *

UNITED STATES PATENT AND TRADEMARK OFFICE
CERTIFICATE OF CORRECTION

| | | |
|---|---|---|
| PATENT NO. | : 11,345,669 B2 | Page 1 of 2 |
| APPLICATION NO. | : 16/493816 | |
| DATED | : May 31, 2022 | |
| INVENTOR(S) | : David Harrison et al. | |

It is certified that error appears in the above-identified patent and that said Letters Patent is hereby corrected as shown below:

In the Claims

Claim 8, Column 135, Second Structure:

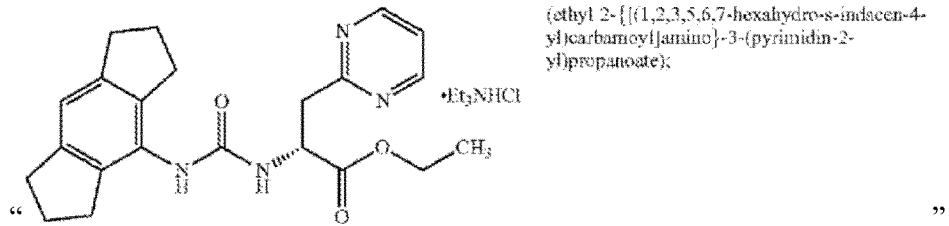

Should read:

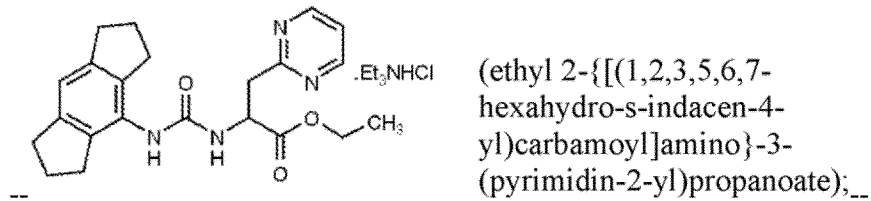

(ethyl 2-{[(1,2,3,5,6,7-hexahydro-s-indacen-4-yl)carbamoyl]amino}-3-(pyrimidin-2-yl)propanoate);

Claim 8, Column 137, Sixth Structure:

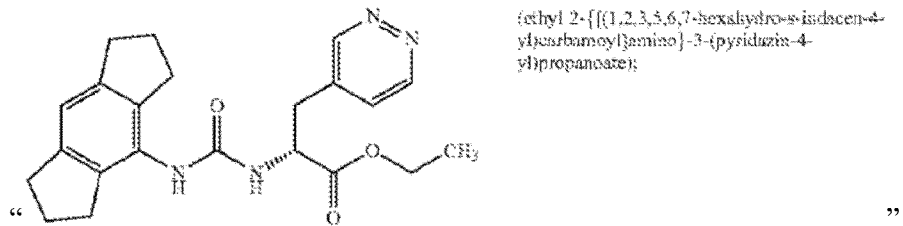

Signed and Sealed this
Twenty-ninth Day of November, 2022

Katherine Kelly Vidal
*Director of the United States Patent and Trademark Office*

CERTIFICATE OF CORRECTION (continued)
U.S. Pat. No. 11,345,669 B2

Page 2 of 2

Should read:

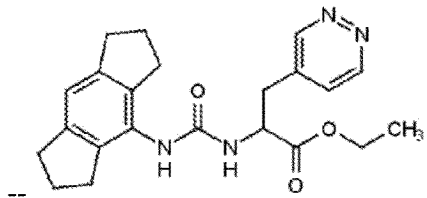

(ethyl 2-{[(1,2,3,5,6,7-hexahydro-s-indacen-4-yl)carbamoyl]amino}-3-(pyridazin-4-yl)propanoate);

Claim 8, Column 139, Second Structure:

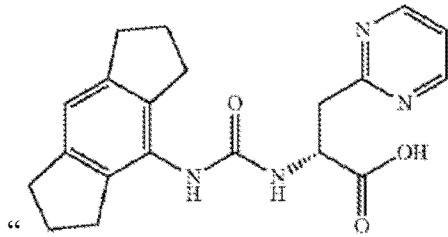

(2-{[(1,2,3,5,6,7-hexahydro-s-indacen-4-yl)carbamoyl]amino}-3-(pyrimidin-2-yl)propanoic acid).

Should read:

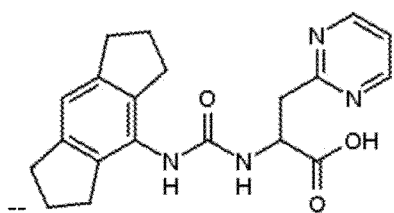

(2-{[(1,2,3,5,6,7-hexahydro-s-indacen-4-yl)carbamoyl]amino}-3-(pyrimidin-2-yl)propanoic acid).